US011969536B2

(12) United States Patent
Kusters et al.

(10) Patent No.: US 11,969,536 B2
(45) Date of Patent: Apr. 30, 2024

(54) SYSTEMS ENABLING ALTERNATIVE APPROACHES TO THERAPEUTIC RED BLOOD CELL EXCHANGE AND/OR THERAPEUTIC PLASMA EXCHANGE

(71) Applicant: Fenwal, Inc., Lake Zurich, IL (US)

(72) Inventors: Benjamin E Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 503 days.

(21) Appl. No.: 17/117,203

(22) Filed: Dec. 10, 2020

(65) Prior Publication Data

US 2021/0178051 A1 Jun. 17, 2021

Related U.S. Application Data

(60) Provisional application No. 62/947,027, filed on Dec. 12, 2019.

(51) Int. Cl.
*A61M 1/36* (2006.01)

(52) U.S. Cl.
CPC ........ *A61M 1/3693* (2013.01); *A61M 1/3607* (2014.02); *A61M 1/3621* (2013.01);
(Continued)

(58) Field of Classification Search
CPC .. A61M 1/265; A61M 1/3607; A61M 1/3621; A61M 1/3693; A61M 1/38;
(Continued)

(56) References Cited

U.S. PATENT DOCUMENTS

| 5,194,145 A | 3/1993 | Schoendorfer |
| 5,632,893 A | 5/1997 | Brown et al. |

(Continued)

FOREIGN PATENT DOCUMENTS

| EP | 1946784 B1 | 10/2012 |
| EP | 2987512 A1 | 2/2016 |

(Continued)

OTHER PUBLICATIONS

Extended European Search Report, dated May 14, 2021, for European patent application No. 20212981.3-1113.

*Primary Examiner* — Dirk R Bass
(74) *Attorney, Agent, or Firm* — Cook Alex Ltd.

(57) ABSTRACT

Systems and methods are provided for therapeutic red blood cell exchange and/or therapeutic plasma exchange. A blood separation device includes a centrifugal separator, a spinning membrane separator drive unit, a pump system, and a controller. Blood is conveyed through a fluid flow circuit into either the centrifugal separator or the spinning membrane separator, which separates out the target blood component (red blood cells, in the case of therapeutic red blood cell exchange, or plasma, in the case of therapeutic plasma exchange). The target blood component is retained in the circuit as a waste product, while a replacement fluid is added to the remaining blood component(s), which is then conveyed to a recipient. In addition to allowing for execution of an exchange procedure using either a centrifugal separator or a spinning membrane separator drive unit, the blood separation device also allows for the use of differently sized spinning membrane separators.

18 Claims, 31 Drawing Sheets

(52) U.S. Cl.
CPC .. *A61M 1/362227* (2022.05); *A61M 1/36224* (2022.05); *A61M 1/36225* (2022.05); *A61M 1/362261* (2022.05); *A61M 1/362265* (2022.05); *A61M 1/362266* (2022.05); *A61M 2202/0415* (2013.01); *A61M 2202/0427* (2013.01); *A61M 2202/0429* (2013.01)

(58) Field of Classification Search
CPC .. A61M 2202/0415; A61M 2202/0427; A61M 2202/0429; A61M 2205/12; A61M 2205/3306
See application file for complete search history.

(56) References Cited

U.S. PATENT DOCUMENTS

| | | |
|---|---|---|
| 5,868,696 A | 2/1999 | Giesler et al. |
| 6,419,822 B2 | 7/2002 | Muller et al. |
| 6,471,855 B1 | 10/2002 | Odak et al. |
| 6,579,219 B2 | 6/2003 | Dolecek et al. |
| 6,582,386 B2 | 6/2003 | Min et al. |
| 6,629,919 B2 | 10/2003 | Egozy et al. |
| 6,706,008 B2 | 3/2004 | Vishnoi et al. |
| 6,770,883 B2 | 8/2004 | McNeal et al. |
| 6,808,503 B2 | 10/2004 | Farrell et al. |
| 6,866,826 B2 | 3/2005 | Moore et al. |
| 6,884,228 B2 | 4/2005 | Brown et al. |
| 7,049,622 B1 | 5/2006 | Weiss |
| 7,081,082 B2 | 7/2006 | Scholz et al. |
| 7,150,834 B2 | 12/2006 | Mueth et al. |
| 7,186,230 B2 | 3/2007 | Briggs et al. |
| 7,186,231 B2 | 3/2007 | Takagi et al. |
| 7,211,037 B2 | 5/2007 | Briggs et al. |
| 7,294,513 B2 | 11/2007 | Wyatt |
| 7,347,948 B2 | 3/2008 | Dolecek et al. |
| 7,354,515 B2 | 4/2008 | Coull et al. |
| 7,381,291 B2 | 6/2008 | Tobe et al. |
| 7,422,693 B2 | 9/2008 | Carter et al. |
| 7,485,084 B2 | 2/2009 | Borgstrom et al. |
| 7,563,376 B2 | 7/2009 | Oishi |
| 7,648,639 B2 | 1/2010 | Holmes et al. |
| 7,806,845 B2 | 10/2010 | Arm et al. |
| 7,906,771 B2 | 3/2011 | Carter et al. |
| 7,951,059 B2 | 5/2011 | Sweat |
| 8,057,377 B2 | 11/2011 | Holmes et al. |
| 8,075,468 B2 | 12/2011 | Min et al. |
| 8,163,276 B2 | 4/2012 | Hedrick et al. |
| 8,287,742 B2 | 10/2012 | Holmes |
| 8,317,672 B2 | 11/2012 | Nash et al. |
| 8,337,379 B2 | 12/2012 | Fletcher et al. |
| 8,535,210 B2 | 9/2013 | Kolenbrander et al. |
| 8,556,793 B2 | 10/2013 | Foley et al. |
| 8,758,211 B2 | 6/2014 | Nash et al. |
| 8,974,362 B2 | 3/2015 | Nash et al. |
| 9,011,687 B2 | 4/2015 | Swift et al. |
| 9,156,039 B2 | 10/2015 | Holmes et al. |
| 9,302,042 B2 | 4/2016 | Pagès |
| 9,302,276 B2 | 4/2016 | Pesetsky et al. |
| 9,370,615 B2 | 6/2016 | Ragusa et al. |
| 9,399,182 B2 | 7/2016 | Pesetsky et al. |
| 9,550,016 B2 | 1/2017 | Gifford |
| 9,610,590 B2 | 4/2017 | Hamandi |
| 9,789,235 B2 | 10/2017 | Gifford |
| 10,086,128 B2 | 10/2018 | Kyle et al. |
| 10,166,322 B2 | 1/2019 | Sweat et al. |
| 10,238,787 B2 | 3/2019 | Takuwa |
| 10,293,097 B2 | 5/2019 | Murphy et al. |
| 10,399,881 B2 | 9/2019 | Donais et al. |
| 10,493,467 B2 | 12/2019 | Lundquist et al. |
| 10,518,007 B2 | 12/2019 | Kimura |
| 10,561,783 B2 | 2/2020 | Hamandi et al. |
| 2002/0128583 A1 | 9/2002 | Min et al. |
| 2004/0195190 A1 | 10/2004 | Min et al. |
| 2009/0215602 A1 | 8/2009 | Min et al. |
| 2011/0003675 A1 | 1/2011 | Dolecek |
| 2011/0294641 A1 | 12/2011 | Dolecek et al. |
| 2014/0378292 A1 | 12/2014 | Igarashi |
| 2015/0068959 A1 | 3/2015 | Zheng |
| 2015/0104824 A1 | 4/2015 | Walker |
| 2015/0218517 A1 | 8/2015 | Kusters et al. |
| 2015/0367063 A1 | 12/2015 | Kimura |
| 2017/0153431 A1 | 6/2017 | Nguyen et al. |
| 2018/0043374 A1 | 2/2018 | Meinig et al. |
| 2018/0164141 A1 | 6/2018 | Bordignon et al. |
| 2018/0185772 A1 | 7/2018 | Karhiniemi et al. |
| 2019/0003873 A1 | 1/2019 | Araujo et al. |
| 2019/0030545 A1 | 1/2019 | Hamada et al. |
| 2019/0083696 A1 | 3/2019 | Igarashi |
| 2019/0201916 A1* | 7/2019 | Min ................ A61M 1/029 |

FOREIGN PATENT DOCUMENTS

| | | |
|---|---|---|
| WO | WO2012/091720 A1 | 7/2012 |
| WO | WO2013/043433 A2 | 3/2013 |
| WO | WO 2014/039091 A1 | 3/2014 |
| WO | WO2018/053217 A1 | 3/2018 |
| WO | WO2018/154115 A2 | 8/2018 |
| WO | WO2019/047498 A1 | 3/2019 |
| WO | WO2019/165478 A1 | 8/2019 |
| WO | WO2020/002059 A1 | 1/2020 |
| WO | WO2020/055958 A1 | 3/2020 |

* cited by examiner

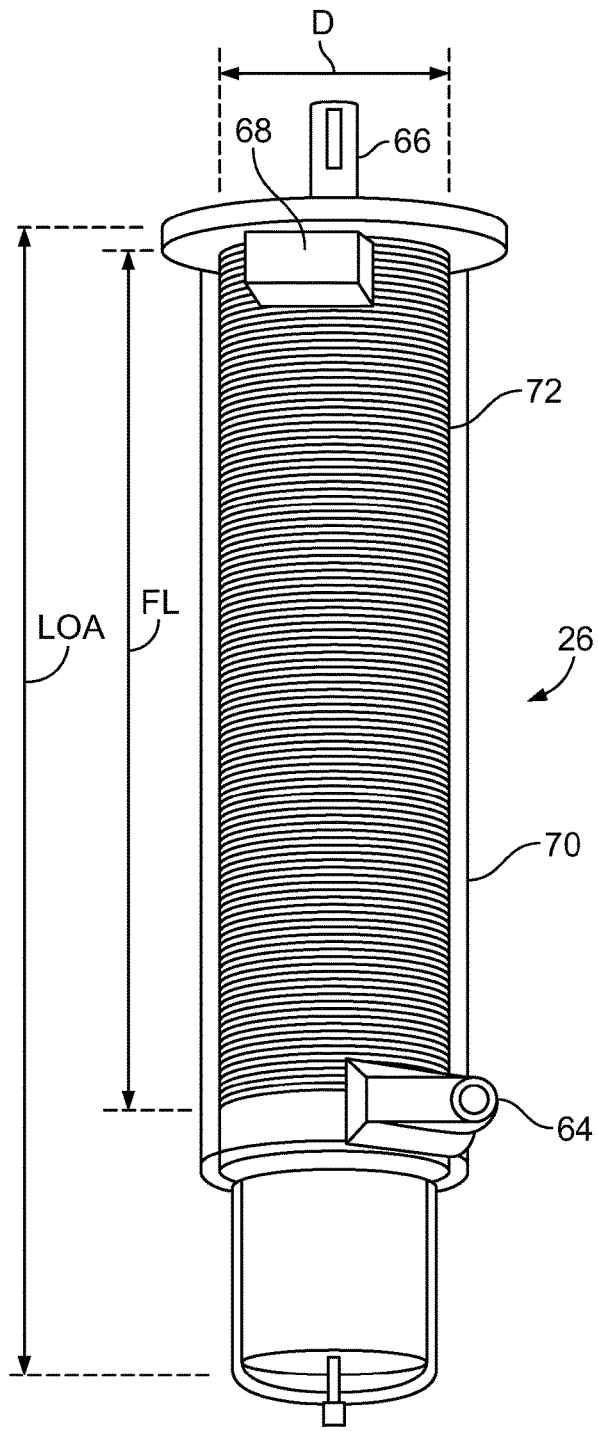 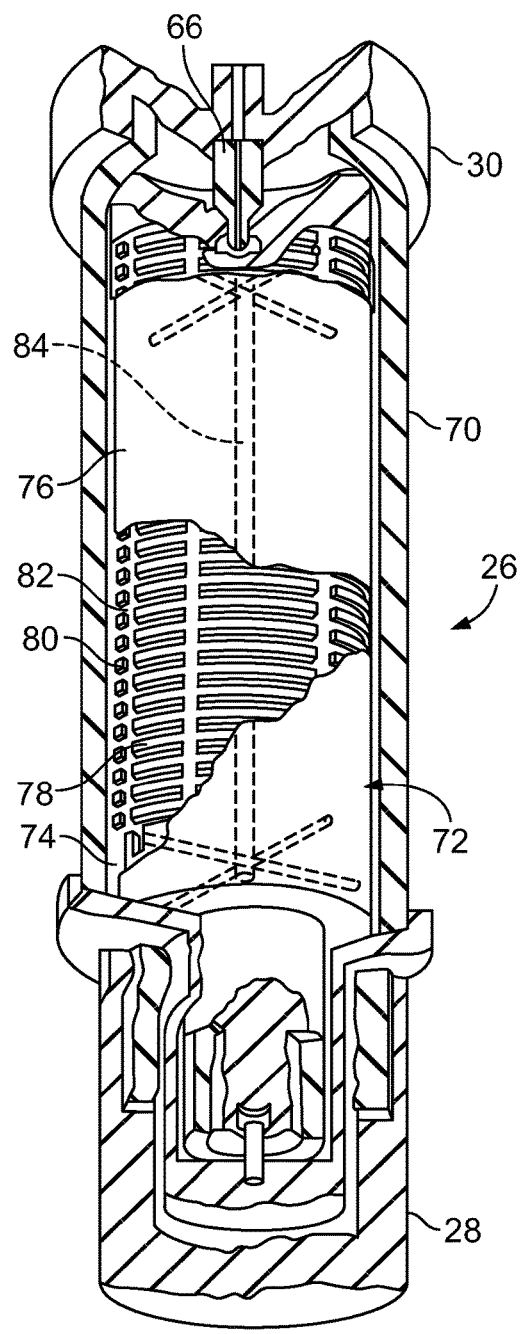
FIG. 8  FIG. 9

SYSTEMS ENABLING ALTERNATIVE APPROACHES TO THERAPEUTIC RED BLOOD CELL EXCHANGE AND/OR THERAPEUTIC PLASMA EXCHANGE

CROSS-REFERENCE TO RELATED APPLICATIONS

This application claims the benefit of and priority of U.S. Provisional Patent Application Ser. No. 62/947,027, filed Dec. 12, 2019, the contents of which are incorporated by reference herein.

BACKGROUND

Field of the Disclosure

The present disclosure relates to systems for therapeutic red blood cell exchange and/or therapeutic plasma exchange. More particularly, the present disclosure relates to systems for selectively performing therapeutic red blood cell exchange and/or therapeutic plasma exchange using either a centrifugal separator or a spinning membrane separator drive unit.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber.

While many blood separation systems and procedures have employed centrifugal separation principles, there is another class of devices, based on the use of a membrane, that has been used for plasmapheresis (i.e., separating plasma from whole blood). More specifically, this type of device employs relatively rotating surfaces, at least one or which carries a porous membrane. Typically, the device employs an outer stationary housing and an internal spinning rotor covered by a porous membrane.

Well-known plasmapheresis devices include the Autopheresis-C® and Aurora separators sold by Fenwal, Inc. of Lake Zurich, Illinois, which is an affiliate of Fresenius Kabi AG of Bad Homburg, Germany. A detailed description of an exemplary spinning membrane separator may be found in U.S. Pat. No. 5,194,145, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, platelets, and white blood cells, move to the exit region between the spinner and the shell and then may be collected, returned to a blood source, or discarded.

Spinning membrane separators have been found to provide excellent plasma filtration rates, due primarily to the unique flow patterns ("Taylor vortices") induced in the gap between the spinning membrane and the shell. The Taylor vortices help to keep the blood cells from depositing on and fouling or clogging the membrane.

Both types of separators have their advantages, so it would be advantageous to provide an integrated system capable of harnessing the benefits of both centrifugal separation and spinning membrane separation. Such an integrated system is described in PCT Patent Application Publication No. WO 2018/053217 A1, which is hereby incorporated herein by reference. Such a system is very versatile, allowing for any of a number of blood separation procedures to be carried out using one or both of centrifugal and spinning membrane separation techniques.

One subset of procedures not described in PCT Patent Application Publication No. WO 2018/053217 A1 is therapeutic exchange procedures. In a therapeutic exchange procedure, a target blood component (e.g., red blood cells or platelets) is removed from other blood cells and replaced with a replacement fluid (e.g., donated red blood cells, in the case of a therapeutic red blood cell exchange procedure, or donated plasma, in the case of a therapeutic plasma exchange procedure). A conventional blood separation device is limited to execution of a therapeutic exchange procedure using only one separation technology. However, there are certain situations (e.g., depending on the size and/or health of the blood source, in the case of a living human as a blood source) in which one technique is preferable over the other. Thus, it would be advantageous to employ a blood separation device of the type described in PCT Patent Application Publication No. WO 2018/053217 A1 for therapeutic exchange procedures, because its versatility would allow for execution of a therapeutic exchange procedure using either centrifugal or spinning membrane separation techniques.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood separation device includes a centrifugal separator, a spinning membrane separator drive unit, a pump system, and a controller configured to control the centrifugal separator or the spinning membrane separator drive unit to execute a therapeutic red blood cell exchange procedure. When controlling the centrifugal separator to execute a therapeutic red blood cell exchange procedure, the controller controls the pump system to convey blood from a blood source into the centrifugal separator and controls the centrifugal separator to separate at least a portion of the blood into red blood cells and at least one other blood component. The controller then controls the pump system to collect at least a portion of the separated red blood cells and controls the pump system to add a red blood cell replacement fluid to said at least one other blood component. The controller then controls the pump system to convey at least a portion of the red blood cell replacement fluid and said at least one other blood component to a recipient. When controlling the spinning membrane separator drive unit to execute a therapeutic red blood cell exchange procedure, the controller controls the pump system to convey blood from a blood source into the spinning membrane separator drive unit and controls the spinning membrane separator drive unit to separate at least a portion of the blood into red blood cells and at least one other blood component. The controller then controls the pump system to collect at least a portion of the separated red blood cells and controls the pump system to add a red blood cell replacement fluid to said at least one other blood component. The controller then controls the pump system to convey at least a portion of the red blood cell replacement fluid and said at least one other blood component to a recipient.

In another aspect, a blood separation device includes a centrifugal separator, a spinning membrane separator drive unit, a pump system, and a controller configured to control the centrifugal separator or the spinning membrane separator drive unit to execute a therapeutic plasma exchange procedure. When controlling the centrifugal separator to execute a therapeutic plasma exchange procedure, the controller controls the pump system to convey blood from a blood source into the centrifugal separator and controls the centrifugal separator to separate at least a portion of the blood into plasma and at least one other blood component. The controller then controls the pump system to collect at least a portion of the separated plasma and controls the pump system to add a plasma replacement fluid to said at least one other blood component. The controller then controls the pump system to convey at least a portion of the plasma replacement fluid and said at least one other blood component to a recipient. When controlling the spinning membrane separator drive unit to execute a therapeutic plasma exchange procedure, the controller controls the pump system to convey blood from a blood source into the spinning membrane separator drive unit and controls the spinning membrane separator drive unit to separate at least a portion of the blood into plasma and at least one other blood component. The controller then controls the pump system to collect at least a portion of the separated plasma and controls the pump system to add a plasma replacement fluid to said at least one other blood component. The controller then controls the pump system to convey at least a portion of the plasma replacement fluid and said at least one other blood component to a recipient.

BRIEF DESCRIPTION OF THE DRAWINGS

FIG. 8 is a perspective view of an exemplary spinning membrane separator of a fluid flow circuit;

FIG. 9 is a perspective view of the spinning membrane separator of FIG. 8 and a portion of a spinning membrane separator drive unit, with portions of both being cut away for illustrative purposes;

DESCRIPTION OF THE ILLUSTRATED EMBODIMENTS

Figure 1:
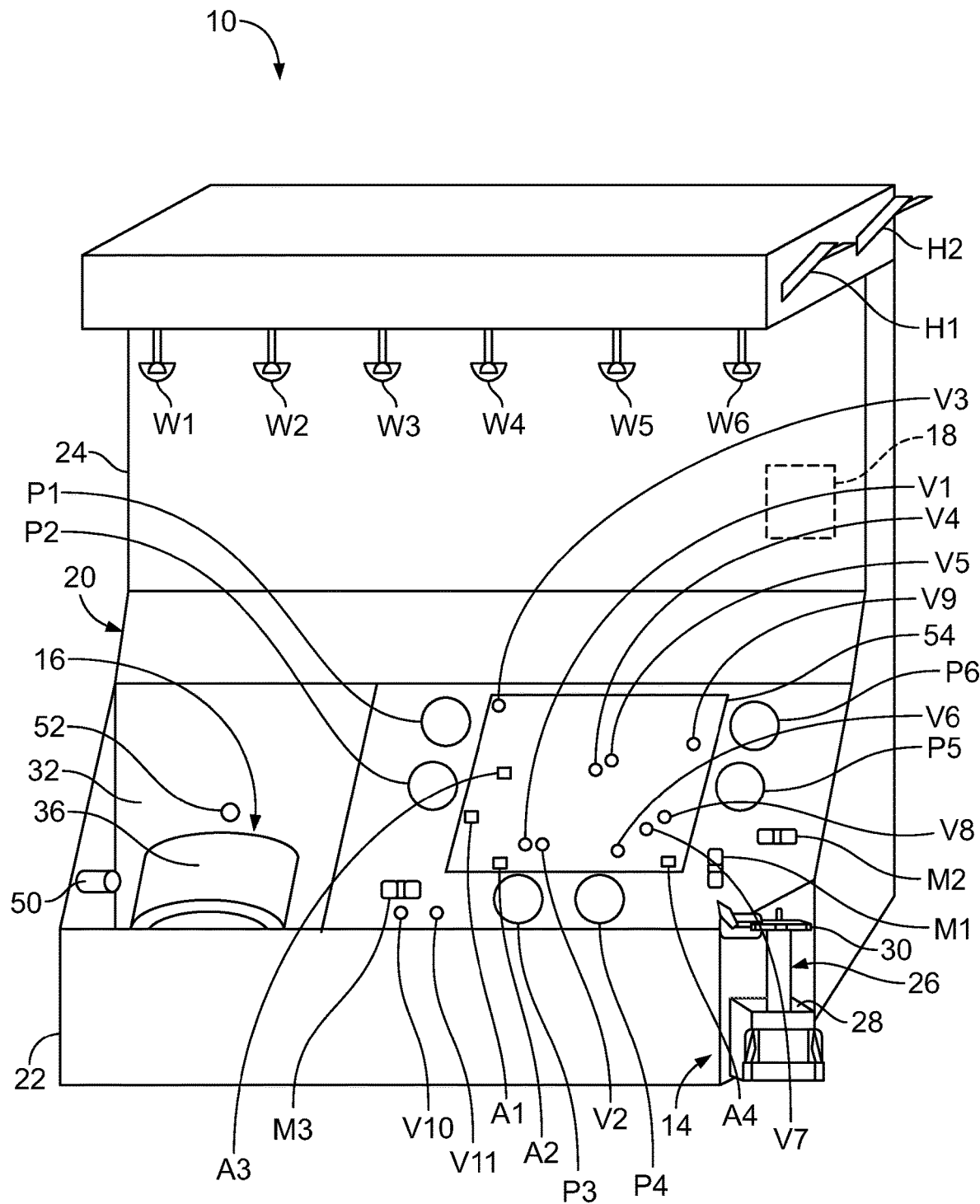
FIG. 1 is a perspective view of an exemplary blood separation device according to an aspect of the present disclosure.

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-50 show components of a blood or fluid separation system that embodies various aspects of the present subject matter. Generally speaking, the system includes two principal components, a durable and reusable blood separation device 10 (FIG. 1) and a disposable fluid flow circuit 12a-12h (FIGS. 2A-2H, which may be collectively referenced herein as element 12). The blood separation device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the blood separation device 10 to perform a blood processing and collection procedure selected by the operator, as will be described in greater detail

I. The Durable Blood Separation Device

The blood separation device 10 (FIG. 1) is configured as a durable item that is capable of long-term use. It should be understood that the blood separation device 10 of FIG. 1 is merely exemplary of one possible configuration and that blood separation devices according to the present disclosure may be differently configured.

In the illustrated embodiment, the blood separation device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24. The configuration and operation of the spinning membrane separator drive unit 14, the centrifugal separator 16, the controller 18, and selected other components of the blood separation device 10 will be described in greater detail.

In the illustrated embodiment, the generally horizontal portion 22 is intended to rest on an elevated, generally horizontal support surface (e.g., a countertop or a tabletop), but it is also within the scope of the present disclosure for the case 20 to include a support base to allow the case 20 to be appropriately positioned and oriented when placed onto a floor or ground surface. It is also within the scope of the present disclosure for the case 20 to be mounted to a generally vertical surface (e.g., a wall), by either fixedly or removably securing the generally vertical portion 24 of the case 20 to the surface.

The case 20 may be configured to assume only the position or configuration of FIG. 1 or may be configured to move between two or more positions or configurations. For example, in one embodiment, the generally horizontal and vertical portions 22 and 24 are joined by a hinge or pivot, which allows the case 20 to be moved between a functional or open configuration (FIG. 1) in which the generally vertical portion 24 is oriented at approximately 90 degrees to the generally horizontal portion 22 and a transport or closed configuration in which the generally vertical portion 24 is rotated about the hinge to approach the generally horizontal portion 22. In such a reconfigurable embodiment, the generally vertical portion 24 may be considered to be the lid of the case 20, while the generally horizontal portion 22 may be considered to be the base. If the case 20 is so reconfigurable, then it may include a latch for releasably locking the case 20 in its closed configuration and/or a handle, which may be grasped for transporting the case 20 in its closed configuration.

While it may be advantageous for the blood separation device 10 to be embodied in a compact, portable case 20, it is also within the scope of the present disclosure for the blood separation device to be embodied in a larger case or fixture that is intended to be installed in a single location and remain in that location for an extended period of time. If the blood separation device is provided as a fixture, it may be provided with more components and functionality than a more portable version.

A. Spinning Membrane Separator Drive Unit

The illustrated blood separation device 10 includes a spinner support or spinning membrane separator drive unit 14 (FIG. 1) for accommodating a generally cylindrical spinning membrane separator 26 of the fluid flow circuit 12 (FIGS. 2A, 2B, 2E, and 2F). U.S. Pat. No. 5,194,145 describes an exemplary spinning membrane separator drive unit that would be suitable for incorporation into the blood separation device 10, but it should be understood that the spinning membrane separator drive unit 14 may be differently configured without departing from the scope of the present disclosure.

The illustrated spinning membrane separator drive unit 14 has a base 28 configured to receive a lower portion of the spinning membrane separator 26 and an upper end cap 30 to receive an upper portion of the spinning membrane separator 26. Preferably, the upper end cap 30 is positioned directly above the base 28 to orient a spinning membrane separator 26 received by the spinning membrane separator drive unit 14 vertically and to define a vertical axis about which the spinning membrane separator 26 is spun. While it may be advantageous for the spinning membrane separator drive unit 14 to vertically orient a spinning membrane separator 26, it is also within the scope of the present disclosure for the spinning membrane separator 26 to be differently oriented when mounted to the blood separation device 10.

In one embodiment, one of the components of the spinning membrane separator drive unit 14 is movable with respect to the other component, which may allow differently sized spinning membrane separators 26 to be received by the spinning membrane separator drive unit 14. For example, the upper end cap 30 may be translated vertically with respect to the base 28 and locked in a plurality of different positions, with each locking position corresponding to a differently sized spinning membrane separator 26.

At least one of the base 28 and the upper end cap 30 is configured to spin one or more components of the spinning membrane separator 26 about the axis defined by the spinning membrane separator drive unit 14. The mechanism by which the spinning membrane separator drive unit 14 spins one or more components of the spinning membrane separator 26 may vary without departing from the scope of the present disclosure. In one embodiment, a component of the spinning membrane separator 26 to be spun includes at least one element configured to be acted upon by a magnet (e.g., a metallic material), while the spinning membrane separator drive unit 14 includes a magnet (e.g., a series of magnetic coils or semi-circular arcs). By modulating the magnetic field acting upon the aforementioned element of the spinning membrane separator 26, the component or components of the spinning membrane separator 26 may be made to spin in different directions and at varying speeds. In other embodiments, different mechanisms may be employed to spin the component or components of the spinning membrane separator 26.

Regardless of the mechanism by which the spinning membrane separator drive unit 14 spins the component or components of the spinning membrane separator 26, the component or components of the spinning membrane separator 26 is preferably spun at a speed that is sufficient to create Taylor vortices in a gap between the spinning component and a stationary component of the spinning membrane separator 26 (or a component that spins at a different speed). Fluid to be separated within the spinning membrane separator 26 flows through this gap, and filtration may be dramatically improved by the creation of Taylor vortices.

B. Centrifugal Separator

Figure 3:
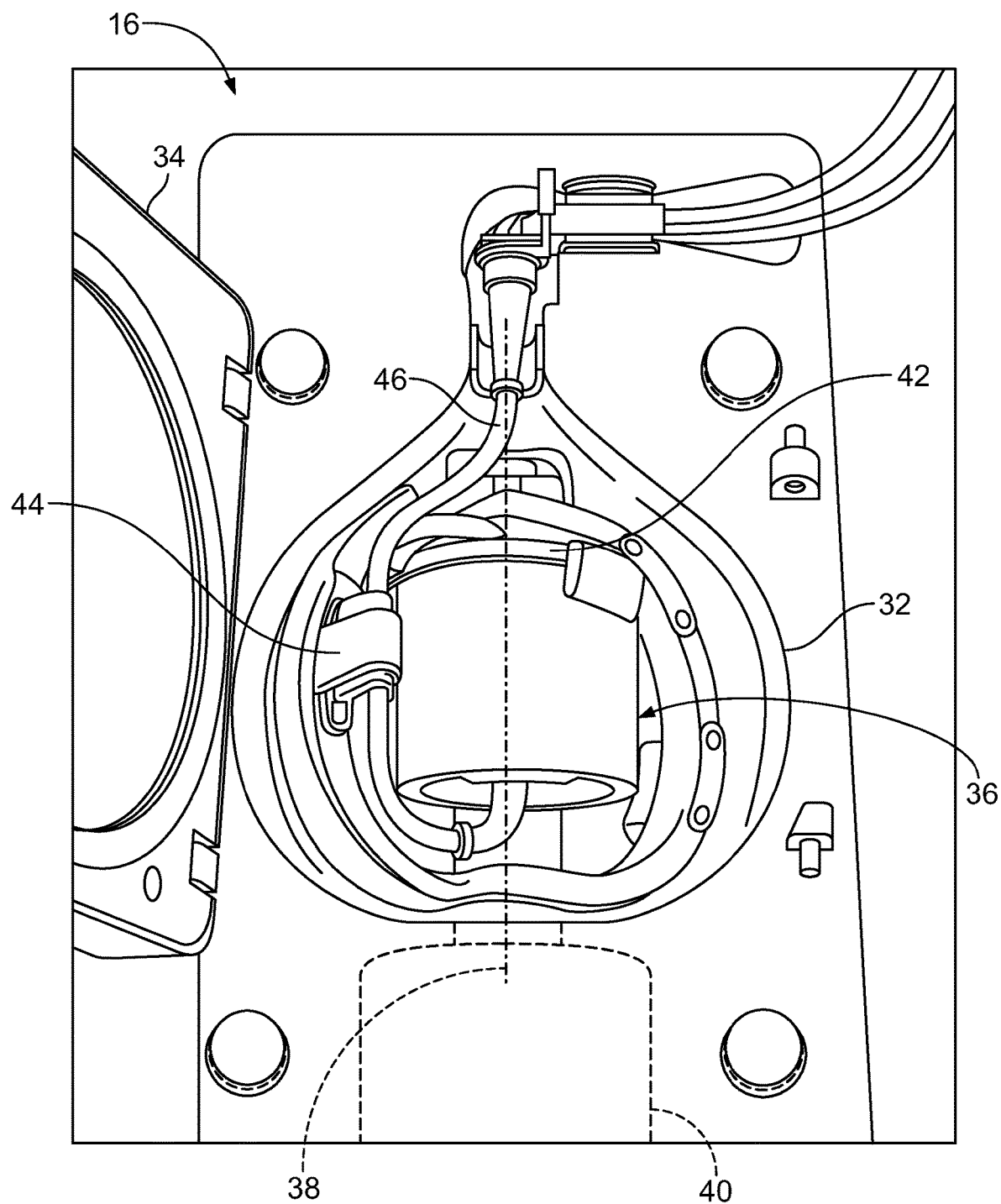
FIG. 3 is a perspective view of an exemplary centrifugal separator of the blood separation device of FIG. 1, with the centrifugal separation chamber of a fluid flow circuit mounted therein.

As for the centrifugal separator 16, it includes a centrifuge compartment 32 that may receive the other components of the centrifugal separator 16 (FIG. 3). The centrifuge compartment 32 may include a lid 34 that is opened to insert and remove a centrifugal separation chamber 36 of the fluid flow circuit 12. During a separation procedure, the lid 34 may be closed with the centrifugal separation chamber 36 positioned within the centrifuge compartment 32, as the centrifugal separation chamber 36 is spun or rotated about an axis 38 under the power of an electric drive motor or rotor 40 of the centrifugal separator 16.

Figure 4:
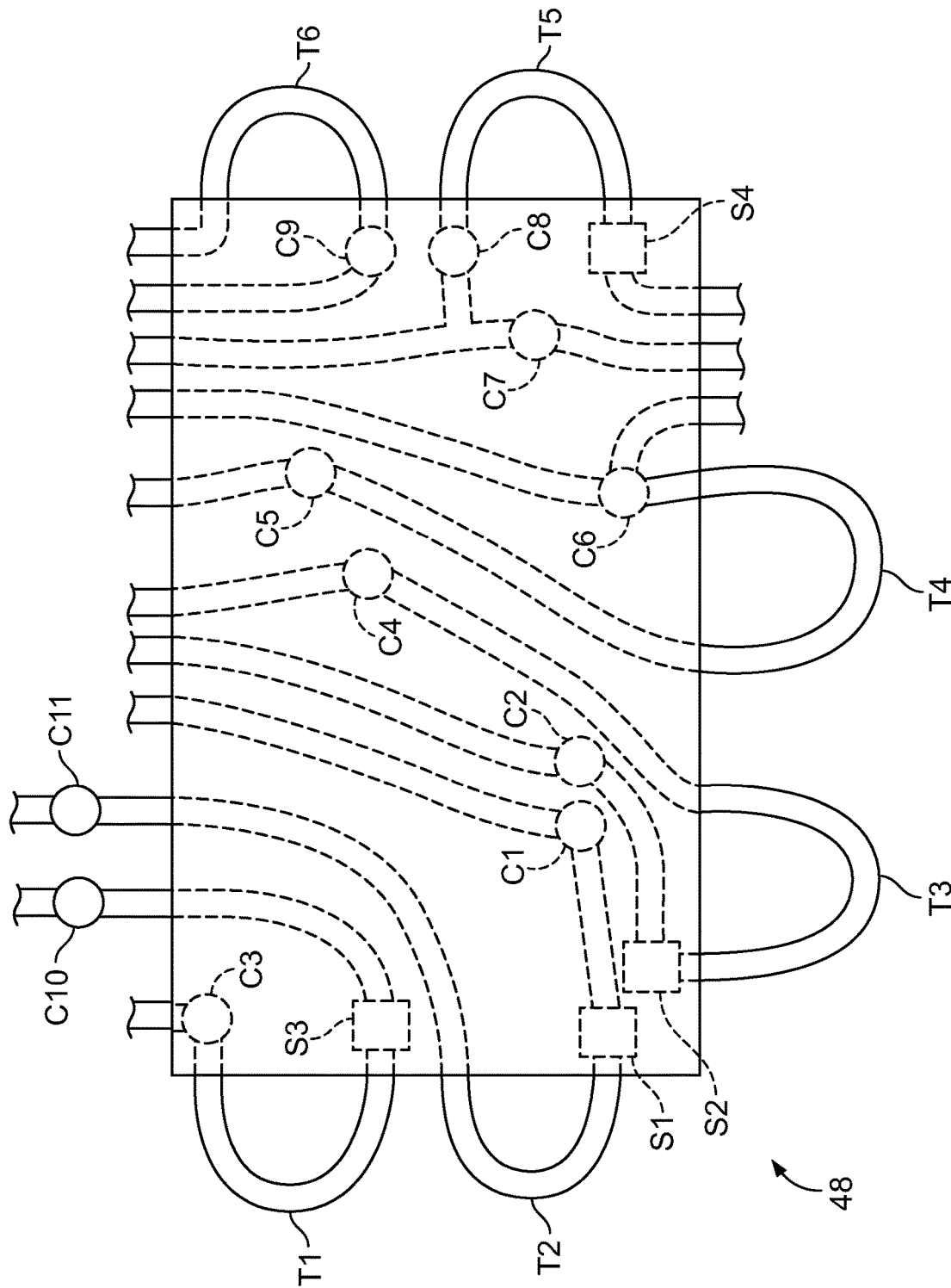
FIG. 4 is a top plan view of an exemplary cassette of a fluid flow circuit, which can be actuated to perform a variety of different blood processing procedures in association with the blood separation device shown in FIG. 1.

The particular configuration and operation of the centrifugal separator 16 depends upon the particular configuration of the centrifugal separation chamber 36 of the fluid flow circuit 12. In one embodiment, the centrifugal separator 16 is similar in structure and operation to that of the ALYX® system manufactured by Fenwal, Inc. of Lake Zurich, Illinois, which is an affiliate of Fresenius Kabi AG of Bad Homburg, Germany, as described in greater detail in U.S. Pat. No. 8,075,468, which is incorporated herein by reference. More particularly, the centrifugal separator 16 may include a carriage or support 42 that holds the centrifugal separation chamber 36 and a yoke member 44. The yoke member 44 engages an umbilicus 46 of the fluid flow circuit 12, which extends between the centrifugal separation chamber 36 and a cassette 48 of the fluid flow circuit 12 (FIG. 4). The yoke member 44 causes the umbilicus 46 to orbit around the centrifugal separation chamber 36 at a one omega rotational speed. The umbilicus 46 twists about its own axis as it orbits around the centrifugal separation chamber 36. The twisting of the umbilicus 46 about its axis as it rotates at one omega with the yoke member 44 imparts a two omega rotation to the centrifugal separation chamber 36, according to known design. The relative rotation of the yoke member 44 at a one omega rotational speed and the centrifugal separation chamber 36 at a two omega rotational speed keeps the umbilicus 46 untwisted, avoiding the need for rotating seals.

Figure 6:
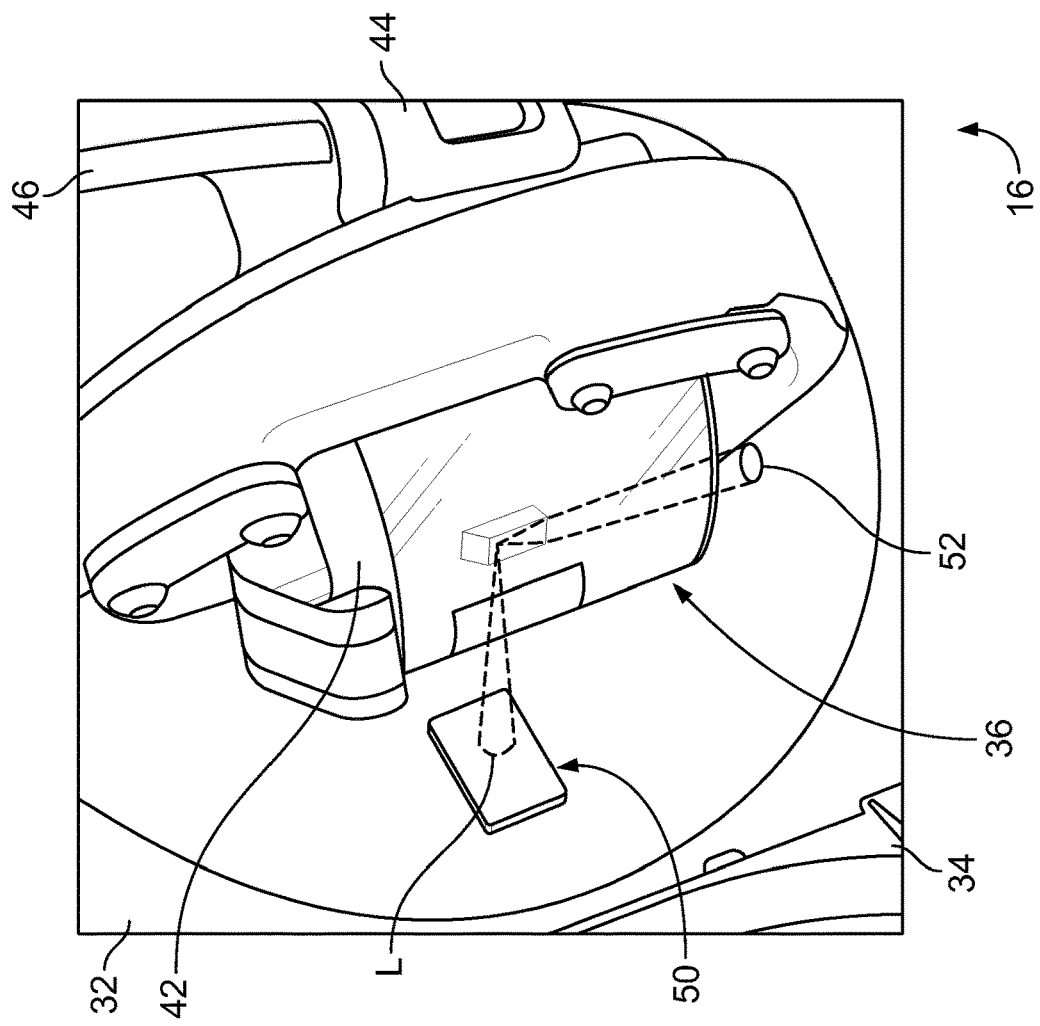
FIG. 6 is a perspective view of the centrifugal separator of FIG. 3, with the light source operating to transmit a light beam to a light detector of the interface monitoring system.
Figure 5:
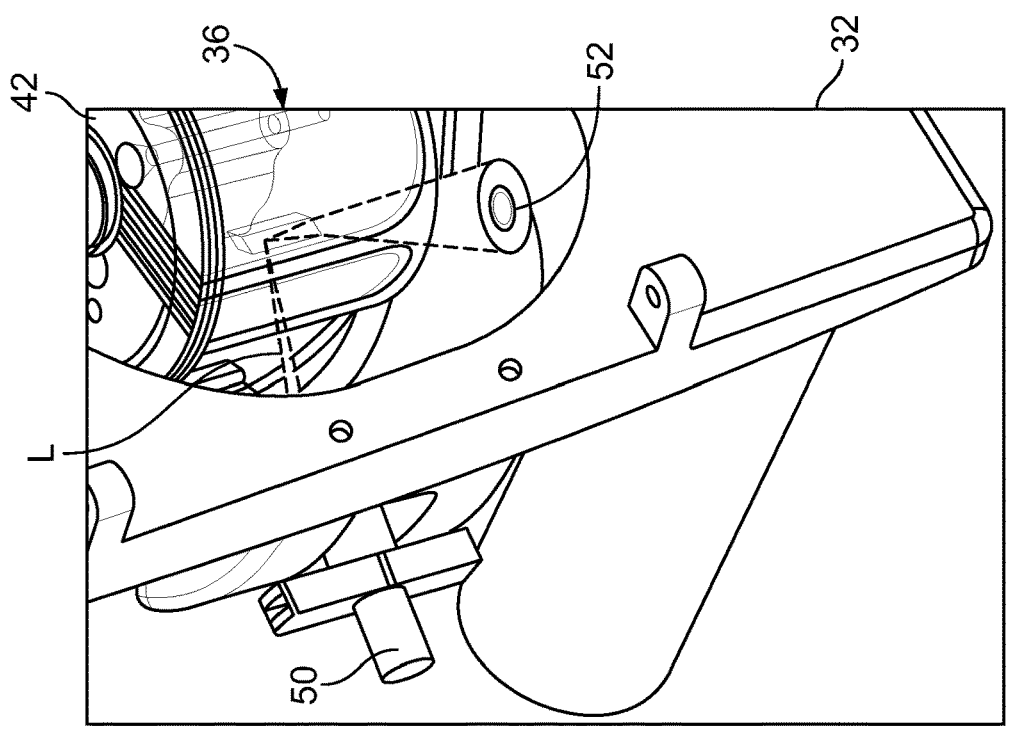
FIG. 5 is a perspective view of the centrifugal separator of FIG. 3, with selected portions thereof broken away to show a light source of an interface monitoring system.
Figure 7:
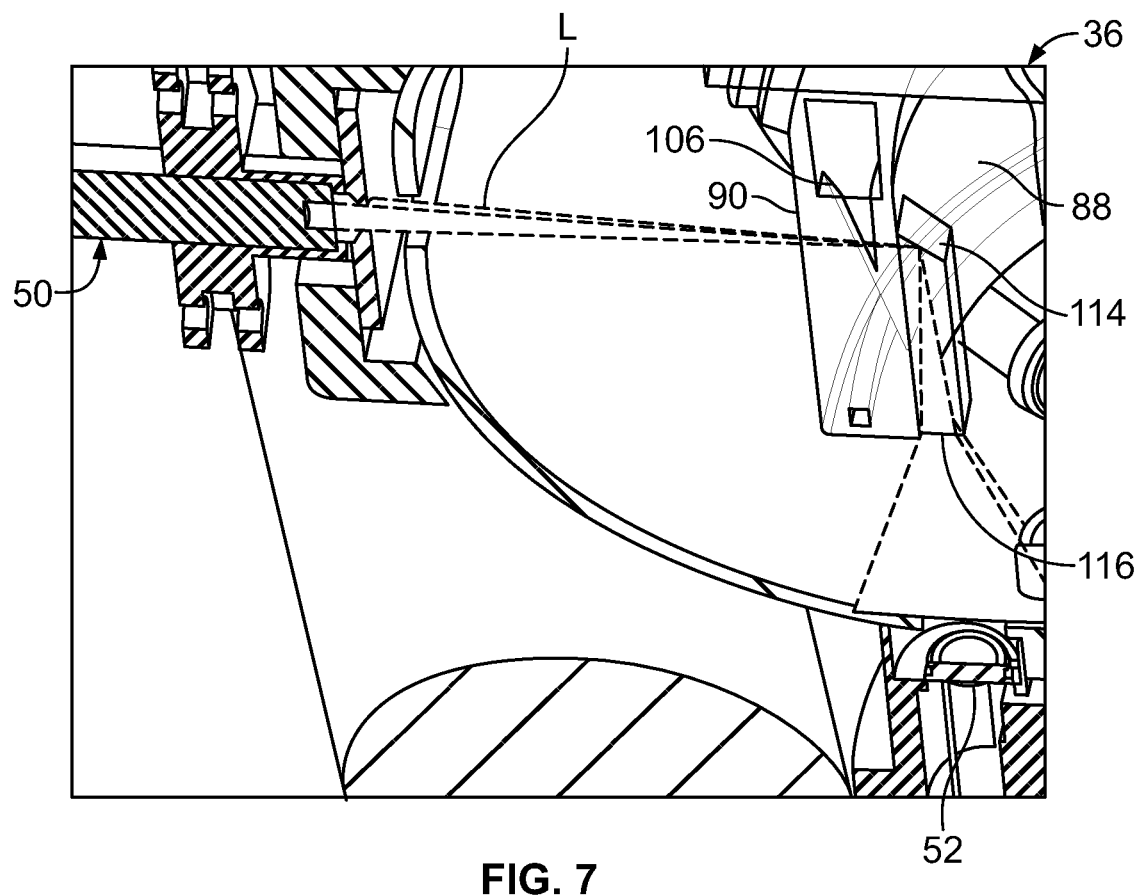
FIG. 7 is a perspective view of the centrifugal separator of FIG. 3, with selected portions thereof broken away to show the light source and light detector of the interface monitoring system.

Blood is introduced into the centrifugal separation chamber 36 by the umbilicus 46, with the blood being separated (e.g., into a layer of less dense components, such as platelet-rich plasma, and a layer of more dense components, such as packed red blood cells) within the centrifugal separation chamber 36 as a result of centrifugal forces as it rotates. Components of an interface monitoring system may be positioned within the centrifuge compartment 32 to oversee separation of blood within the centrifugal separation chamber 36. As shown in FIGS. 5-7, the interface monitoring system may include a light source 50 and a light detector 52, which is positioned and oriented to receive at least a portion of the light emitted by the light source 50. Preferably, the light source 50 and the light detector 52 are positioned on stationary surfaces of the centrifuge compartment 32, but it is also within the scope of the present disclosure for one or both to be mounted to a movable component of the centrifugal separator 16 (e.g., to the yoke member 44, which rotates at a one omega speed).

The orientation of the various components of the interface monitoring system depends at least in part on the particular configuration of the centrifugal separation chamber 36, which will be described in greater detail herein. In general, though, the light source 50 emits a light beam (e.g., a laser light beam) through the separated blood components within the centrifugal separation chamber 36 (which may be formed of a material that substantially transmits the light or at least a particular wavelength of the light without absorbing it). A portion of the light reaches the light detector 52, which transmits a signal to the controller 18 that is indicative of the location of an interface between the separated blood components. If the controller 18 determines that the interface is in the wrong location (which can affect the separation efficiency of the centrifugal separator 16 and/or the quality of the separated blood components), then it can issue commands to the appropriate components of the blood separation device 10 to modify their operation so as to move the interface to the proper location.

C. Other Components of the Blood Separation Device

In addition to the spinning membrane separator drive unit 14 and the centrifugal separator 16, the blood separation device 10 may include other components compactly arranged to aid blood processing.

The generally horizontal portion 22 of the case 20 of the illustrated blood separation device 10 includes a cassette station 54, which accommodates a cassette 48 of the fluid flow circuit 12 (FIG. 4). In one embodiment, the cassette station 54 is similarly configured to the cassette station of U.S. Pat. No. 5,868,696 (which is incorporated herein by reference), but is adapted to include additional components and functionality. The illustrated cassette station 54 includes a plurality of clamps or valves V1-V9 (FIG. 1), which move between a plurality of positions (e.g., between a retracted or lowered position and an actuated or raised position) to selectively contact or otherwise interact with corresponding valve stations C1-C9 of the cassette 48 of the fluid flow circuit 12 (FIGS. 2 and 4). Depending on the configuration of the fluid flow circuit 12, its cassette 48 may not include a valve station C1-C9 for each valve V1-V9 of the cassette station 54, in which case fewer than all of the valves V1-V9 will be used in a separation procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 54 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 54 and cassette 48 may be differently configured and operate differently from the valves V10 and V11 and valve stations C10 and C11 that are spaced away from the cassette station 54.

The cassette station 54 may be provided with additional components, such as pressure sensors A1-A4, which interact with sensor stations S1-S4 of the cassette 48 to monitor the pressure at various locations of the fluid flow circuit 12. For example, if the blood source is a human patient, one or more of the pressure sensors A1-A4 may be configured to monitor the pressure of the patient's vein during blood draw and return. Other pressure sensors A1-A4 may monitor the pressure of the spinning membrane separator 26 and the centrifugal separation chamber 36. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The blood separation device 10 may also include a plurality of pumps P1-P6 (which may be collectively referred to as a pump assembly or pump system) cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 4) and may be selectively operated under command of the controller 18 to cause fluid to flow through a portion of the fluid flow circuit 12, as will be described in greater detail. In one embodiment, all or a portion of the cassette station 54 may be capable of translational motion in and out of the case 20 to allow for automatic loading of the tubing loops T1-T6 into the associated pump P1-P6.

The illustrated blood separation device 10 also includes a centrifugal separator sensor M1 for determining one or more properties of fluids flowing out of and/or into the centrifugal separator 16. If the fluid flowing out of the centrifugal separator 16 includes red blood cells, the centrifugal separator sensor M1 may be configured to determine the hematocrit of the fluid. If the fluid flowing out of the centrifugal separator 16 is platelet-rich plasma, the centrifugal separator sensor M1 may be configured to determine the platelet concentration of the platelet-rich plasma. The centrifugal separator sensor M1 may detect the one or more properties of a fluid by optically monitoring the fluid as it flows through tubing of the fluid flow circuit 12 or by any other suitable approach. The controller 18 may receive signals from the centrifugal separator sensor M1 that are indicative of the one or more properties of fluid flowing out of the centrifugal separator 16 and use the signals to optimize the separation procedure based upon that property or properties. If the property or properties is/are outside of an acceptable range, then the controller 18 may initiate an alarm or error condition to alert an operator to the condition. A suitable device and method for monitoring hematocrit and/or platelet concentration is described in U.S. Pat. No. 6,419,822 (which is incorporated herein by reference), but it should be understood that a different approach may also be employed for monitoring hematocrit and/or platelet concentration of fluid flowing out of the centrifugal separator 16.

The illustrated blood separation device 10 further includes a spinner outlet sensor M2, which accommodates tubing of the fluid flow circuit 12 that flows a separated substance out of the spinning membrane separator 26. The spinner outlet sensor M2 monitors the substance to determine one or more properties of the substance, and may do so by optically monitoring the substance as it flows through the tubing or by any other suitable approach. In one embodiment, separated plasma flows through the tubing, in which case the spinner outlet sensor M2 may be configured to determine the amount of cellular blood components in the plasma and/or whether the plasma is hemolytic and/or lipemic. This may be done using an optical monitor of the type described in U.S. Pat. No. 8,556,793 (which is incorporated herein by reference) or by any other suitable device and/or method.

The illustrated blood separation device 10 also includes an air detector M3 (e.g., an ultrasonic bubble detector), which accommodates tubing of the fluid flow circuit 12 that flows fluid to a recipient. It may be advantageous to prevent air from reaching the recipient, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F7 of the fluid flow circuit 12 (FIGS. 2A-2H). The containers F1-F7 receive blood components or waste products separated during processing or intravenous fluids or additive fluids. Each weight scale W1-W6 transmits to the controller 18 a signal that is indicative of the weight of the fluid within the associated container F1-F7 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports H1 and H2 that may support various components of the fluid flow circuit 12 or other suitably sized and configured objects.

D. Controller

According to an aspect of the present disclosure, the blood separation device 10 includes a controller 18, which is suitably configured and/or programmed to control operation of the blood separation device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the blood separation device 10.

The controller 18 is configured and/or programmed to execute at least one blood processing application but, more advantageously, is configured and/or programmed to execute a variety of different blood processing applications. For example, the controller 18 may be configured and/or programmed to carry out a therapeutic red blood cell exchange procedure and/or a therapeutic plasma exchange procedure. Additional or alternative procedure applications may be included without departing from the scope of the present disclosure.

More particularly, in carrying out any one of these blood processing applications, the controller 18 is configured and/or programmed to control one or more of the following tasks: drawing blood into a fluid flow circuit 12 mounted to the blood separation device 10, conveying blood through the fluid flow circuit 12 to a location for separation (i.e., into a spinning membrane separator 26 or centrifugal separation chamber 36 of the fluid flow circuit 12), separating the blood into two or more components as desired, and conveying the separated components into a storage container or to a recipient (which may be the source from which the blood was originally drawn).

This may include instructing the spinning membrane separator drive unit 14 or the centrifugal separator 16 to operate at a particular rotational speed and instructing a pump P1-P6 to convey fluid through a portion of the fluid flow circuit 12 at a particular flow rate. Hence, while it may be described herein that a particular component of the blood separation device 10 (e.g., the spinning membrane separator drive unit 14 or the centrifugal separator 16) performs a particular function, it should be understood that that component is being controlled by the controller 18 to perform that function.

Before, during, and after a procedure, the controller 18 may receive signals from various components of the blood separation device 10 (e.g., the pressure sensors A1-A4) to monitor various aspects of the operation of the blood separation device 10 and characteristics of the blood and separated blood components as they flow through the fluid flow circuit 12. If the operation of any of the components and/or one or more characteristics of the blood or separated blood components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring system. The signals that the controller 18 receives from the light detector 52 are indicative of the location of an interface between the separated blood components within the centrifugal separation chamber 36. If the controller 18 determines that the interface is in the wrong location, then it can issue commands to the appropriate components of the blood separation device 10 to modify their operation so as to move the interface to the proper location. For example, the controller 18 may instruct one of the pumps P1-P6 to cause blood to flow into the centrifugal separation chamber 36 at a different rate and/or for a separated blood component to be removed from the centrifugal separation chamber 36 at a different rate and/or for the centrifugal separation chamber 36 to be spun at a different speed by the centrifugal separator 16. A particular protocol carried out by the interface control module in adjusting the position of the interface within the centrifugal separation chamber 36 will be described in greater detail with respect to an exemplary centrifugal separation chamber 36.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIGS. 2A-2H), it is intended to be a sterile, single use, disposable item. Before beginning a given blood separation procedure, the operator loads various components of the fluid flow circuit 12 in the case 20 in association with the blood separation device 10. The controller 18 implements the procedure based upon preset protocols, taking into account other input from the operator. Upon completing the procedure, the operator removes the fluid flow circuit 12 from association with the blood separation device 10. The portions of the fluid flow circuit 12 holding the collected blood component or components (e.g., collection containers or bags) are removed from the case 20 and retained for storage, transfusion, or further processing. The remainder of the fluid flow circuit 12 is removed from the case 20 and discarded.

A variety of different disposable fluid flow circuits 12a-12h may be used in combination with the blood separation device 10, with the appropriate fluid flow circuit depending on the separation procedure to be carried out using the system. Accordingly, different fluid flow circuits will be described in connection with particular separation procedures. Generally speaking, though, the fluid flow circuit 12 includes a cassette 48 (FIG. 4), to which the other components of the fluid flow circuit 12 are connected by flexible tubing. The other components may include a plurality of fluid containers F1-F7 (for holding blood, a separated blood component, an intravenous fluid, or an additive solution, for example), one or more blood source access devices (e.g., a connector for accessing blood within a fluid container), and a spinning membrane separator 26 (FIGS. 8 and 9) and/or a centrifugal separation chamber 36 (FIGS. 10-17).

B. Cassette and Tubing

The cassette 48 (FIG. 4) provides a centralized, programmable, integrated platform for all the pumping and many of the valving functions required for a given blood processing procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 54 of the blood separation device 10, with a flexible diaphragm of the cassette 48 placed into contact with the cassette station 54. The flexible diaphragm overlays an array of interior cavities formed by the body of the cassette 48. The different interior cavities define sensor stations S1-S4, valve stations C1-C9, and a plurality of flow paths. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 54, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path). As described above, each valve V1-V9 is movable under command of the controller 18 to move between a plurality of positions (e.g., between a retracted or lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the blood separation device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure, as will be described in greater detail. Certain procedures require fewer than all of the sensor stations, valve stations, and/or tubing loops illustrated in the exemplary cassette 48 of FIG. 4, such that it should be understood that the cassettes of different fluid flow circuits 12 may be differently configured (e.g., with fewer sensor stations, valve stations, and/or tubing loops) without departing from the scope of the present disclosure.

Additional tubing extends from the side surface of the cassette 48 to connect to the other components of the fluid flow circuit 12, such as the various fluid containers F1-F7, the spinning membrane separator 26, and the centrifugal separation chamber 36. The number and content of the various fluid containers F1-F7 depends upon the procedure for which the fluid flow circuit 12 is used, so they will be described in greater detail with respect to the particular procedures. If the fluid flow circuit 12 includes a centrifugal separation chamber 36, then the tubing connected to it (which includes one inlet tube and two outlet tubes) may be aggregated into an umbilicus 46 (FIG. 3) that is engaged by the yoke member 44 of the centrifugal separator 16 (as described above) to cause the umbilicus 46 to orbit around and spin or rotate the centrifugal separation chamber 36 during a separation procedure.

Various additional components may be incorporated into the tubing leading out of the cassette 48 or into one of the cavities of the cassette 48. For example, as shown in FIGS. 2A-2H, a manual clamp 56 may be associated with a line or lines leading to the blood source and/or fluid recipient, a return line filter 58 (e.g., a microaggregate filter) may be associated with a line leading to a fluid recipient, filters may be positioned upstream of one or more of the fluid containers to remove a substance (e.g., leukocytes) from a separated component (e.g., red blood cells) flowing into the fluid container, and/or an air trap 62 may be positioned on a line upstream of the centrifugal separation chamber 36.

C. Spinning Membrane Separator

Turning to FIGS. 8 and 9, a spinning membrane separator 26 is shown. As will be described in greater detail, the spinning membrane separator 26 may be used to separate plasma from cellular blood components during a therapeutic exchange procedure. The spinning membrane separator 26 (if provided) is associated with the remainder of the fluid flow circuit 12 by an inlet port 64 and two outlet ports 66 and 68. The inlet port 64 is shown as being associated with a bottom end or portion of the spinning membrane separator 26, while the outlet ports 66 and 68 are associated with an upper end or portion of the spinning membrane separator 26, but it is within the scope of the present disclosure for the spinning membrane separator 26 to be inverted, with fluid entering an upper end or portion of the spinning membrane separator 26 and fluid exiting a lower end or portion of the spinning membrane separator 26.

The illustrated spinning membrane separator 26 includes a generally cylindrical housing 70 mounted concentrically about a longitudinal vertical central axis. An internal member or rotor 72 is mounted concentrically with the central axis. The housing 70 and rotor 72 are relatively rotatable, as described above with respect to the spinning membrane separator drive unit 14. In a preferred embodiment, the housing 70 is stationary and the rotor 72 is a rotating spinner that is rotatable concentrically within the cylindrical housing 70. In such an embodiment, the housing 70 (or at least its upper and lower ends) are formed of non-magnetic material, while the rotor 72 includes an element (e.g., a metallic material) that interacts with a magnet of the spinning membrane separator drive unit 14 to rotate the rotor 72 within the housing 70, as described above.

The boundaries of the fluid flow path are generally defined by the gap 74 between the interior surface of the housing 70 and the exterior surface of the rotor 72, which is sometimes referred to as the shear gap. The width of the shear gap 74 may be of a uniform dimension along the axis, for example, where the axis of the housing 70 and rotor 72 are coincident. Alternatively, the width of the shear gap 74 also may vary along the axial direction, for example with the width of the gap 74 either increasing in the direction of flow to limit hemolysis or decreasing to increase shear in the gap 74. The gap width could change linearly or stepwise or in some other manner as may be desired. In any event, the width dimension of the gap 74 is preferably selected so that at the desired relative rotational speed, Taylor-Couette flow, such as Taylor vortices, are created in the gap 74 and hemolysis is limited.

Blood is fed into the gap 74 by the inlet port 64 (FIG. 8), which directs the blood into the fluid flow entrance region at or adjacent to the bottom end of the spinning membrane separator 26. The spinning membrane separator drive unit 14 causes relative rotation of the housing 70 and rotor 72, creating Taylor vortices within the gap 74. The outer surface of the rotor 72 and/or the inner surface of the housing 70 is at least partially (and more preferably, substantially or entirely) covered by a cylindrical, porous membrane 76 (shown in FIG. 9 as being mounted to the outer surface of the rotor 72). It should be, thus, understood that the term "spinning membrane separator" does not necessarily require that the membrane 76 is mounted to a component of the spinning membrane separator 26 that spins, but may also include a device in which the membrane 76 is mounted to a stationary component that includes another component that rotates with respect to the stationary membrane 76.

The membrane 76 has a nominal pore size and composition that may vary without departing from the scope of the present disclosure. However, in one embodiment, the membrane 76 is formed of a polycarbonate material and has a nominal pore size of approximately 0.8 microns, which serves to separate any platelets, red blood cells, or white blood cells from plasma, thus producing substantially cell-free plasma.

In an embodiment in which the rotor 72 spins within the housing 70 and the membrane 76 is mounted to the outer surface of the rotor 72, the outer surface of the rotor 72 may be shaped to define a series of spaced-apart circumferential grooves or ribs 78 separated by annular lands 80 (FIG. 9). The surface channels defined by the circumferential grooves 78 are interconnected by longitudinal grooves 82. At one or both ends of the rotor 72, these grooves 78 are in communication with a central orifice or manifold 84. Pumping fluid into and out of the spinning membrane separator 26 causes plasma to flow through the membrane 76 and grooves 78, while the cellular blood components remain within the gap 74 as fluid flows from the inlet port 64 at the bottom portion of the spinning membrane separator 26 toward the upper portion. Relative rotation of the rotor 72 and housing 70 causes a particular flow pattern within the gap 74 (described above) that enables filtration of the cellular blood components from the plasma without clogging the membrane 76.

At the upper portion of the spinning membrane separator 26, plasma exits the spinning membrane separator 26 via an outlet port 66 that is concentric with the rotational axis and in fluid communication with the central orifice 84 of the rotor 72 (FIG. 9), with the plasma flowing into a line associated with the outlet port 66. The separated cellular blood components in the gap 74 may be conveyed out of the gap 74 for collection or delivery to a recipient.

As described above, it may be advantageous to use differently sized spinning membrane separators 26 depending on the particular blood separation procedure being carried out. FIG. 8 shows a spinning membrane separator 26 having a rotor 72 with a spinner diameter D, a filtration length FL, and an overall length LOA. An exemplary smaller spinning membrane separator may have a spinner diameter D of approximately 1.1", a filtration length FL of approximately 3", and an overall length LOA of approximately 5.0". By comparison, an exemplary larger spinning membrane separator may have a spinner diameter D of approximately 1.65", a filtration length FL of approximately 5.52", and an overall length LOA of approximately 7.7". An exemplary smaller spinning membrane separator is described in greater detail in U.S. Pat. No. 5,194,145, while an exemplary larger spinning membrane separator is described in greater detail in U.S. Patent Application Publication No. 2015/0218517, which is incorporated herein by reference.

D. Centrifugal Separation Chamber

Figure 10:
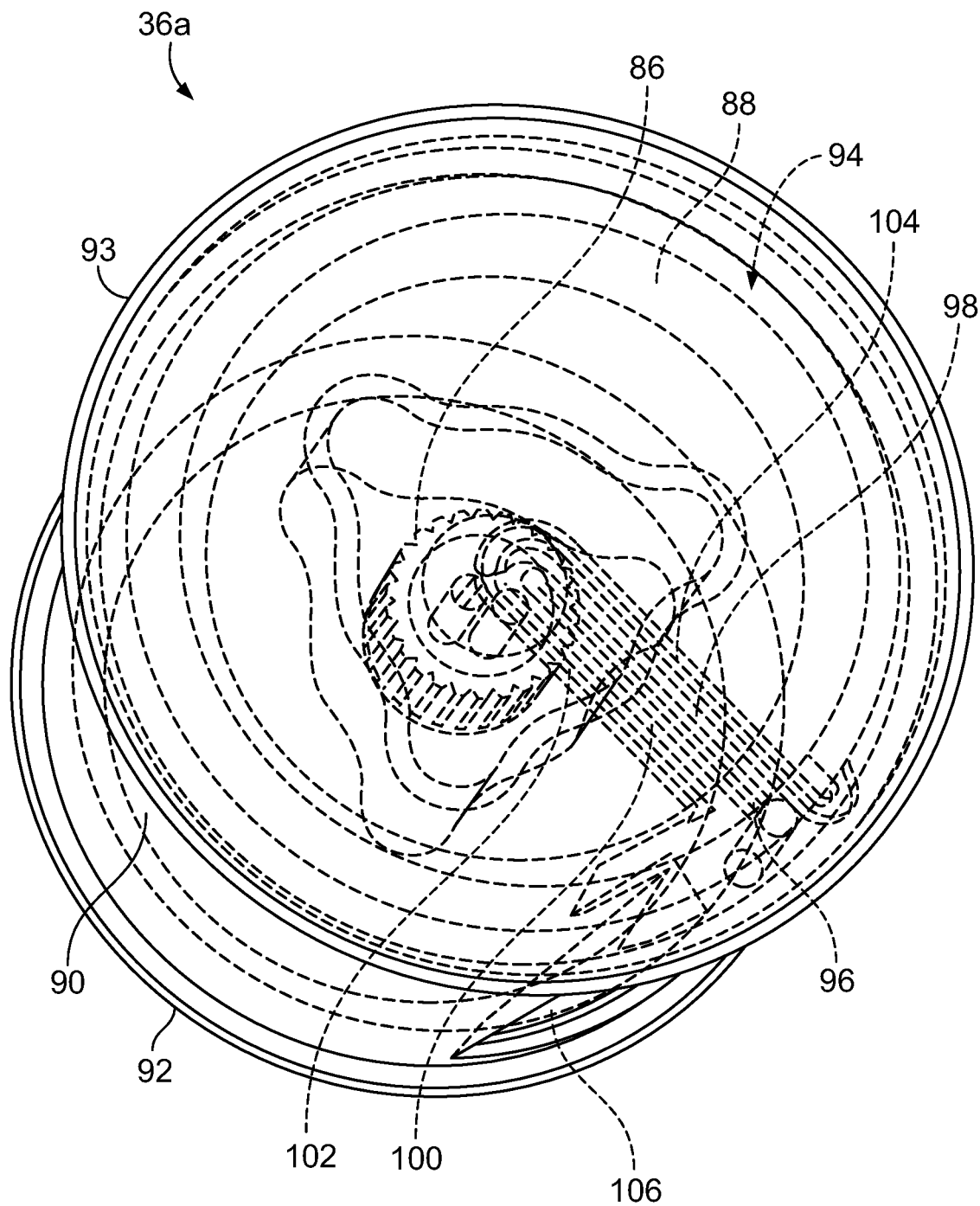
FIG. 10 is a perspective view of an exemplary centrifugal separation chamber of a fluid flow circuit.
Figure 11:
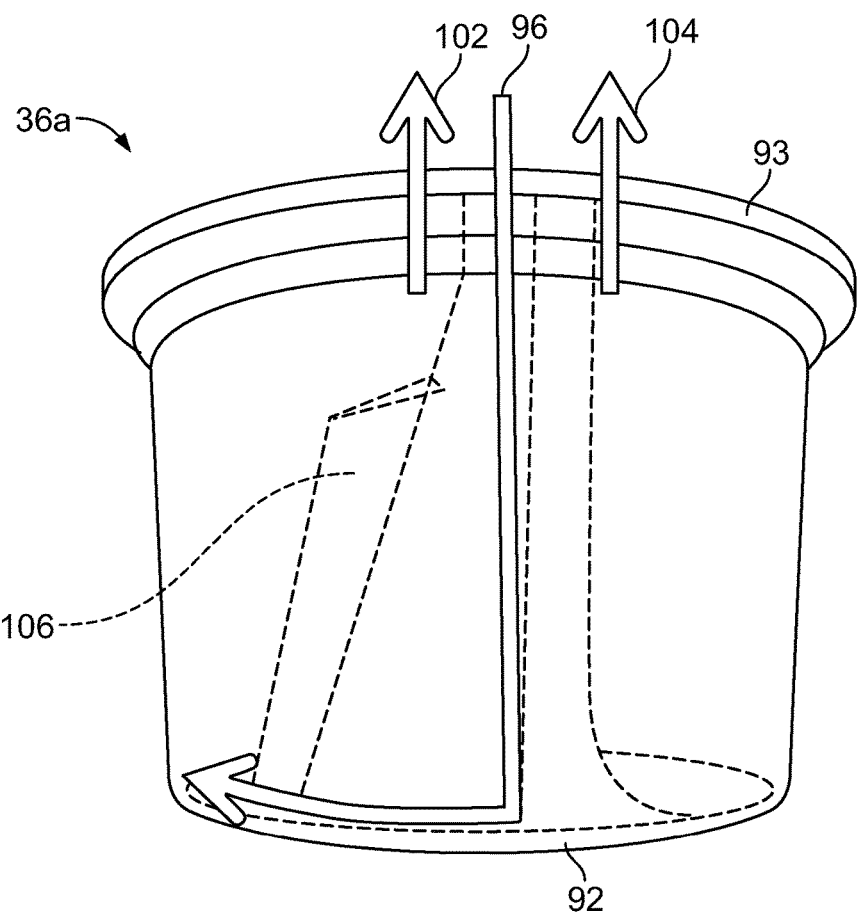
FIG. 11 is a front elevational view of the centrifugal separation chamber of FIG. 10.
Figure 12:
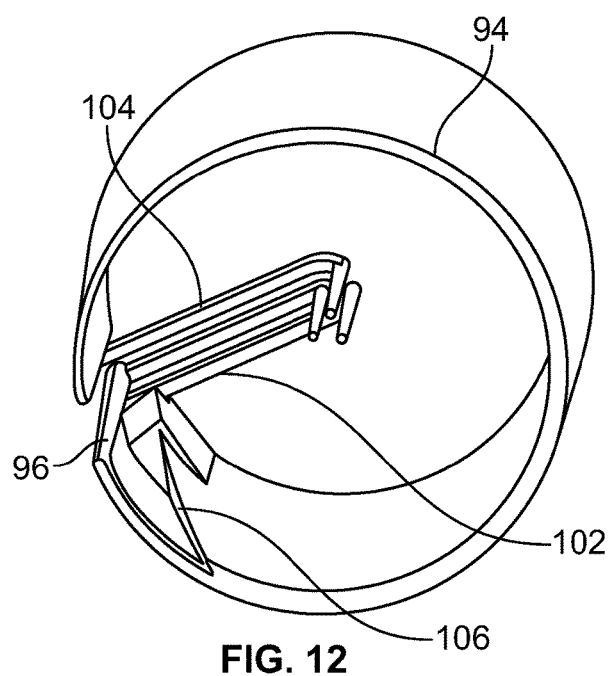
FIG. 12 is a bottom perspective view of the fluid flow path through the centrifugal separation chamber of FIG. 10.

A fluid flow circuit 12 may be provided with a centrifugal separation chamber 36, as in the embodiments of FIGS. 2C, 2D, 2G, and 2H. An exemplary centrifugal separation chamber 36a is shown in FIGS. 10 and 11, while FIG. 12 illustrates the fluid flow path defined by the centrifugal separation chamber 36a. In the illustrated embodiment, the body of the centrifugal separation chamber 36a is preformed in a desired shape and configuration (e.g., by injection molding) from a rigid, biocompatible plastic material, such as a non-plasticized medical grade acrylonitrile-butadiene-styrene (ABS). All contours, ports, channels, and walls that affect the blood separation process are preformed in a single, injection molded operation. Alternatively, the centrifugal separation chamber 36a can be formed by separate molded parts, either by nesting cup-shaped subassemblies or two symmetric halves.

The underside of the centrifugal separation chamber 36a includes a shaped receptacle 86 that is suitable for receiving an end of the umbilicus 46 of the fluid flow circuit 12 (FIG. 3). A suitable receptacle 86 and the manner in which the umbilicus 46 may cooperate with the receptacle 86 to deliver fluid to and remove fluid from the centrifugal separation chamber 36a are described in greater detail in U.S. Pat. No. 8,075,468.

The illustrated centrifugal separation chamber 36a has radially spaced apart inner (low-g) and outer (high-g) side wall portions 88 and 90, a bottom or first end wall portion 92, and a cover or second end wall portion 93. The cover 93 comprises a simple flat part that can be easily welded or otherwise secured to the body of the centrifugal separation chamber 36a. Because all features that affect the separation process are incorporated into one injection molded component, any tolerance differences between the cover 93 and the body of the centrifugal separation chamber 36a will not affect the separation efficiencies of the centrifugal separation chamber 36a. The wall portions 88 and 90, the bottom 92, and the cover 93 together define an enclosed, generally annular channel 94 (FIG. 12).

The (whole blood) inlet 96 communicating with the channel 94 is defined between opposing interior radial walls 98 and 100. One of the interior walls 98 joins the outer (high-g) wall portion 90 and separates the upstream and downstream ends of the channel 94. The interior walls 98 and 100 define the inlet passageway 96 of the centrifugal separation chamber 36a which, in one flow configuration, allows fluid to flow from the umbilicus 46 to the upstream end of the channel 94.

The illustrated centrifugal separation chamber 36a further includes first and second outlets 102 and 104, respectively, which may be defined by opposing surfaces of interior radial walls. Both the first and second outlets 102 and 104 extend radially inward from the channel 94. The first (plasma) outlet 102 extends radially inward from an opening which, in the illustrated embodiment, is located at the inner side wall portion 88, while the second (red blood cell) outlet 104 extends radially inward from an opening that is associated with the outer side wall portion 90. The illustrated first outlet 102 is positioned adjacent to the inlet 96 (near the upstream end of the channel 94), while the second outlet 104 may be positioned at the opposite, downstream end of the channel 94.

Figure 13:
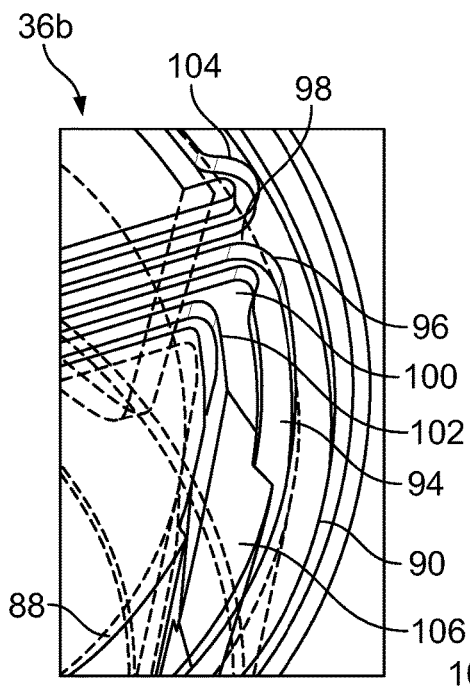
FIG. 13 is a perspective view of another embodiment of a centrifugal separation chamber of a fluid flow circuit.
Figure 14:
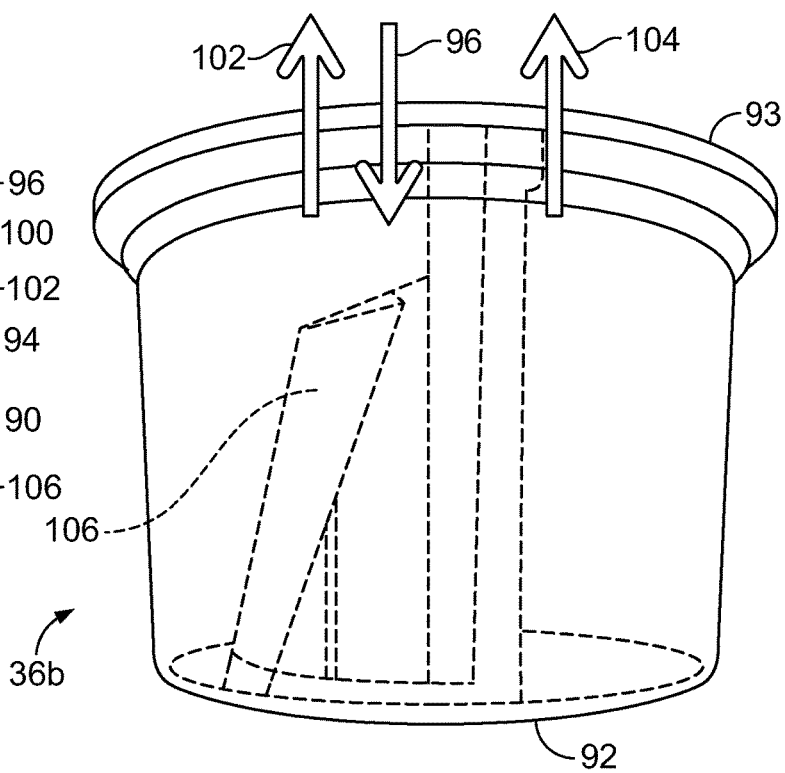
FIG. 14 is a front elevational view of the centrifugal separation chamber of FIG. 13.
Figure 15:
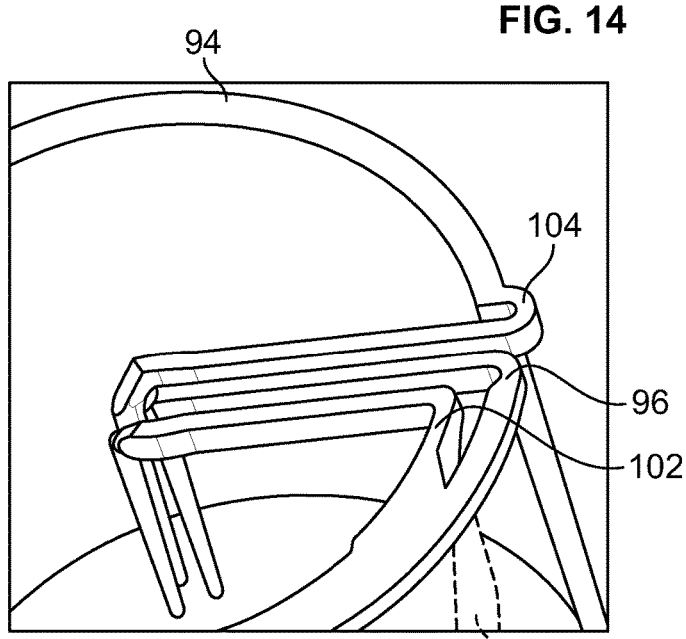
FIG. 15 is a top perspective view of the fluid flow path through the centrifugal separation chamber of FIG. 13.

It should be understood that the centrifugal separation chamber 36a illustrated in FIG. 10 is merely exemplary and that the centrifugal separation chamber 36 may be differently configured without departing from the scope of the present disclosure. For example, FIGS. 13 and 14 show an alternative embodiment of a centrifugal separation chamber 36b, while FIG. 15 illustrates the fluid flow path defined by the centrifugal separation chamber 36b. The centrifugal separation chamber 36b is similar to the centrifugal separation chamber 36a except for the location at which the inlet 96 opens into the channel 94. In the centrifugal separation chamber 36a of FIG. 10, the inlet 96 opens into the channel 94 adjacent to the first end wall portion 92 (while the outlets 102 and 104 open into the channel 94 adjacent to the second end wall portion 93), as best shown in FIGS. 11 and 12. In contrast, the inlet 96 of the centrifugal separation chamber 36b of FIG. 13 opens into the channel 94 adjacent to the second end wall portion 93 (along with the outlets 102 and 104), as best shown in FIGS. 14 and 15. The location at which the inlet 96 opens into the channel 94 may affect the separation of fluid within the channel 94, so the centrifugal separation chamber 36a of FIG. 10 may be preferable for certain procedures or for use in combination with certain blood separation devices, while the centrifugal separation chamber 36b of FIG. 13 may be preferable for other procedures or for use in combination with other blood separation devices.

Figure 16:
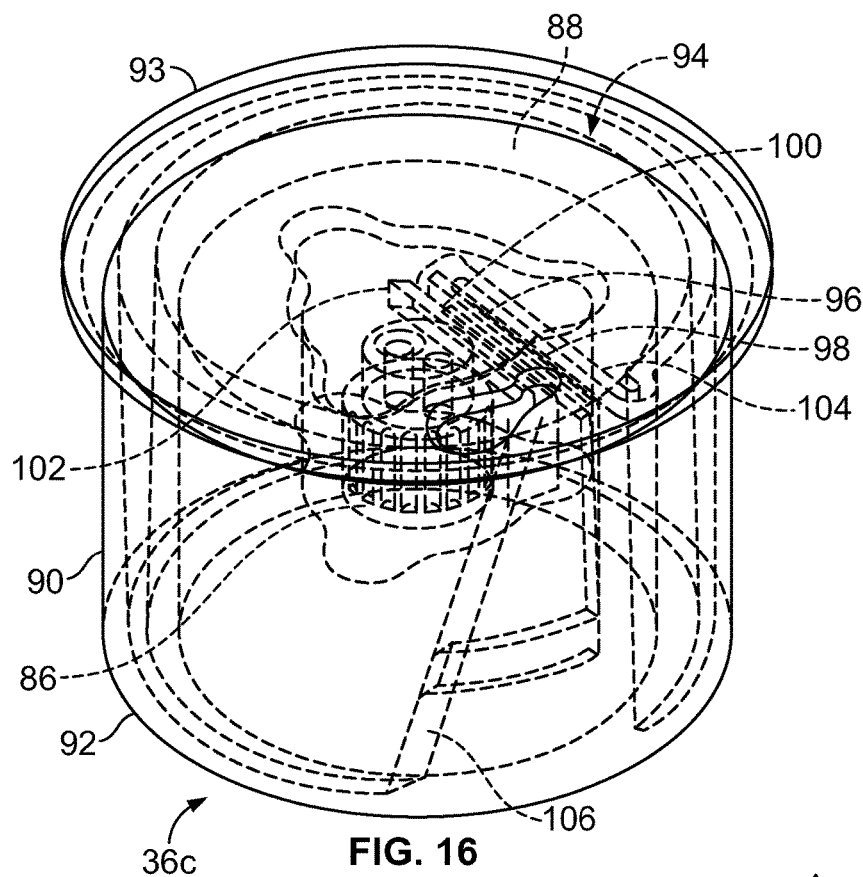
FIG. 16 is a perspective view of a third embodiment of a centrifugal separation chamber of a fluid flow circuit.
Figure 17:
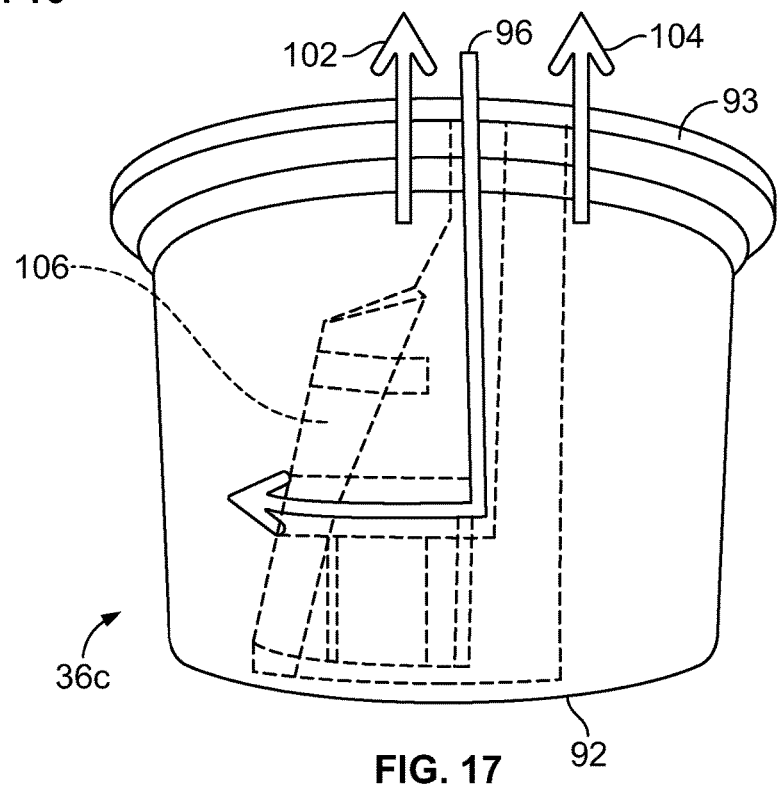
FIG. 17 is a front elevational view of the centrifugal separation chamber of FIG. 16.

FIGS. 16 and 17 show another exemplary embodiment of a centrifugal separation chamber 36c suitable for incorporation into a fluid flow circuit 12. The centrifugal separation chamber 36c is similar to the centrifugal separation chambers 36a and 36b of FIGS. 10 and 13 except for the location at which the inlet 96 opens into the channel 94. In contrast to the inlets 96 of the centrifugal separation chambers 36a and 36b of FIGS. 10 and 13, the inlet 96 of the centrifugal separation chamber 36c of FIG. 16 opens into the channel 94 at an intermediate axial location that is spaced from the first and second end wall portion 92 and 93 (while the outlets 102 and 104 open into the channel adjacent to the second end wall portion 93), as best shown in FIG. 17. The inlet 96 may open into the channel 94 at a location that is closer to the first end wall portion 92 than to the second end wall portion 93, at a location that is closer to the second end wall portion 93 than to the first end wall portion 92, or at a location that is equally spaced between the first and second end wall portions 92 and 93. The axial location at which the inlet 96 opens into the channel 94 may affect the separation of fluid within the channel 94, so the preferred location at which the inlet 96 opens into the channel 94 (which may also depend upon the nature of the blood separation device paired with the centrifugal separation chamber 36c) may be experimentally determined.

1. Centrifugal Separation and Interface Detection Principles

Blood flowed into the channel 94 separates into an optically dense layer RBC and a less optically dense layer PLS (FIGS. 18-20) as the centrifugal separation chamber 36 is rotated about the rotational axis 38. The optically dense layer RBC forms as larger and/or heavier blood particles move under the influence of centrifugal force toward the outer (high-g) wall portion 90. The optically dense layer RBC will typically include red blood cells (and, hence, may be referred to herein as the "RBC layer") but, depending on the speed at which the centrifugal separation chamber 36 is rotated, other cellular components (e.g., larger white blood cells) may also be present in the optically dense layer RBC.

The less optically dense layer PLS typically includes a plasma constituent, such as platelet-rich plasma (and, hence, will be referred to herein as the "PLS layer"). Depending on the speed at which the centrifugal separation chamber 36 is rotated and the length of time that the blood is resident therein, other components (e.g., smaller white blood cells and anticoagulant) may also be present in the less optically dense layer PLS.

In one embodiment, blood introduced into the channel 94 via the inlet 96 will travel in a generally clockwise direction (in the orientation of FIG. 10) as the optically dense layer RBC separates from the less optically dense layer PLS. The optically dense layer RBC continues moving in the clockwise direction as it travels the length of the channel 94 along the outer side wall portion 90, from the upstream end to the downstream end, where it exits the channel 94 via the second outlet 104. The less optically dense layer PLS separated from the optically dense layer RBC reverses direction, moving counterclockwise along the inner side wall portion 88 to the first outlet 102, adjacent to the inlet 96. The inner side wall portion 88 may be tapered inward as it approaches the second outlet 104 to force the plasma liberated at or adjacent to the downstream end of the channel 94 to drag the interface back towards the upstream end of the channel 94, where the lower surface hematocrit will re-suspend any platelets settled on the interface.

Figure 18:
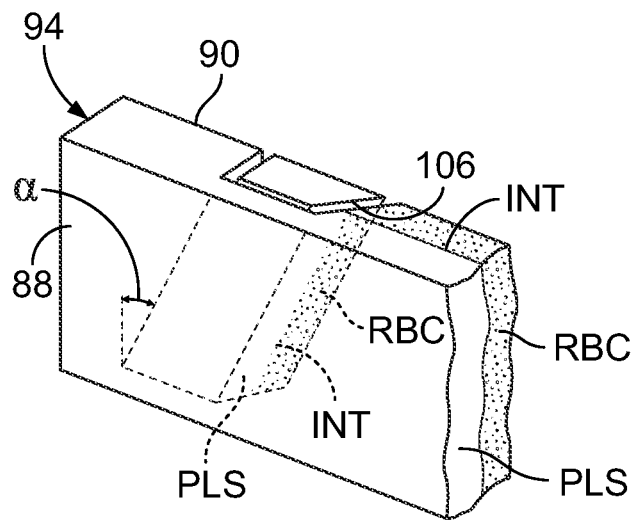
FIG. 18 is an enlarged perspective view of a portion of a channel of any of the centrifugal separation chambers of FIGS. 10-17, with an interface between separated blood components being positioned at a (typically) desired location on a ramp defined within the channel.
Figure 19:
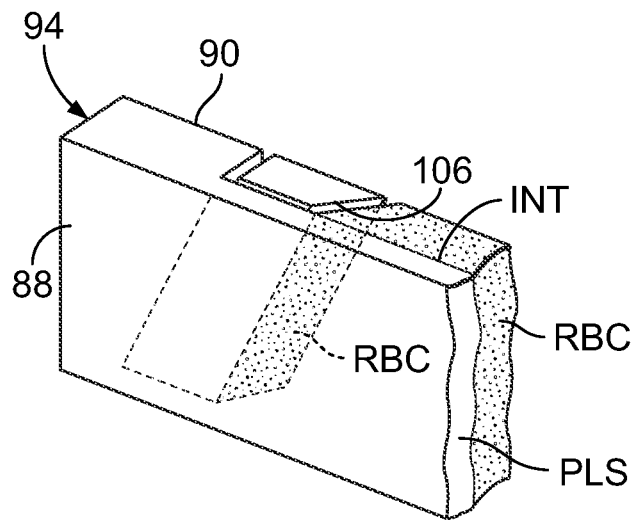
FIG. 19 is an enlarged perspective view of the channel and ramp of FIG. 18, with the interface being at a (typically) undesired high location on the ramp.
Figure 20:
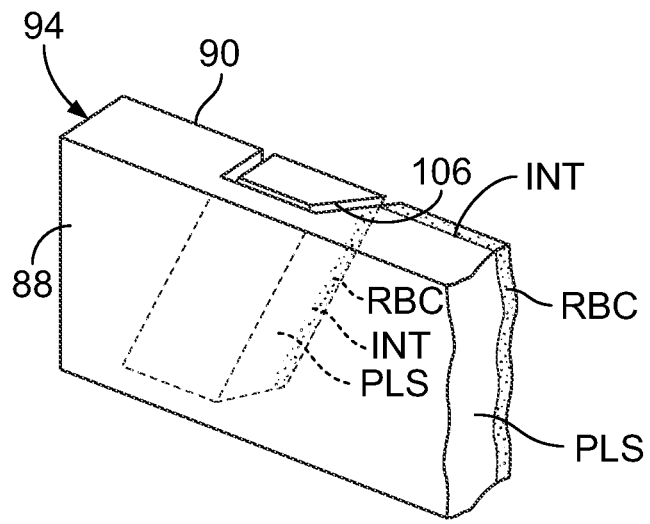
FIG. 20 is an enlarged perspective view of the channel and ramp of FIG. 18, with the interface being at a (typically) undesired low location on the ramp.

As described above, the transition between the optically dense layer RBC and the less optically dense layer PLS may be referred to as the interface INT. The location of the interface INT within the channel 94 of the centrifugal separation chamber 36 can dynamically shift during blood processing, as FIGS. 18-20 show. If the location of the interface INT is too high (that is, if it is too close to the inner side wall portion 88 and the first outlet 102, as in FIG. 19), red blood cells can flow into the first outlet 102, potentially adversely affecting the quality of the low density components (platelet-rich plasma). On the other hand, if the location of the interface INT is too low (that is, if it resides too far away from the inner wall portion 88, as FIG. 20 shows), the collection efficiency of the system may be impaired. The ideal or target interface INT may be experimentally determined, which may vary depending on any of a number of factors (e.g., the configuration of the centrifugal separation chamber 36, the rate at which the centrifugal separation chamber 36 is rotated about the rotational axis 38, etc.).

As described above, the blood separation device 10 may include an interface monitoring system and a controller 18 with an interface control module to monitor and, as necessary, correct the position of the interface INT. In one embodiment, the centrifugal separation chamber 36 is formed with a ramp 106 extending from the high-g wall portion 90 at an angle α across at least a portion of the channel 94 (FIGS. 10 and 18-20). The angle α, measured with respect to the rotational axis 38 is about 25° in one embodiment. FIGS. 18-20 show the orientation of the ramp 106 when viewed from the low-g side wall portion 88 of the centrifugal separation chamber 36. Although it describes a flexible separation chamber, the general structure and function of the ramp 106 may be better understood with reference to U.S. Pat. No. 5,632,893, which is incorporated herein by reference. The ramp 106 may be positioned at any of a number of locations between the upstream and downstream ends of the channel 94, but in one embodiment, the ramp 106 may be positioned generally adjacent to the first outlet 102, in the path of fluid and/or a fluid component moving from the inlet 96 to the first outlet 102.

The ramp 106 makes the interface INT between the optically dense layer RBC and the less optically dense layer PLS more discernible for detection, displaying the optically dense layer RBC, less optically dense layer PLS, and interface INT for viewing through a light-transmissive portion of the centrifugal separation chamber 36. To that end, the ramp 106 and at least the portion of the centrifugal separation chamber 36 angularly aligned with the ramp 106 may be formed of a light-transmissive material, although it may be advantageous for the entire centrifugal separation chamber 36 to be formed of the same light-transmissive material.

In the illustrated embodiment, the light source 50 of the interface monitoring system is secured to a fixture or wall of the centrifuge compartment 32 and oriented to emit a light that is directed toward the rotational axis 38 of the centrifugal separator 16, as shown in FIGS. 5-7. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 88, as shown in FIGS. 5 and 6. The reflector may be a separate piece that is secured to the inner side wall portion 88 (e.g., by being bonded thereto) or may be integrally formed with the body of the centrifugal separation chamber 36.

Figure 21:
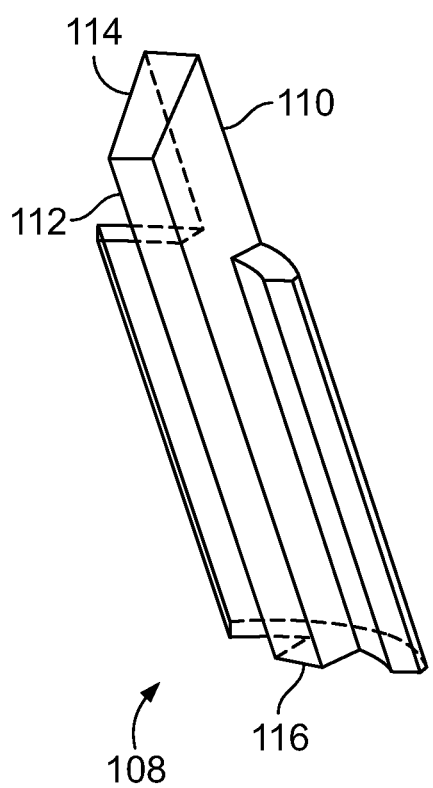
FIG. 21 is a perspective view of a prismatic reflector used in combination with any of the centrifugal separation chambers of FIGS. 10-17.

In one embodiment, the reflector may be a reflective surface, such as a mirror, that is oriented (e.g., at a 45° angle) to direct light L emitted by the light source 50 to the light detector 52. In another embodiment, the reflector is provided as a prismatic reflector 108 (FIGS. 7, 21, and 22), which is formed of a light-transmissive material (e.g., a clear plastic material) and has inner and outer walls 110 and 112 and first and second end walls 114 and 116 (FIG. 21). The inner wall 110 is positioned against the inner side wall portion 88 of the centrifugal separation chamber 36 and is oriented substantially perpendicular to the initial path of the light L from the light source 50. This allows light L from the light source 50 to enter into the prismatic reflector 108 via the inner wall 110 while continuing along its initial path. The light L continues through the prismatic reflector 108 along its initial path until it encounters the first end wall 114. The first end wall 114 is oriented at an angle (e.g., an approximately 45° angle) with respect to the first surface 110 and the second end wall 116, causing the light to be redirected within the prismatic reflector 108, rather than exiting the prismatic reflector 108 via the first end wall 114.

Figure 22:
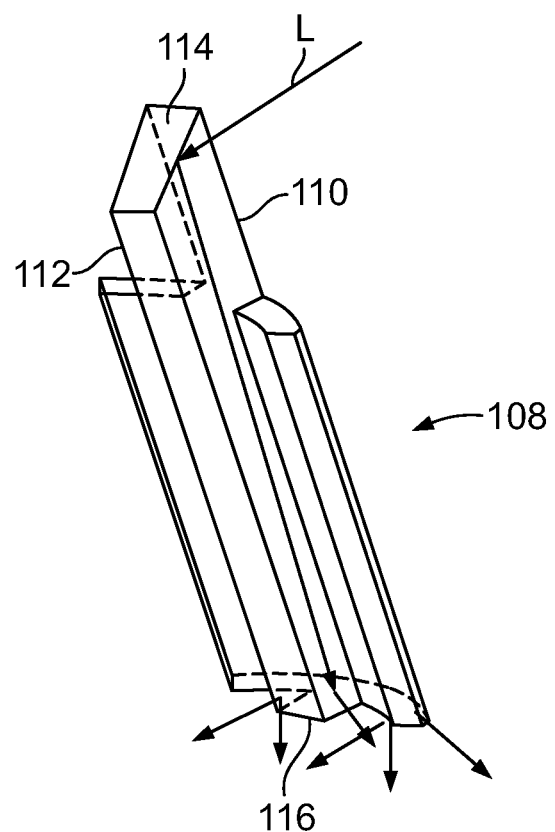
FIG. 22 is a perspective view of the prismatic reflector of FIG. 21, showing light being transmitted therethrough.

The first end wall 114 directs the light L at an angle to its initial path (which may be an approximately 90° angle, directing it from a path toward the rotational axis 38 to a path that is generally parallel to the rotational axis 38) toward the second end wall 116 (FIG. 22). The first end wall 114 and the inner and outer walls 110 and 112 of the prismatic reflector 108 may be configured to transmit the redirected light L from the first end wall 114 to the second end wall 116 by total internal reflection. The second end wall 116 is oriented substantially perpendicular to the redirected path of the light L through the prismatic reflector 108, such that the light L will exit the prismatic reflector 108 via the second end wall 116, continuing along its redirected path. In one embodiment, the second end wall 116 is roughened or textured or otherwise treated or conditioned to diffuse the light L as it exits the prismatic reflector 108, which may better ensure that the light L reaches the light detector 52 (FIG. 7).

Figure 23:
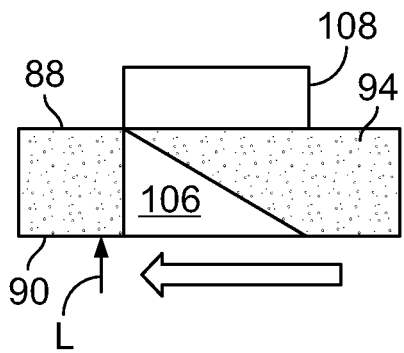
FIGS. 23-26 are diagrammatic views of the ramp and prismatic reflector of the centrifugal separation chamber passing through the path of light from the light source during a calibration phase.
Figure 27:
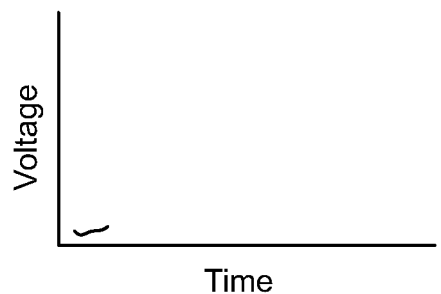
FIGS. 27-30 are diagrammatic views of the voltage output or signal transmitted by the light detector during the conditions shown in FIGS. 23-26, respectively.
Figure 24:
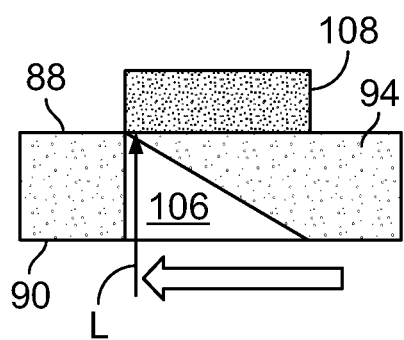

The prismatic reflector 108 may be angularly aligned with the ramp 106, such that the light L from the light source 50 will only enter into the prismatic reflector 108 when the ramp 106 has been rotated into the path of the light L. At all other times (when the ramp 106 is not in the path of the light L), the light L will not reach the prismatic reflector 108 and, thus, will not reach the light detector 52. This is illustrated in FIGS. 23-26, which show the ramp 106 and prismatic reflector 108 as the centrifugal separation chamber 36 is rotated about the rotational axis 38 (while the light source 50 remains in a fixed location). In FIG. 23, the ramp 106 and prismatic reflector 108 have not yet been rotated into the initial path of the light L from the light source 50. At this time, no light is transmitted to the light detector 52, such that the output voltage of the light detector 52 (i.e., the signal transmitted from the light detector 52 to the controller 18) is in a low- or zero-state (FIG. 27).

Figure 28:
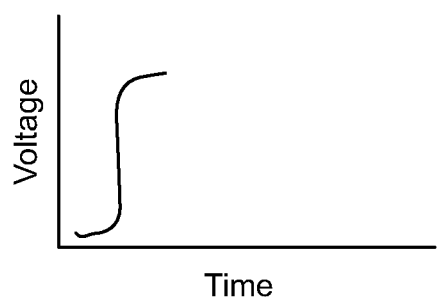

Upon the ramp 106 first being rotated into the initial path of the light L from the light source 50 (FIG. 24), the light L will begin to reach the prismatic reflector 108, which directs the light L to the light detector 52. This causes the voltage output of the light detector 52 (i.e., the signal transmitted from the light detector 52 to the controller 18) to increase to a non-zero value or state, as shown in FIG. 28.

Figure 25:
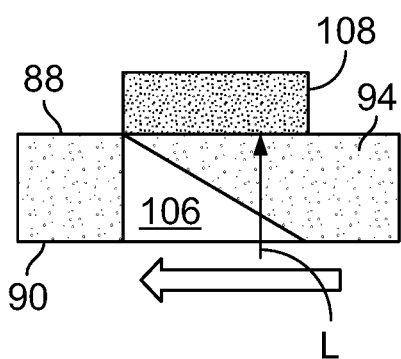
Figure 29:
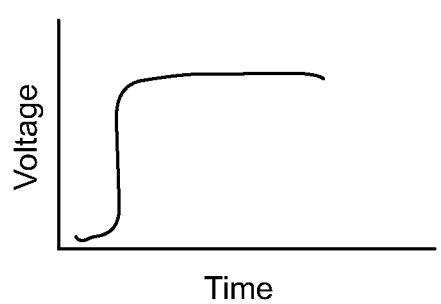
Figure 26:
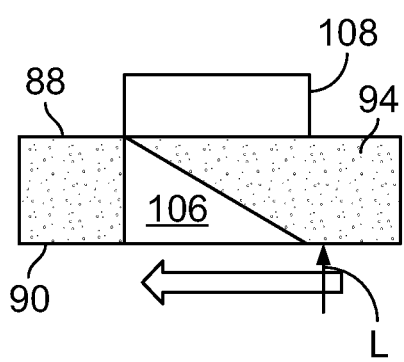

During a calibration phase, the channel 94 is filled with a fluid that will transmit the light L rather than absorbing or reflecting the light or otherwise preventing the light L from reaching the prismatic reflector 108, such that the voltage output of the light detector 52 will remain generally constant as the ramp 106 and prismatic reflector 108 are rotated through the initial path of the light L from the light source 50 (FIGS. 25 and 29). Such a calibration phase may coincide with a priming phase during which saline is pumped through the fluid flow circuit 12 to prime the fluid flow circuit 12 or may comprise a separate phase. A calibration phase may be useful in ensuring the proper operation of the light source 50 and the light detector 52, standardizing the readings taken during a separation procedure in case of any irregularities or imperfections of the centrifugal separation chamber 36, and establishing a baseline value for the signal transmitted from the light detector 52 to the controller 18 when the ramp 106 and prismatic reflector 108 are aligned with the light source 50. As will be described in greater detail, the voltage output of the light detector 52 will typically not remain constant as the ramp 106 and prismatic reflector 108 are rotated through the initial path of the light L from the light source 50 because the different fluid layers displayed on the ramp 106 will allow different amounts of light L to reach the prismatic reflector 108.

Figure 30:
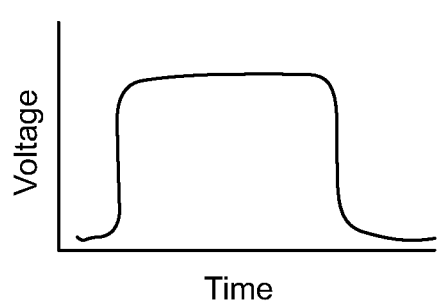
Figure 31:
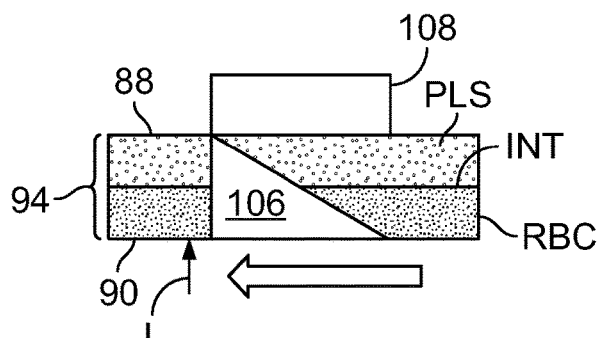
FIGS. 31-34 are diagrammatic views of the ramp and prismatic reflector passing through the path of light from the light source during a separation procedure.

The ramp 106 and prismatic reflector 108 are eventually rotated out of alignment with the light source 50 (FIG. 26), at which time no light L will reach the prismatic reflector 108 and the voltage output of the light detector 52 will return to its low- or zero-state (FIG. 30).

It may be advantageous for the light L to have a relatively small diameter for improved resolution of the signal that is generated by the light detector 52.

2. Exemplary Interface Detection and Correction Procedure

During separation of blood within the channel 94, the light L from the light source 50 travels through a light-transmissive portion of the outer side wall portion 90 and the ramp 106 to intersect the separated blood components thereon when the ramp 106 has been rotated into the initial path of the light L. After passing through the ramp 106, the light continues through the channel 94 and the fluids in the channel 94. At least a portion of the light L (i.e., the portion not absorbed or reflected by the fluids) exits the channel 94 by striking and entering a light-transmissive portion of the inner side wall portion 88. The light L passes through the inner side wall portion 88 and enters the prismatic reflector 108, which redirects the light L from its initial path to the light detector 50, as described above. Thus, it will be seen that the light L reaches the light detector 52 after intersecting and traveling through the separated blood components in the channel 94 only once, in contrast to conventional systems in which light from a light source travels through a ramp and a fluid-filled channel before being reflected back through the channel to reach a light detector. Requiring the light L to traverse the fluid-filled channel 94 only once before reaching the light detector 52 instead of twice may be advantageous in that it tends to increase the intensity of the light L that reaches the light detector 52, which may improve monitoring and correction of the interface location.

The light detector 52 generates a signal that is transmitted to the interface control module of the controller 18, which can determine the location of the interface INT on the ramp 106. In one embodiment, the location of the interface INT is associated with a change in the amount of light L that is transmitted through the less optically dense layer PLS and the optically dense layer RBC. For example, the light source 50 may be configured to emit a light L that is more readily transmitted by platelet-rich plasma than by red blood cells, such as red visible light (from a laser or a differently configured light source 50), which is substantially absorbed by red blood cells. The less optically dense layer PLS and the optically dense layer RBC each occupy a certain portion of the ramp 106, with the light detector 52 receiving different amounts of light L depending on whether the light L travels through the less optically dense layer PLS on the ramp 106 or the optically dense layer RBC on the ramp 106. The percentage of the ramp 106 occupied by each layer is related to the location of the interface INT in the channel 94. Thus, by measuring the amount of time that the voltage output or signal from the light detector 52 is relatively high (corresponding to the time during which the light L is passing through only the less optically dense layer PLS on the ramp 106), the controller 18 may determine the location of the interface INT and take steps to correct the location of the interface INT, if necessary.

Figure 32:
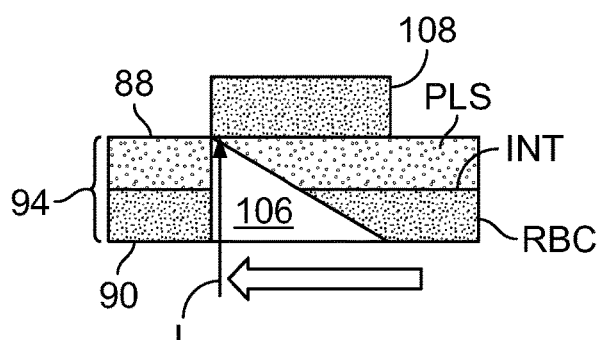
Figure 33:
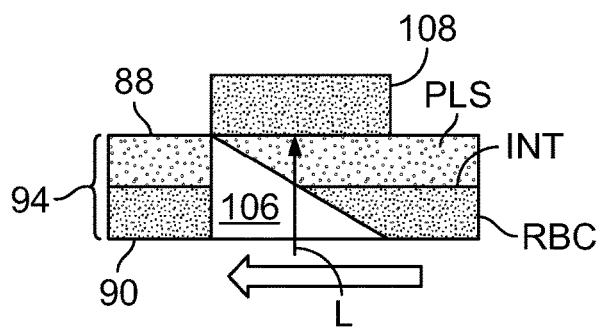
Figure 34:
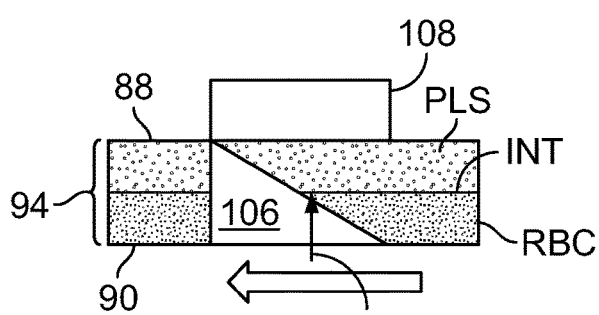

FIGS. 31-34 show a portion of the ramp 106 being rotated into and through the initial path of the light L from the light source 50. Four specific events are shown: just before the ramp 106 is rotated into the path of the light L (FIG. 31), the ramp 106 first being rotated into the path of the light L (FIG. 32), just before the interface INT displayed on the ramp 106 is rotated into the path of the light L (FIG. 33), and just after the interface INT is rotated into the path of the light L (FIG. 34). FIGS. 35-38 respectively illustrate the voltage output of the light detector 52 (corresponding to the signal that it transmits to the controller 18) during each of these events.

Figure 35:
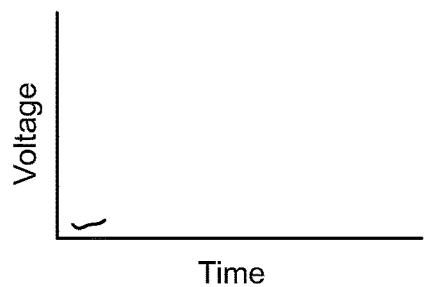
FIGS. 35-38 are diagrammatic views of the voltage output or signal transmitted by the light detector during the conditions shown in FIGS. 31-34, respectively.

As described above, the light detector 52 will receive no light L from the light source 50 when the prismatic reflector 108 is out of alignment with the initial path of the light L from the light source 50, as shown in FIG. 29. FIG. 35 shows that the output voltage of the light detector 52 (i.e., the signal transmitted from the light detector 52) to the controller 18) at this time is in a low- or zero-state.

When the ramp 106 is first rotated into the path of light L from the light source 50 (FIG. 32), the light detector 52 may begin receiving light L. The amount of light L received by the light detector 52 depends upon the fluid on the ramp 106 encountered by the light L (i.e., the fluid in the channel 94 between the ramp 106 and the inner side wall portion 88 that the light L must traverse before being directed to the light detector 52). As described above, the less optically dense layer PLS occupies a certain percentage of the channel 94 adjacent to the inner side wall portion 88, while the optically dense layer RBC occupies a certain percentage of the channel 94 adjacent to the outer side wall portion 90 (with the interface INT positioned at the transition between the two separated blood component layers). The illustrated ramp 106 is closest to the inner side wall portion 88 at its left end (in the orientation of FIGS. 31-34), while being farther spaced from the inner side wall portion 88 at its right end. At and adjacent to its left end, the ramp 106 will display only the fluid positioned closest to the inner side wall portion 88 (i.e., the less optically dense layer PLS), while the ramp 106 will display only the fluid positioned closest to the outer side wall portion 90 (i.e., the optically dense layer RBC) at and adjacent to its right end, as shown in FIGS. 31-34. At some point between its ends, the angled ramp 106 will be at a radial position where it will display the transition between the less optically dense layer PLS and the optically dense layer RBC (i.e., the interface INT). Hence, the location of the interface INT on the ramp 106 is dependent upon the percentage of the width of the ramp 106 that displays the less optically dense layer PLS (which is indicative of the percentage of the channel 94 occupied by the less optically dense layer PLS) and the percentage of the width of the ramp 106 that displays the optically dense layer RBC (which is indicative of the percentage of the channel 94 occupied by the optically dense layer RBC). It should be understood that the percentage of the ramp 106 occupied by the less optically dense layer PLS and by the optically dense layer RBC is not necessarily equal to the percentage of the channel 94 occupied by the less optically dense layer PLS and by the optically dense layer RBC, but that the percentage of the ramp 106 occupied by a separated blood component layer may be merely indicative of the percentage of the channel 94 occupied by that separated blood component layer.

Figure 36:
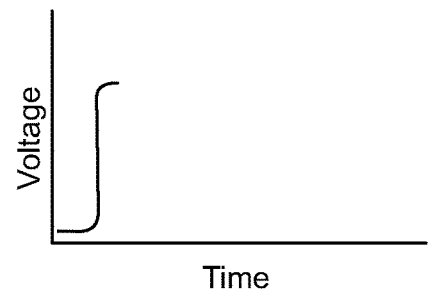

In such an embodiment, as the ramp 106 is rotated into the path of the light L from the light source 50, the light L will first encounter the portion of the ramp 106 that is positioned closest to the inner side wall portion 88 (i.e., the section of the ramp 106 that most restricts the channel 94), as shown in FIG. 32. As described above, the less optically dense layer PLS will be positioned adjacent to the inner side wall portion 88 as it separates from the optically dense layer RBC, such that the fluid displayed on this radially innermost section of the ramp 106 (i.e., the fluid present in the channel 94 between the ramp 106 and the inner side wall portion 88) will be the less optically dense layer PLS. The light is substantially transmitted through the less optically dense layer PLS to the inner side wall portion 88, and through the light-transmissive inner side wall portion 88 to the prismatic reflector 108, which redirects the light L to the light detector 52. This causes the voltage output of the light detector 52 (i.e., the signal transmitted from the light detector 52 to the controller 18) to increase to a non-zero value or state, as shown in FIG. 36. Depending on the nature of the light L, the amount of light L received by the light detector 52 (and, hence, the magnitude of the voltage output) after the light L has passed through the less optically dense layer PLS may be greater than, less than, or equal to the amount of light L received by the light detector 52 after passing through saline during the calibration phase described above.

Figure 37:
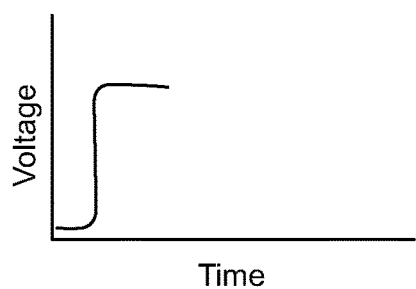

Further rotation of the ramp 106 through the path of light L from the light source 50 exposes the light L to portions of the ramp 106 that are increasingly spaced from the inner side wall portion 88 (i.e., the light L travels through portions of the channel 94 that are less restricted by the ramp 106 as the ramp 106 is rotated through the path of the light L). Up until the time that the interface INT on the ramp 106 is rotated into the path of the light L (as shown in FIG. 33), the only fluid in the channel 94 that the light L will have passed through will be the less optically dense layer PLS, such that a generally uniform level of light reaches the light detector 52 between the conditions shown in FIGS. 32 and 33. Accordingly, the voltage output of the light detector 52 will be generally uniform (at an elevated level) the whole time that the ramp 106 passes through the path of the light L before being exposed to the interface INT, as shown in FIG. 37. The controller 18 may be programmed and/or configured to consider a signal that deviates from a maximum signal level (e.g., a 10% decrease) to be part of the elevated signal for purposes of calculating the pulse width of the signal. The controller 18 will treat a greater deviation (i.e., a greater decrease in the magnitude of the signal) as the end of the elevated signal for purposes of calculating the pulse width of the signal.

Just after the interface INT has been rotated into the path of light L from the light source 50, the light L will begin to encounter the optically dense layer RBC in the channel 94, as shown in FIG. 34). As described above, the optically dense layer RBC will be positioned adjacent to the outer side wall portion 90 as it separates from the less optically dense layer PLS, such that the optically dense layer RBC will not be displayed on the ramp 106 until the ramp 106 is spaced a greater distance away from the inner side wall portion 88 (i.e., toward the right end of the ramp 106 in the orientation of FIGS. 31-34). Less light L is transmitted through the optically dense layer RBC than through the less optically dense layer PLS (which may include all or substantially all of the light L being absorbed by the optically dense layer RBC), such that the amount of light L that reaches the light detector 52 will decrease compared to the amount of light L that reaches the light detector 52 while traveling through only the less optically dense layer PLS in the channel 94 (FIGS. 32 and 33).

Figure 38:
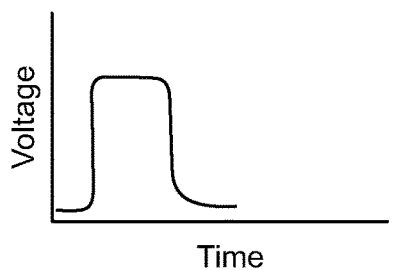

When receiving less light L, the voltage output or signal from the light detector 52 will decrease to a lower level than when the light L was passing through only the less optically dense layer PLS in the channel 94, as shown in FIG. 38. When the light L encounters the optically dense layer RBC in the channel 94, the light detector 52 may be generating a signal or voltage output that is approximately equal to its zero-state (as in FIG. 35, when the light detector 52 is receiving no light L) or a signal or voltage output that is some degree less than the magnitude of the signal or voltage output generated while the light L encounters only the less optically dense layer PLS in the channel 94. The controller 18 may be programmed and/or configured to recognize this lower level signal as representing the presence of the optically dense layer RBC on the ramp 106 (and in the portion of the channel 94 being traversed by the light L) and treat this lower level signal as the end point of the elevated signal generated by the light detector 52 while light L passes through only the less optically dense layer PLS in the channel 94.

Figure 39:
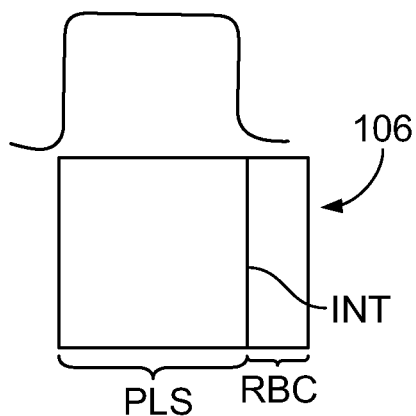
FIGS. 39 and 40 are diagrammatic views of separated blood components on the ramp and the pulse widths of a signal generated by the light detector for each condition.
Figure 40:
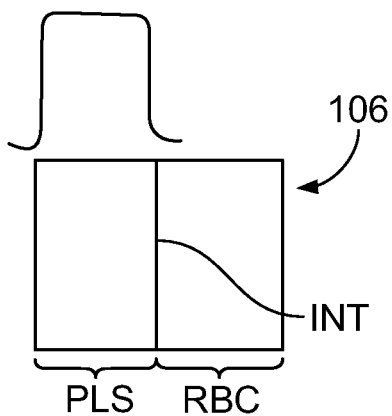
Figure 41:
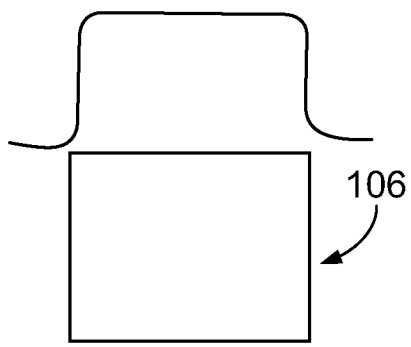
FIG. 41 is a diagrammatic view of saline on the ramp and the pulse width of a signal generated by the light detector for such a condition.

Thus, the pulse width of the elevated signal from the light detector 52 to the controller 18 (i.e., the time during which light L is traversing only the less optically dense layer PLS in the channel 94) is determined by the percentages of the ramp 106 that are occupied by the less optically dense layer PLS and the optically dense layer RBC. Accordingly, a greater pulse width of the signal from the light detector 52 to the controller 18 is associated with the less optically dense layer PLS occupying a larger portion of the ramp 106 (as shown in FIG. 39 from the point of view of the light source 50, which may correspond to the condition shown in FIG. 19) and will be indicative of a thinner optically dense layer RBC on the ramp 106 (and in the channel 94). Conversely, a signal from the light detector 52 to the controller 18 having a narrower pulse width is associated with the less optically dense layer PLS occupying a smaller portion of the ramp 106 (as shown in FIG. 40) and will be indicative of a thicker optically dense layer RBC on the ramp 106 (and in the channel 94).

The controller 18 may compare the pulse width of the signal to the pulse width generated during the calibration phase (described above and shown in FIG. 41), which corresponds to the pulse width when light L is transmitted to the light detector 52 over the entire width of the ramp 106. The pulse width of the signal generated by the light detector 52 during the calibration phase may be referred to as the saline calibration signal. Comparing these two pulse widths will indicate the percentage of the ramp 106 that is occupied by the less optically dense layer PLS and by the optically dense layer RBC, which information the controller 18 may use to determine the location of the interface INT within the channel 94. In particular, the interface position may be calculated as follows:

$$\text{Interface position (\%)} = ((\text{saline calibration pulse width} - \text{current plasma pulse width})/\text{saline calibration pulse width}) \times 100 \quad \text{[Equation 1]}$$

It will be seen that Equation 1 effectively calculates the percentage of the ramp 106 that is occupied by the optically dense layer RBC, as the difference between the two pulse widths corresponds to the length of time that the ramp 106 is rotated through the path of the light L without the light detector 52 received an elevated level of light L (i.e., the amount of time that the ramp 106 is rotated through the path of the light L while the optically dense layer RBC is present on the ramp 106).

Figure 42:
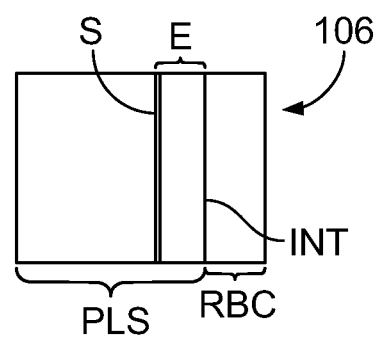
FIG. 42 is a diagrammatic view of the position of an interface between separated blood components on the ramp compared to a target interface position.

When the location of the interface INT on the ramp 106 has been determined, the interface control module compares the actual interface location with a desired interface location, which may be referred to as the setpoint S. The difference between the setpoint S and the calculated interface position may be referred to as the error signal E, which is shown in FIG. 42. It should be understood that so expressing the error signal E in terms of a targeted red blood cell percentage value (i.e., the percentage of the ramp 106 that is actually occupied by the optically dense layer RBC vs. the percentage of the ramp 106 which should be occupied by the optically dense layer RBC) is merely exemplary, and that the error signal E may be expressed or calculated in any of a number of other ways.

When the control value is expressed in terms of a targeted red blood cell percentage value, a negative error signal E indicates that the optically dense layer RBC on the ramp 106 is too large (as FIG. 19 shows). The interface control module of the controller 18 generates a signal to adjust an operational parameter accordingly, such as by reducing the rate at which the plasma constituent is removed through the first outlet 102 under action of a pump of the blood separation device 10. The interface INT moves toward the desired control position (as FIG. 18 shows), where the error signal is zero.

A positive error signal indicates that the optically dense layer RBC on the ramp 106 is too small (as FIGS. 20 and 42 show). The interface control module of the controller 18 generates a signal to adjust an operational parameter accordingly, such as by increasing the rate at which the plasma constituent is removed through the first outlet 102 under action of a pump of the blood separation device 10. The interface INT moves toward the desired control position (FIG. 18), where the error signal is again zero.

It should be understood that this system for controlling the location of the interface INT is merely exemplary and that differently configured and/or functioning systems may be employed without departing from the scope of the present disclosure.

III. Exemplary Separation Procedures

Exemplary blood separation procedures that may be carried out using systems and techniques according to the present disclosure will now be described.

Depending on the blood separation objectives, there is a suitable procedure for separating and collecting any of a variety of different blood components, either alone or in combination with other blood components. Accordingly, prior to processing, an operator selects the desired protocol (e.g., using an operator interface station, if provided), which informs the controller 18 of the manner in which it is to control the other components of the blood separation device 10 during the procedure.

The operator may also proceed to enter various parameters, such as information regarding the blood source. In one embodiment, the operator also enters the target yield for the various blood components (which may also include entering a characteristic of the blood, such as a platelet pre-count) or some other collection control system (e.g., the amount of whole blood to be processed).

If there are any fluid containers (e.g., a storage solution container) that are not integrally formed with the fluid flow circuit 12, they may be connected to the fluid flow circuit 12 (e.g., by piercing a septum of a tube of the fluid flow circuit 12 or via a luer connector), with the fluid flow circuit 12 then being mounted to the blood separation device 10 (including the fluid containers F1-F7 being hung from the weight scales W1-W6 and the hooks or supports H1 and H2, as appropriate). An integrity check of the fluid flow circuit 12 may be executed by the controller 18 to ensure the various components are properly connected and functioning. Following a successful integrity check, the blood source is connected to the fluid flow circuit 12 and the fluid flow circuit 12 may be primed (e.g., by saline pumped from a saline bag F4 by operation of one or more of the pumps P1-P6 of the blood separation device 10).

When the fluid flow circuit 12 has been primed, blood separation may begin. The stages of blood separation vary depending on the particular procedure, and will be described in greater detail below.

A. Therapeutic Red Blood Cell Exchange

According to one aspect of the present disclosure, the blood separation device 10 may be used to execute a therapeutic red blood cell exchange procedure in which red blood cells are separated from blood. A red blood cell replacement fluid (e.g., donated red blood cells) is added to the remaining blood components, which are then conveyed to a recipient, while the separated red blood cells remain within the fluid circuit 12 as a waste product.

The blood separation device 10 may execute a therapeutic red blood cell exchange procedure using only the spinning membrane separator drive unit 14 or only the centrifugal separator 16, as will be described in greater detail.

1. Spinning Membrane Separation—First Embodiment

Figure 2A:
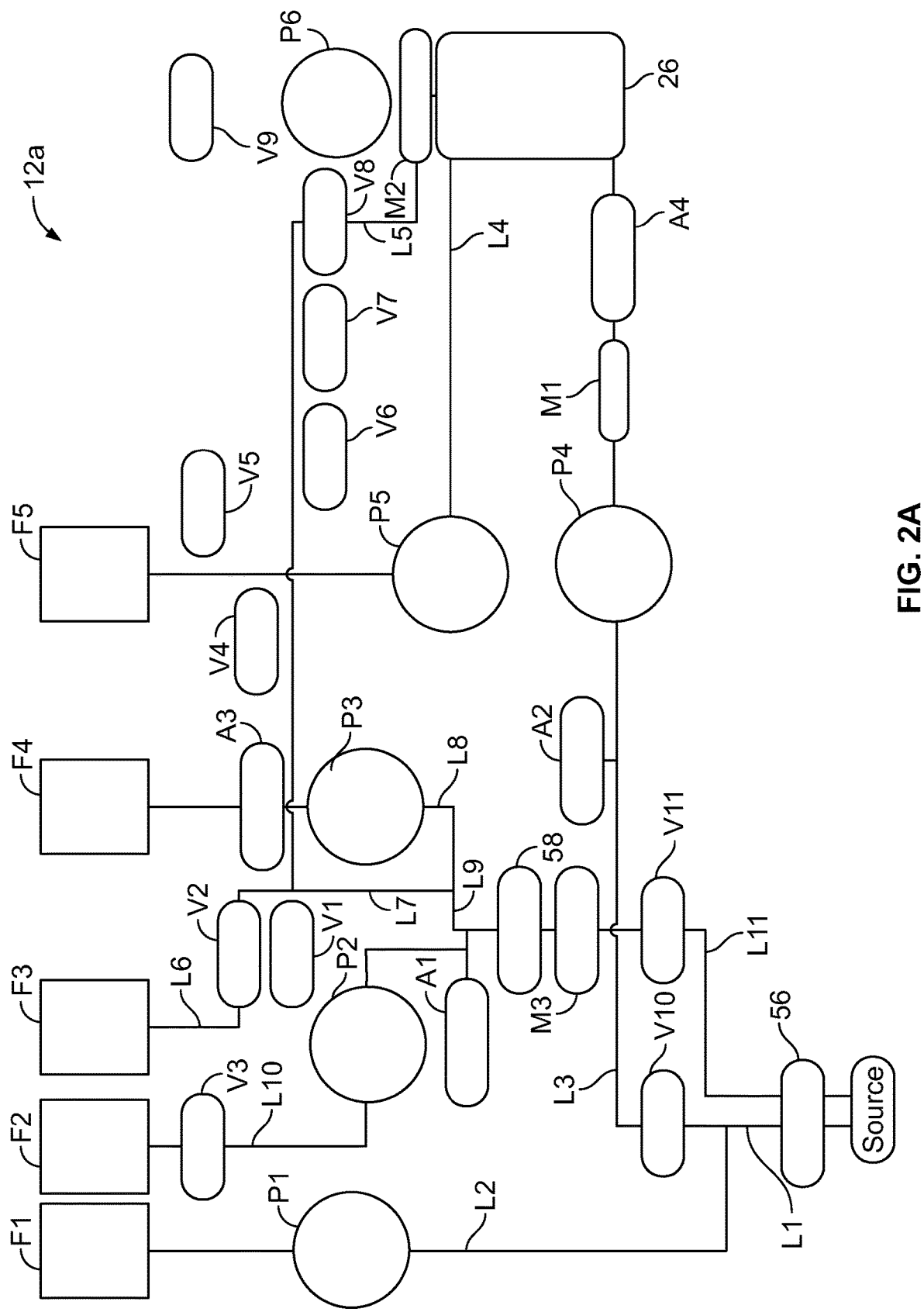
FIGS. 2A-2H are schematic views of different disposable fluid flow circuits that may be mounted to the blood separation device of FIG. 1 to complete a blood separation system according to an aspect of the present disclosure.
Figure 2B:
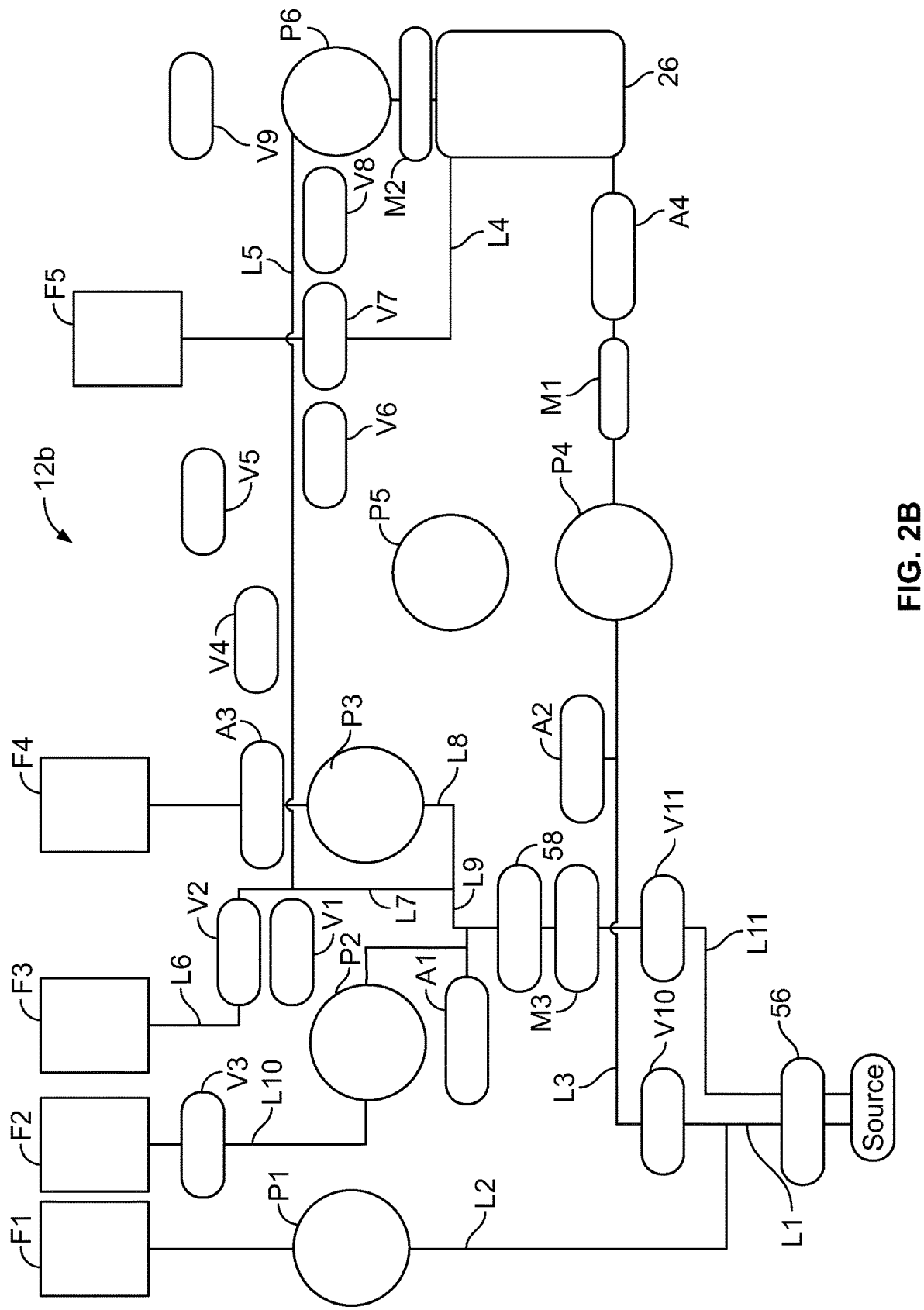

FIGS. 2A and 2B illustrate alternative embodiments of fluid flow circuits 12a, 12b suitable for execution of a therapeutic red blood cell exchange procedure using a spinning membrane separation approach. FIGS. 2A and 2B illustrate "double needle" configurations (in which separate blood access devices are employed to draw blood into the circuit from a blood source and to convey fluid to a recipient). This may be preferred over a "single needle" configuration (in which a single blood access device is employed to both draw blood into the circuit from a blood source and return fluid to the same blood source), due to the importance of maintaining an isovolumic state (for a human source/recipient) and due to the large blood volumes processed in typical exchange procedures of the type described herein, though it should be understood that a "single needle" configuration may instead be employed. The two fluid flow circuits 12a and 12b differ in the pump used to convey the separated blood components out of the spinning membrane separator 26, as will be described.

a. Fluid Flow Circuit

The fluid flow circuit 12a of FIG. 2A includes a cassette 48 of the type described above and illustrated in FIG. 4, which connects the various components of the fluid flow circuit 12a. The various connections amongst the components of the fluid flow circuit 12a are shown in FIG. 2A, which also shows the fluid flow circuit 12a mounted to the blood separation device 10.

Figure 43:
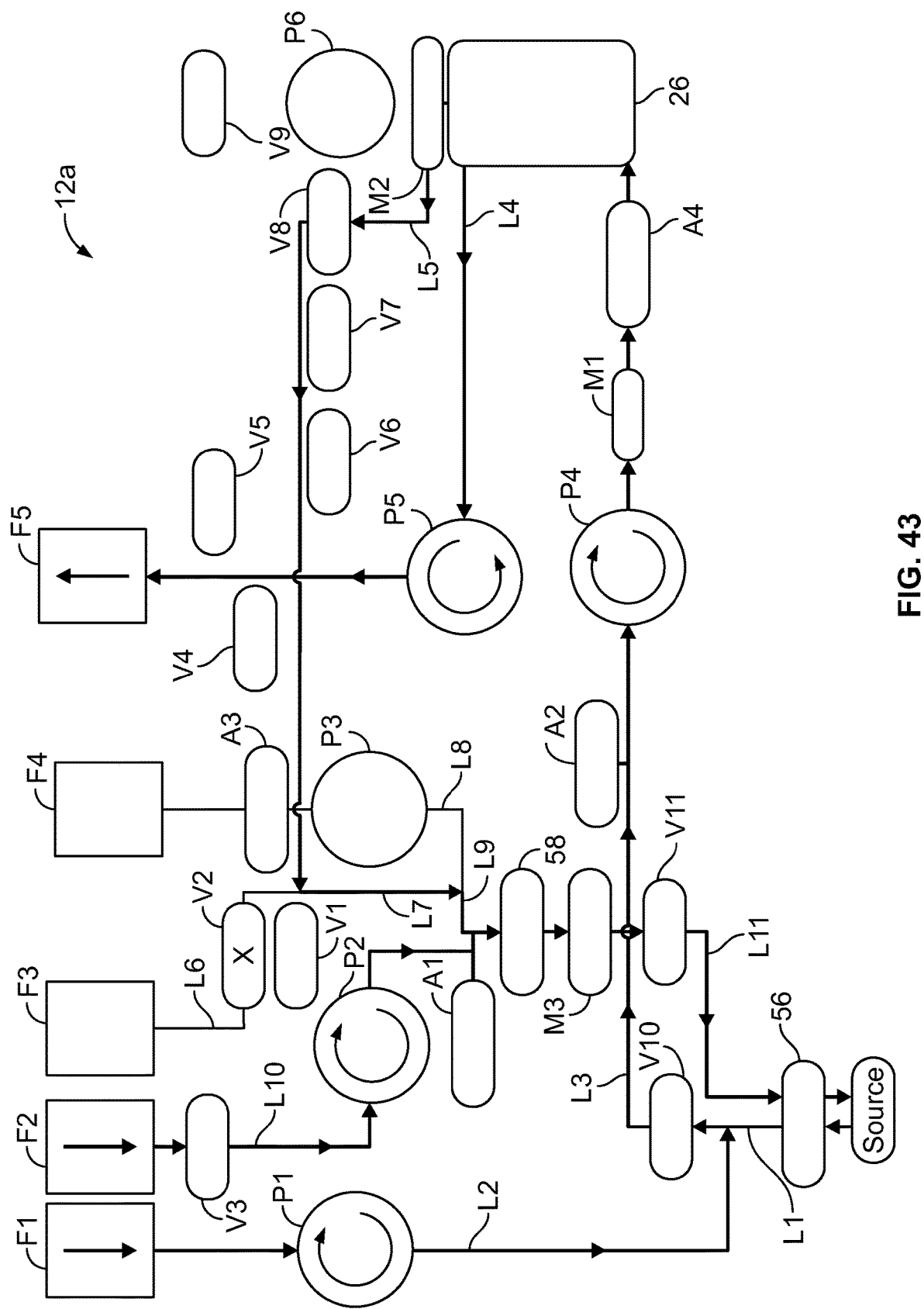
FIG. 43 is a schematic view of the fluid flow circuit of FIG. 2A mounted on the blood separation device of FIG. 1, showing the system carrying out different fluid flow tasks in connection with execution of a therapeutic red blood cell exchange procedure using a spinning membrane separation approach.

Components of the fluid flow circuit 12a interact with many of the components of the blood separation device 10, as will be described, but there are selected components of the blood separation device 10 that are not used in a therapeutic red blood cell exchange procedure using the fluid flow circuit 12a of FIG. 2A. Most notably, the centrifugal separator 16 is not used, but only the spinning membrane separator drive unit 14. There are also selected valves V1, V4, V5, V6, V7, and V9 and one pump P6 of the blood separation device 10 that are not used in the procedure described herein. The fluid flow circuit 12a includes a fluid container F3 (which may be referred to as a waste container) that, in the illustrated procedure of FIG. 43, is only used during the pre-processing priming phase, in which saline from the saline container F4 is pumped through the fluid flow circuit 12a to prime it, before being conveyed to the waste container F3 for disposal at the end of the procedure. However, it is also within the scope of the present disclosure for fluid to be conveyed into the waste container F3 and/or for saline to be conveyed to a fluid recipient from the saline container F4 during a procedure of this type.

b. Procedure

Blood is drawn into the fluid flow circuit 12a from a blood source (e.g., using a needle) via line L1, as shown in FIG. 43. The line L1 may include a manual clamp 56 that may initially be in a closed position to prevent fluid flow through the line L1. When processing is to begin, an operator may move the manual clamp 56 from its closed position to an open position to allow fluid flow through the line L1.

The blood is drawn into the line L1 by a pump P4 (which is referred to as a spinner pump when describing this procedure). Anticoagulant from an anticoagulant bag F1 may be added to the blood via line L2 by action of the anticoagulant pump P1. The valve V10 associated with valve station C10 is open to allow the flow of anticoagulated blood through line L3, thereby directing the blood toward the spinning membrane separator 26. Prior to reaching the spinning membrane separator 26, the blood may pass through the sensor station S2 associated with pressure sensor A2 (which may be upstream of the spinner pump P4 and may monitor vein pressure if the blood source is a living patient), a sensor M1 (which is referred to as a spinner inlet sensor when describing this procedure), and the sensor station S4 associated with pressure sensor A4. The spinner inlet sensor M1 may detect the hematocrit of the blood entering the spinning membrane separator 26 (which may be used to set the flow rate of the pump P5), while the pressure sensor A4 may monitor the pressure of the spinning membrane separator 26.

The spinning membrane separator drive unit 14 of the blood separation device 10 manipulates the spinning membrane separator 26 to separate plasma from the cellular blood components (i.e., red blood cells, platelets, and white blood cells). As described above, the spinning membrane separator 26 may be a larger spinning membrane separator or a smaller spinning membrane separator. In one embodiment, the spinning membrane separator drive unit 14 may rotate the rotor 72 at approximately 2,000-4,000 rpm to separate blood entering the bottom portion of the spinning membrane separator 26 into platelet-poor plasma and cellular blood components (as described above).

The cellular blood components are pumped out of the spinning membrane separator 26 via line L4 by the pump P5 (which is referred to as a red blood cell pump in this procedure) and into a red blood cell container F5.

Cell-free plasma exits the spinning membrane separator 26 via line L5 and travels through spinner outlet sensor M2 and the valve station C8 associated with open valve V8. The spinner outlet sensor M2 may cooperate with the controller 18 to determine one or more characteristics of the plasma, such as the amount of cellular blood components in the plasma and/or whether the plasma is hemolytic and/or lipemic. There is no pump associated with line L5, so instead the flow rate at which the plasma exits the spinning membrane separator 26 is equal to the difference between the flow rates of the spinner pump P4 and red blood cell pump P5.

Valve V2 associated with valve station C2 is closed to prevent flow through line L6 to the waste bag F3, thereby directing the plasma along line L7. The pump P3 associated with line L8 is inoperative, so the plasma is directed through line L9 instead, to a junction. The pump P2 (which may be referred to as a replacement fluid pump) associated with line L10 operates to draw a red blood cell replacement fluid (e.g., red blood cells from a donor) from red blood cell replacement fluid container F2. The replacement fluid travels through the valve station C3 associated with open valve V3 and to the junction with line L9, where it mixes with the platelet-free plasma.

The mixture travels through the sensor station S1 associated with pressure sensor A1 (which may monitor vein pressure if the fluid recipient is a living patient), a return line filter 58, air detector M3, the valve station C11 associated with open valve V11, and line L11 on its way to the recipient (which may be the same as the blood source) via the second needle or blood access device. As noted above, it is also possible for saline from the saline container F4 to be mixed with the plasma at the junction of lines L7 and L8 by operation of pump P3 prior to the plasma reaching the fluid recipient.

This single-phase procedure continues until an objective has been completed (e.g., a particular amount of red blood cells has been collected in the red blood cell container F5).

2. Spinning Membrane Separation—Second Embodiment a. Fluid Flow Circuit

The fluid flow circuit 12b of FIG. 2B is similar to the fluid flow circuit 12a of FIG. 2A, but is differently associated to the pump system of the blood separation device 10, as noted above.

Figure 44:
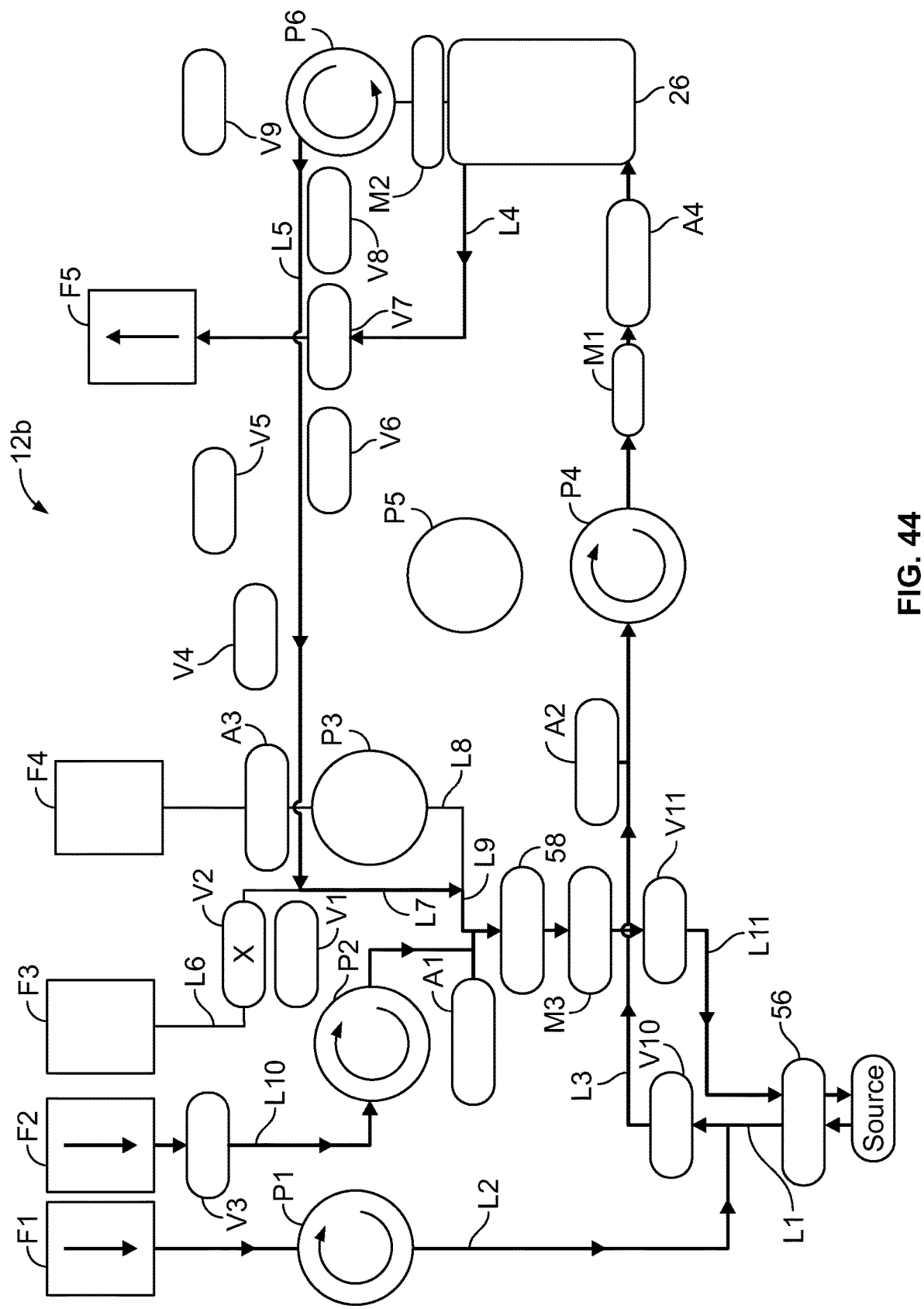
FIG. 44 is a schematic view of the fluid flow circuit of FIG. 2B mounted on the blood separation device of FIG. 1, showing the system carrying out different fluid flow tasks in connection with a therapeutic red blood cell exchange procedure using a spinning membrane separation approach.

Components of the fluid flow circuit 12b interact with many of the components of the blood separation device 10, as will be described, but there are selected components of the blood separation device 10 that are not used in a therapeutic red blood cell exchange procedure using the fluid flow circuit 12b of FIG. 2B. Most notably, the centrifugal separator 16 is not used, but only the spinning membrane separator drive unit 14. There are also selected valves V1, V4, V5, V6, V8, and V9 and one pump P5 of the blood separation device 10 that are not used in the procedure described herein. The fluid flow circuit 12b includes a waste container F3 that, in the illustrated procedure of FIG. 44, is only used during the pre-processing priming phase, in which saline from the saline container F4 is pumped through the fluid flow circuit 12b to prime it, before being conveyed to the waste container F3 for disposal at the end of the procedure. However, it is also within the scope of the present disclosure for fluid to be conveyed into the waste container F3 and/or for saline to be conveyed to a fluid recipient from the saline container F4 during a procedure of this type.

b. Procedure

Blood is drawn into the fluid flow circuit 12b from a blood source (e.g., using a needle) via line L1, as shown in FIG. 44. The line L1 may include a manual clamp 56 that may initially be in a closed position to prevent fluid flow through the line L1. When processing is to begin, an operator may move the manual clamp 56 from its closed position to an open position to allow fluid flow through the line L1.

The blood is drawn into the line L1 by the spinner pump P4. Anticoagulant from the anticoagulant bag F1 may be added to the blood via line L2 by action of the anticoagulant pump P1. The valve V10 associated with valve station C10 is open to allow the flow of anticoagulated blood through line L3, thereby directing the blood toward the spinning membrane separator 26. Prior to reaching the spinning membrane separator 26, the blood may pass through the sensor station S2 associated with pressure sensor A2, the spinner inlet sensor M1, and the sensor station S4 associated with pressure sensor A4, similar to the procedure of FIG. 43.

The spinning membrane separator drive unit 14 of the blood separation device 10 manipulates the spinning membrane separator 26 to separate plasma from the cellular blood components (i.e., red blood cells, platelets, and white blood cells). As described above, the spinning membrane separator 26 may be a larger spinning membrane separator or a smaller spinning membrane separator. In one embodiment, the spinning membrane separator drive unit 14 may rotate the rotor 72 at approximately 2,000-4,000 rpm to separate blood entering the bottom portion of the spinning membrane separator 26 into platelet-poor plasma and cellular blood components (as described above).

Rather than the cellular blood components being pumped out of the spinning membrane separator 26 (as in the procedure of FIG. 43), the cell-free plasma is instead pumped out of the spinning membrane separator 26 via line L5 by the pump P6 (which may be referred to as the plasma pump). The cellular blood components exit the spinning membrane separator 26 via line L4 and travel through the valve station C7 associated with open valve V7 and into the red blood cell container F5. As there is no pump associated with line L4, the flow rate at which the cellular blood components exit the spinning membrane separator 26 is equal to the difference between the flow rates of the spinner pump P4 and plasma pump P6.

The platelet-free plasma is pumped through line L5 by the plasma pump P6, traveling through spinner outlet sensor M2. Valve V2 associated with valve station C2 is closed to prevent flow through line L6 to the waste bag F3, thereby directing the plasma along line L7. The pump P3 associated with line L8 is inoperative, so the plasma is directed through line L9 instead, to a junction. The replacement fluid pump P2 associated with line L10 operates to draw a red blood cell replacement fluid (e.g., red blood cells from a donor) from the red blood cell replacement fluid container F2. The replacement fluid travels through the valve station C3 associated with open valve V3 and to the junction with line L9, where it mixes with the platelet-free plasma.

The mixture travels through the sensor station S1 associated with pressure sensor A1, the return line filter 58, air detector M3, the valve station C11 associated with open valve V11, and line L11 on its way to the recipient (which may be the same as the blood source) via the second needle or blood access device. As noted above, it is also possible for saline from the saline container F4 to be mixed with the plasma at the junction of lines L7 and L8 by operation of pump P3 prior to the plasma reaching the fluid recipient.

This single-phase procedure continues until an objective has been completed (e.g., a particular amount of red blood cells has been collected in the red blood cell container F5).

The preference of using the red blood cell pump P5 or the plasma pump P6 may depend on any of a number of factors. In general, though, it may be preferred to employ the red blood cell pump P5 (as in the procedure of FIG. 43), as the red blood cells are treated as a waste product, so there is less concern about any damage possibly caused to the red blood cells by the red blood cell pump P5. However, as the plasma being conveyed to the fluid recipient will tend to be substantially cell-free, there is also less risk of damage being done to the fluid being conveyed to the recipient when using the plasma pump P6 (as in the procedure of FIG. 44).

3. Centrifugal Separation—First Embodiment

Figure 2C:
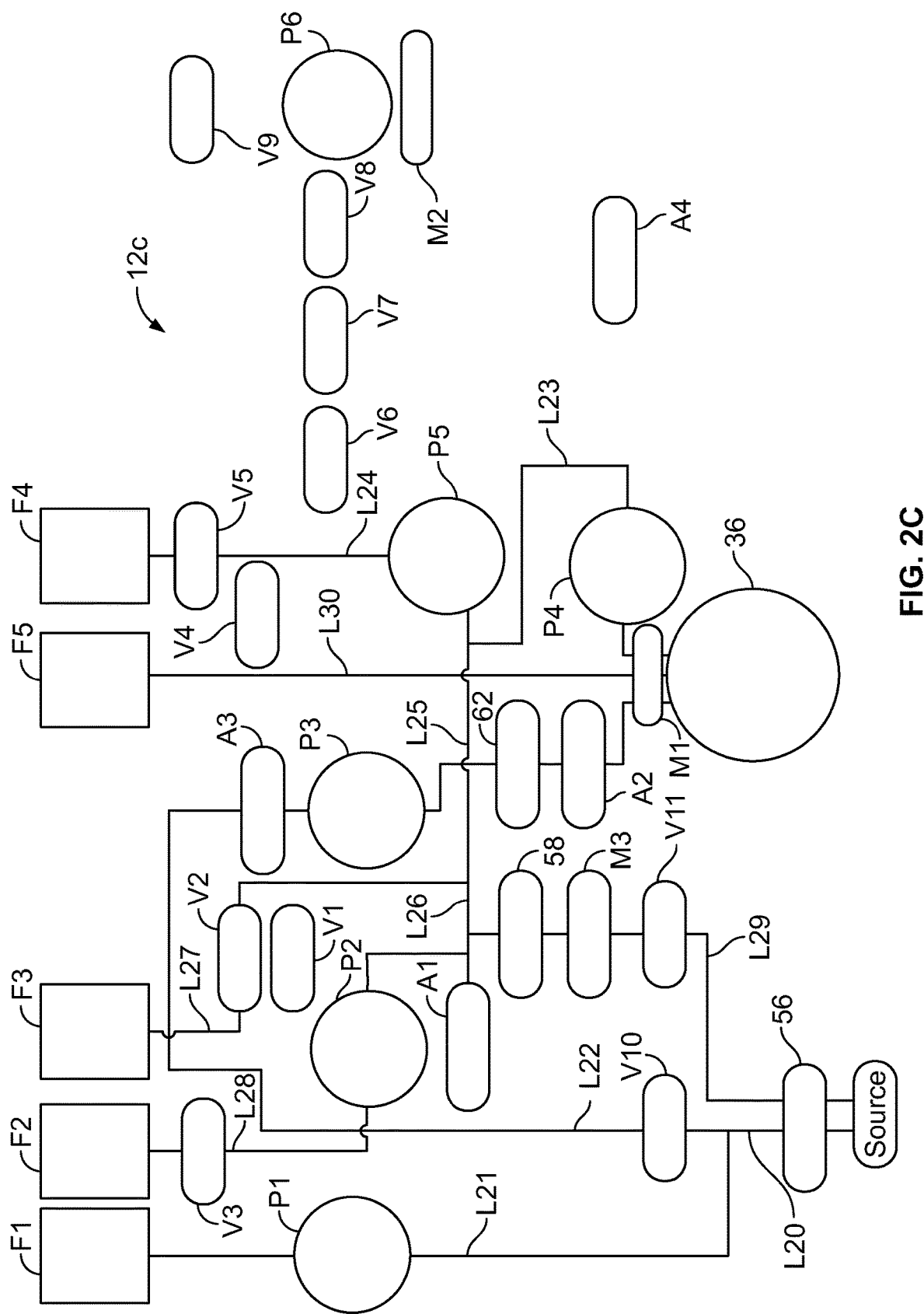
Figure 2D:
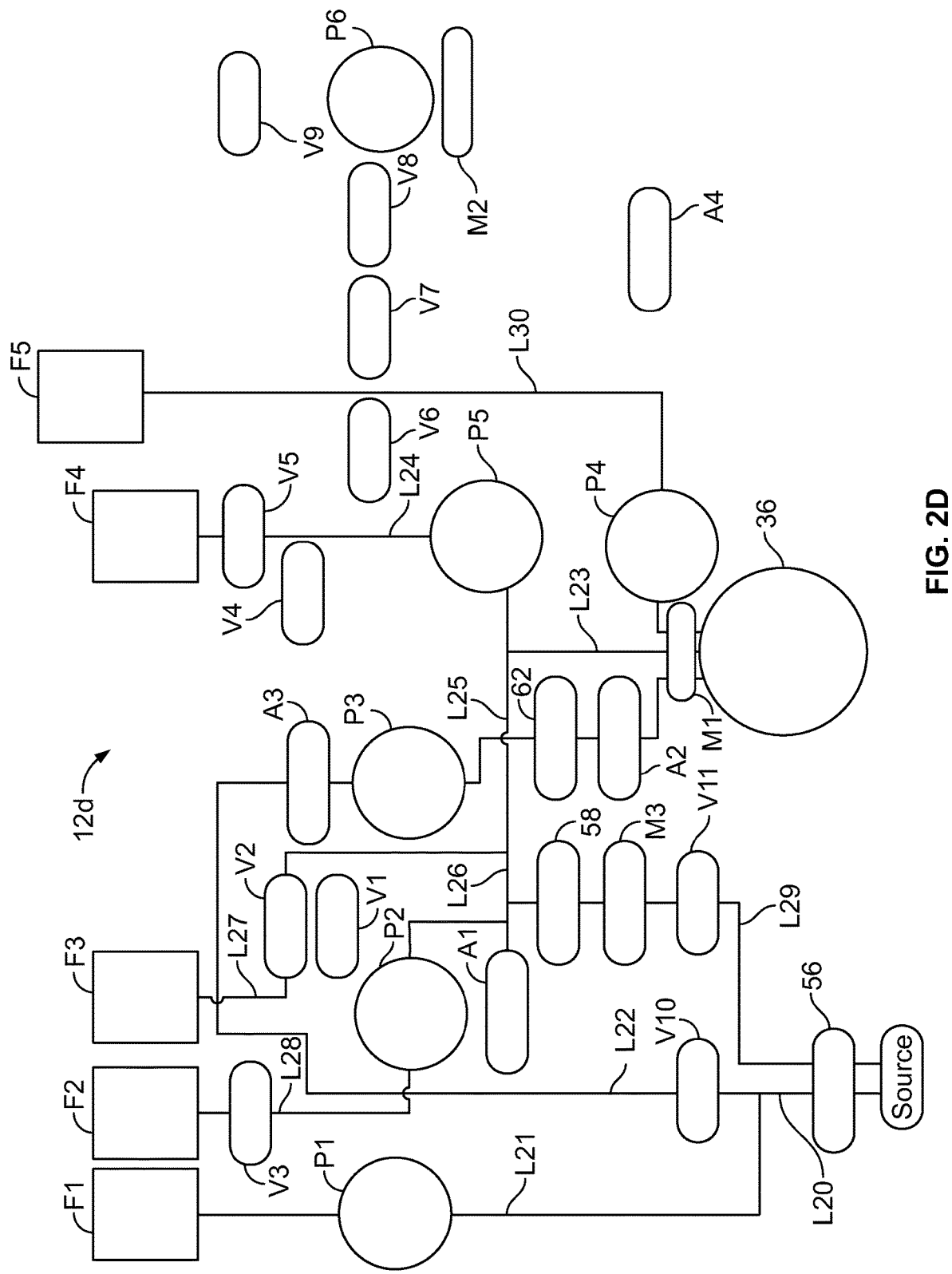

FIGS. 2C and 2D illustrate alternative embodiments of fluid flow circuits 12c, 12d suitable for execution of a therapeutic red blood cell exchange procedure using a centrifugal separation approach. While FIGS. 2C and 2D illustrate "double needle" configurations (in which separate blood access devices are employed to draw blood into the circuit from a blood source and to convey fluid to a recipient), it should be understood that a "single needle" configuration (in which a single blood access device is employed to both draw blood into the circuit from a blood source and return fluid to the same blood source) may instead be employed. The two fluid flow circuits 12c and 12d differ in the pump used to convey the separated blood components out of the centrifugal separation chamber 36, as will be described.

a. Fluid Flow Circuit

The fluid flow circuit 12c includes a cassette 48 of the type described above and illustrated in FIG. 4, which connects the various components of the fluid flow circuit 12c. The various connections amongst the components of the fluid flow circuit 12c are shown in FIG. 2C, which also shows the fluid flow circuit 12c mounted to the blood separation device 10.

Figure 45:
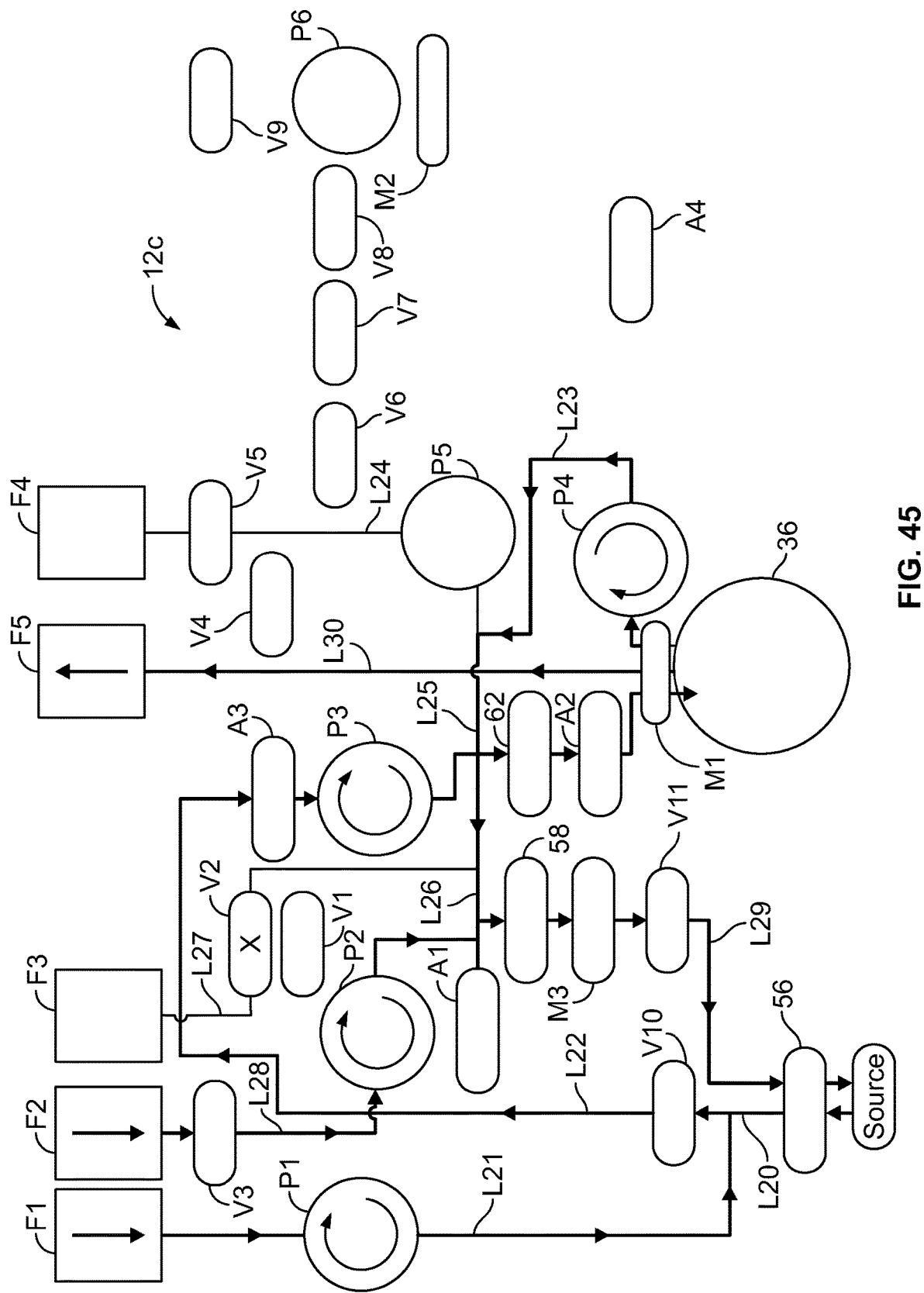
FIG. 45 is a schematic view of the fluid flow circuit of FIG. 2C mounted on the blood separation device of FIG. 1, showing the system carrying out different fluid flow tasks in connection with a therapeutic red blood cell exchange procedure using a centrifugal separation approach.

Components of the fluid flow circuit 12c interact with many of the components of the blood separation device 10, as will be described, but there are selected components of the blood separation device 10 that are not used in a therapeutic red blood cell exchange procedure using the fluid flow circuit 12c of FIG. 2C. Most notably, the spinning membrane separator drive unit 14 is not used, but only the centrifugal separator 16. There are also selected valves V1, V4, V6, V7, V8, and V9, one pump P6, one pressure sensor A4, and the spinner outlet sensor M2 of the blood separation device 10 that are not used in the procedure described herein. The fluid flow circuit 12c includes a waste container F3 that, in the illustrated procedure of FIG. 45, is only used during the pre-processing priming phase, in which saline from the saline container F4 is pumped through the fluid flow circuit 12c to prime it, before being conveyed to the waste container F3 for disposal at the end of the procedure. However, it is also within the scope of the present disclosure for fluid to be conveyed into the waste container F3 and/or for saline to be conveyed to a fluid recipient from the saline container F4 during a procedure of this type.

b. Procedure

Blood is drawn into the fluid flow circuit 12c from a blood source (e.g., using a needle) via line L20, as shown in FIG. 45. The line L20 may include a manual clamp 56 that may initially be in a closed position to prevent fluid flow through the line L20. When processing is to begin, an operator may move the manual clamp 56 from its closed position to an open position to allow fluid flow through the line L20.

The blood is drawn into the line L20 by pump P3 (which is referred to as a centrifuge pump when describing this procedure). Anticoagulant from the anticoagulant container F1 may be added to the blood via line L21 by action of the anticoagulant pump P1. The valve V10 associated with valve station C10 is open to allow the flow of anticoagulated blood through line L22 and through a sensor station S3 associated with pressure station A3. If the blood source is a living body (e.g., a patient), the pressure sensor A3 may communicate with the controller 18 to monitor the pressure within the vein of the blood source.

The blood flowing through line L22 passes through an air trap 62, a sensor station S2 associated with pressure sensor A2 (which monitors the pressure of the centrifugal separation chamber 36), and a centrifugal separator sensor M1, before entering the centrifugal separation chamber 36. The centrifugal separator sensor M1 may detect the hematocrit of the blood entering the centrifugal separation chamber 36, for example.

The centrifugal separator 16 of the blood separation device 10 manipulates the centrifugal separation chamber 36 to separate red blood cells from a plasma constituent, which will typically be platelet-rich plasma, but may also be platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and platelet-rich plasma (as described above).

The plasma constituent is pumped out of the centrifugal separation chamber 36 via line L23 under action of the pump P4 (which is referred to as a plasma pump when describing this procedure). Pump P5 associated with line L24 may be inoperative, thereby directing the plasma through line L25 to a junction. Valve V2 associated with valve station C2 is closed, thereby directing the plasma through line L26 instead of through line L27. The replacement fluid pump P2 associated with line L28 operates to draw a red blood cell replacement fluid (e.g., red blood cells from a donor) from red blood cell replacement fluid container F2. The replacement fluid travels through the valve station C3 associated with open valve V3 and to the junction with line L26, where it mixes with the plasma constituent.

The mixture travels through the sensor station S1 associated with pressure sensor A1 (which may monitor vein pressure if the fluid recipient is a living patient), a return line filter 58, air detector M3, the valve station C11 associated with open valve V11, and line L29 on its way to the recipient (which may be the same as the blood source) via the second needle or blood access device. As noted above, it is also possible for saline from the saline container F4 to be mixed with the plasma at the junction of lines L23 and L24 by operation of pump P5 prior to the plasma reaching the fluid recipient.

As for the red blood cells, they flow out of the centrifugal separation chamber 36 via line L30 and into the red blood cell container F5. There is no pump associated with line L30, so instead the flow rate at which the red blood cells exit the centrifugal separation chamber 36 is equal to the difference between the flow rates of the centrifuge pump P3 and plasma pump P4.

This single-phase procedure continues until an objective has been completed (e.g., a particular amount of red blood cells has been collected in the red blood cell container F5).

4. Centrifugal Separation—Second Embodiment a. Fluid Flow Circuit

The fluid flow circuit 12d of FIG. 2D is similar to the fluid flow circuit 12c of FIG. 2C, but is differently associated to the pump system of the blood separation device 10, as noted above.

Figure 46:
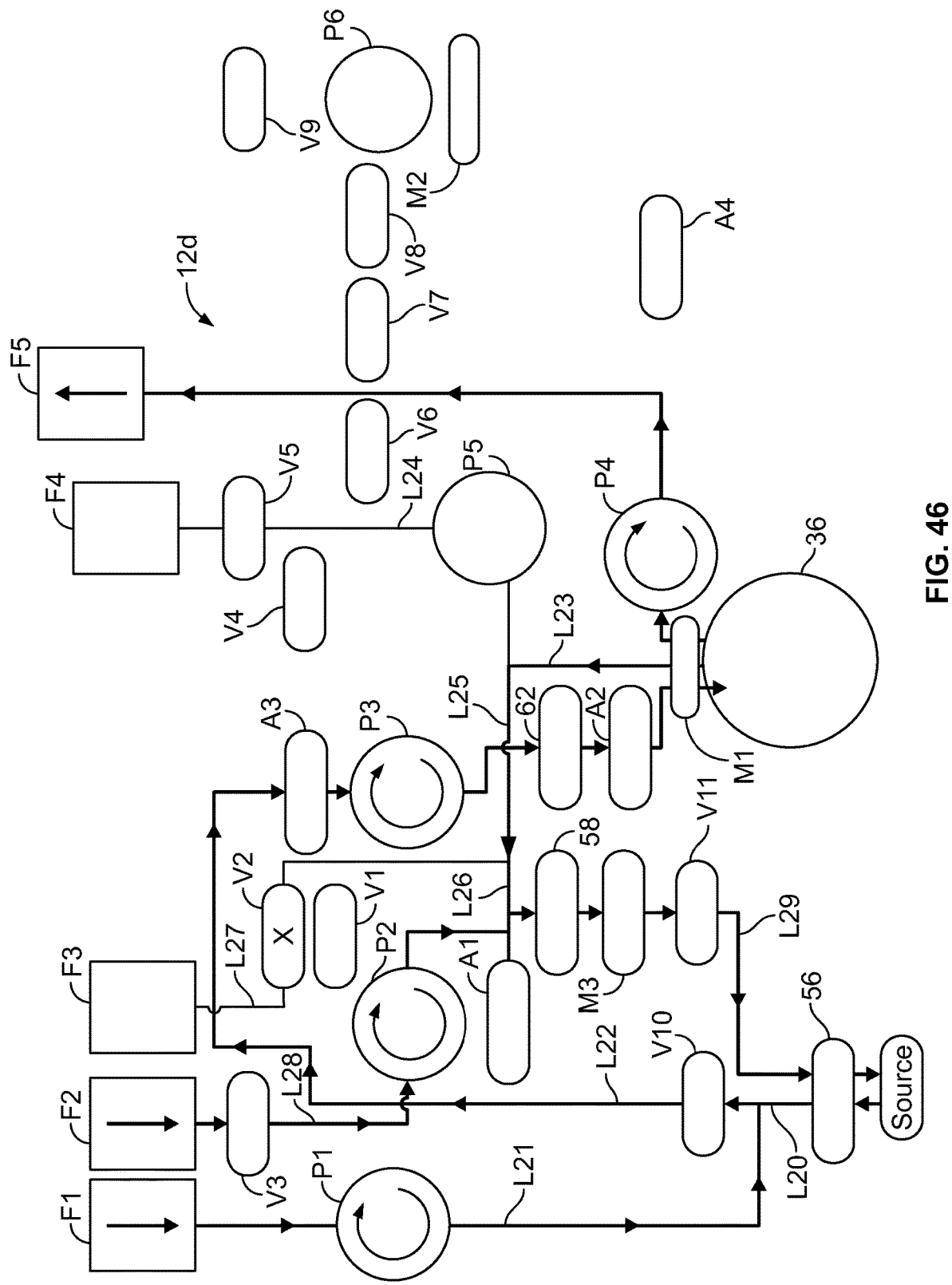
FIG. 46 is a schematic view of the fluid flow circuit of FIG. 2D mounted on the blood separation device of FIG. 1, showing the system carrying out different fluid flow tasks in connection with a therapeutic red blood cell exchange procedure using a centrifugal separation approach.

Components of the fluid flow circuit 12d interact with many of the components of the blood separation device 10, as will be described, but there are selected components of the blood separation device 10 that are not used in a therapeutic red blood cell exchange procedure using the fluid flow circuit 12d of FIG. 2D. Most notably, the spinning membrane separator drive unit 14 is not used, but only the centrifugal separator 16. There are also selected valves V1, V4, V6, V7, V8, and V9, one pump P6, one pressure sensor A4, and the spinner outlet sensor M2 of the blood separation device 10 that are not used in the procedure described herein. The fluid flow circuit 12d includes a waste container F3 that, in the illustrated procedure of FIG. 46, is only used during the pre-processing priming phase, in which saline from the saline container F4 is pumped through the fluid flow circuit 12*d* to prime it, before being conveyed to the waste container F3 for disposal at the end of the procedure. However, it is also within the scope of the present disclosure for fluid to be conveyed into the waste container F3 and/or for saline to be conveyed to a fluid recipient from the saline container F4 during a procedure of this type.

b. Procedure

Blood is drawn into the fluid flow circuit 12*d* from a blood source (e.g., using a needle) via line L20, as shown in FIG. 46. The line L20 may include a manual clamp 56 that may initially be in a closed position to prevent fluid flow through the line L20. When processing is to begin, an operator may move the manual clamp 56 from its closed position to an open position to allow fluid flow through the line L20.

The blood is drawn into the line L20 by the centrifuge pump P3. Anticoagulant from the anticoagulant container F1 may be added to the blood via line L21 by action of the anticoagulant pump P1. The valve V10 associated with valve station C10 is open to allow the flow of anticoagulated blood through line L22 and through a sensor station S3 associated with pressure station A3. If the blood source is a living body (e.g., a patient), the pressure sensor A3 may communicate with the controller 18 to monitor the pressure within the vein of the blood source.

The blood flowing through line L22 passes through an air trap 62, a sensor station S2 associated with pressure sensor A2 (which monitors the pressure of the centrifugal separation chamber 36), and a centrifugal separator sensor M1, before entering the centrifugal separation chamber 36, as in the procedure of FIG. 45.

The centrifugal separator 16 of the blood separation device 10 manipulates the centrifugal separation chamber 36 to separate red blood cells from a plasma constituent, which will typically be platelet-rich plasma, but may also be platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and platelet-rich plasma (as described above).

Rather than the plasma constituent being pumped out of the centrifugal separation chamber 36 (as in the procedure of FIG. 45), the red blood cells are instead pumped out of the centrifugal separation chamber 36 via line L30 by the pump P4 (which is referred to as the red blood cell pump when describing this procedure) and into the red blood cell container F5.

The plasma constituent exits the centrifugal separation chamber 36 via line L23. As there is no pump associated with line L23, the flow rate at which the plasma constituent exits the centrifugal separation chamber 36 is equal to the difference between the flow rates of the centrifuge pump P3 and the red blood cell pump P4.

Pump P5 associated with line L24 may be inoperative, thereby directing the plasma constituent through line L25 to a junction. Valve V2 associated with valve station C2 is closed, thereby directing the plasma through line L26 instead of through line L27. The replacement fluid pump P2 associated with line L28 operates to draw a red blood cell replacement fluid (e.g., red blood cells from a donor) from red blood cell replacement fluid container F2. The replacement fluid travels through the valve station C3 associated with open valve V3 and to the junction with line L26, where it mixes with the plasma constituent.

The mixture travels through the sensor station S1 associated with pressure sensor A1, the return line filter 58, air detector M3, the valve station C11 associated with open valve V11, and line L29 on its way to the recipient (which may be the same as the blood source) via the second needle or blood access device. As noted above, it is also possible for saline from the saline container F4 to be mixed with the plasma constituent at the junction of lines L23 and L24 by operation of pump P5 prior to the plasma constituent reaching the fluid recipient.

This single-phase procedure continues until an objective has been completed (e.g., a particular amount of red blood cells has been collected in the red blood cell container F5).

As described above with regard to the procedures of FIGS. 43 and 44, the preference of using pump P4 to pump red blood cells or the plasma constituent from the centrifugal separation chamber 36 may depend on any of a number of factors. As above, it may be preferred to employ the pump P4 to pump red blood cells (as in the procedure of FIG. 46), as the red blood cells are treated as a waste product, so there is less concern about any damage possibly caused to the red blood cells by the pump P4. This may be especially preferred when using a centrifugal separation approach, as the plasma constituent will typically comprise platelet-rich plasma, such that it may be advantageous to avoid the risk of damage to any cellular components (e.g., platelets) being conveyed to the fluid recipient when using the pump P4 to pump the plasma constituent from the centrifugal separation chamber 36 (as in the procedure of FIG. 45).

B. Therapeutic Plasma Exchange

According to another aspect of the present disclosure, the blood separation device 10 may be used to execute a therapeutic plasma exchange procedure in which plasma is separated from blood. A plasma replacement fluid (e.g., donated plasma) is added to the remaining blood components, which are then conveyed to a recipient, while the separated plasma remains within the fluid circuit 12 as a waste product. It should be understood that the present disclosure encompasses a blood separation device 10 configured for therapeutic red blood cell exchange and not for therapeutic plasma exchange, for therapeutic plasma exchange and not for therapeutic red blood cell exchange, and for both therapeutic red blood cell exchange and therapeutic plasma exchange (in addition to any other procedures that the blood separation device 10 may execute).

The blood separation device 10 may execute a therapeutic plasma exchange procedure using only the spinning membrane separator drive unit 14 or only the centrifugal separator 16, as will be described in greater detail.

1. Spinning Membrane Separation—First Embodiment

Figure 2E:
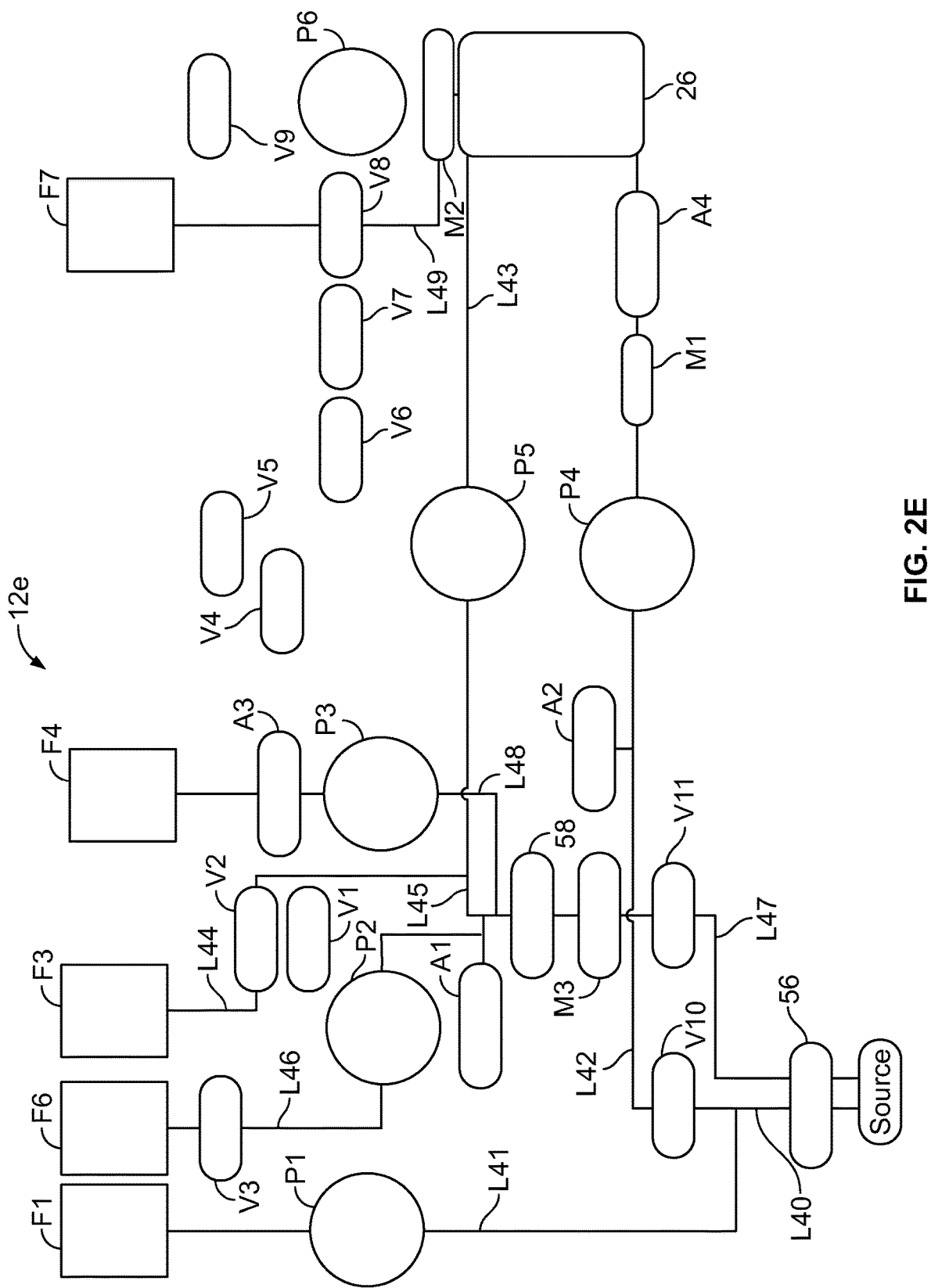
Figure 2F:
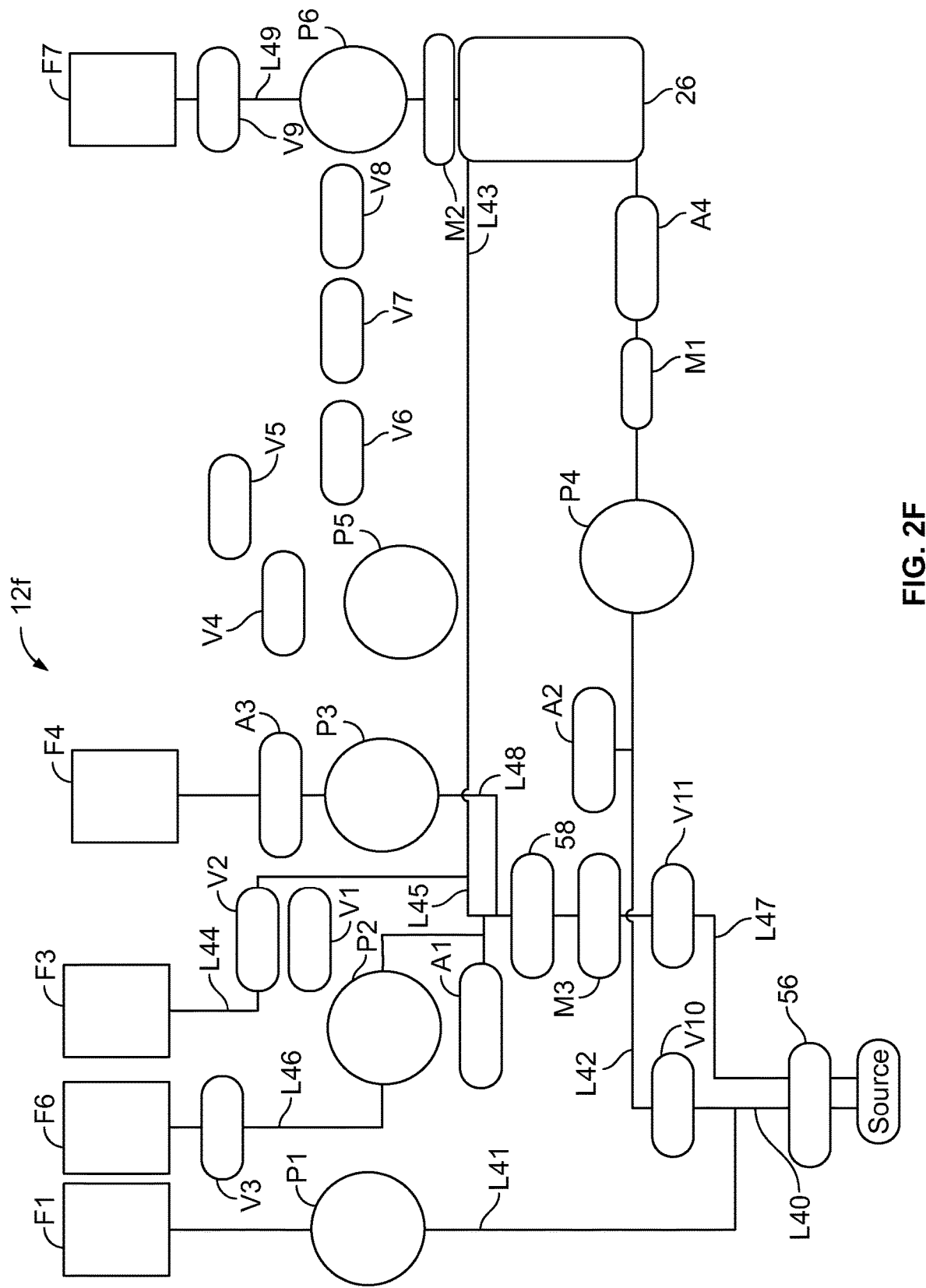

FIGS. 2E and 2F illustrate alternative embodiments of fluid flow circuits 12*e*, 12*f* suitable for execution of a therapeutic plasma exchange procedure using a spinning membrane separation approach. While FIGS. 2E and 2F illustrate "double needle" configurations (in which separate blood access devices are employed to draw blood into the circuit from a blood source and to convey fluid to a recipient), it should be understood that a "single needle" configuration (in which a single blood access device is employed to both draw blood into the circuit from a blood source and return fluid to the same blood source) may instead be employed. The two fluid flow circuits 12e and 12f differ in the pump used to convey the separated blood components out of the spinning membrane separator 26, as will be described.

a. Fluid Flow Circuit

The fluid flow circuit 12e of FIG. 2E includes a cassette 48 of the type described above and illustrated in FIG. 4, which connects the various components of the fluid flow circuit 12F. The various connections amongst the components of the fluid flow circuit 12e are shown in FIG. 2E, which also shows the fluid flow circuit 12e mounted to the blood separation device 10.

Figure 47:
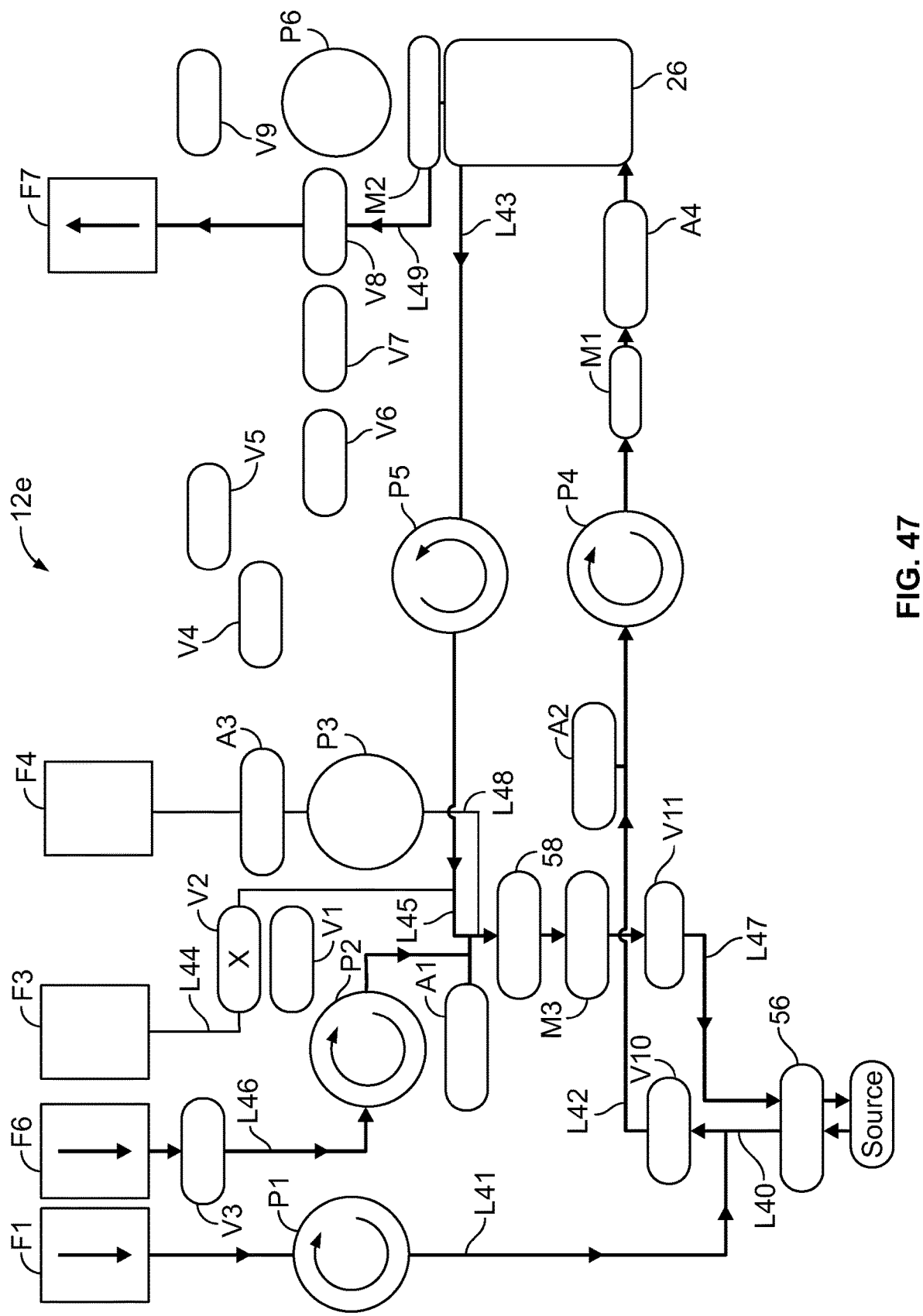
FIG. 47 is a schematic view of the fluid flow circuit of FIG. 2E mounted on the blood separation device of FIG. 1, showing the system carrying out different fluid flow tasks in connection with a therapeutic plasma exchange procedure using a spinning membrane separation approach.

Components of the fluid flow circuit 12e interact with many of the components of the blood separation device 10, as will be described, but there are selected components of the blood separation device 10 that are not used in a therapeutic plasma exchange procedure using the fluid flow circuit 12e of FIG. 2E. Most notably, the centrifugal separator 16 is not used, but only the spinning membrane separator drive unit 14. There are also selected valves V1, V4, V5, V6, V7, and V9 and one pump P6 of the blood separation device 10 that are not used in the procedure described herein. The fluid flow circuit 12e includes a waste container F3 that, in the illustrated procedure of FIG. 47, is only used during the pre-processing priming phase, in which saline from the saline container F4 is pumped through the fluid flow circuit 12e to prime it, before being conveyed to the waste container F3 for disposal at the end of the procedure. However, it is also within the scope of the present disclosure for fluid to be conveyed into the waste container F3 and/or for saline to be conveyed to a fluid recipient from the saline container F4 during a procedure of this type.

b. Procedure

Blood is drawn into the fluid flow circuit 12e from a blood source (e.g., using a needle) via line L40, as shown in FIG. 47. The line L40 may include a manual clamp 56 that may initially be in a closed position to prevent fluid flow through the line L40. When processing is to begin, an operator may move the manual clamp 56 from its closed position to an open position to allow fluid flow through the line L40.

The blood is drawn into the line L40 by a pump P4 (which is referred to as a spinner pump when describing this procedure). Anticoagulant from the anticoagulant bag F1 may be added to the blood via line L41 by action of the anticoagulant pump P1. The valve V10 associated with valve station C10 is open to allow the flow of anticoagulated blood through line L42, thereby directing the blood toward the spinning membrane separator 26. Prior to reaching the spinning membrane separator 26, the blood may pass through the sensor station S2 associated with pressure sensor A2, a sensor M1 (which is referred to as a spinner inlet sensor when describing this procedure), and the sensor station S4 associated with pressure sensor A4. The sensors A2 and M1 may be configured to operate in accordance with the preceding description of the procedure of FIG. 43.

The spinning membrane separator drive unit 14 of the blood separation device 10 manipulates the spinning membrane separator 26 to separate plasma from the cellular blood components (i.e., red blood cells, platelets, and white blood cells). As described above, the spinning membrane separator 26 may be a larger spinning membrane separator or a smaller spinning membrane separator. In one embodiment, the spinning membrane separator drive unit 14 may rotate the rotor 72 at approximately 2,000-4,000 rpm to separate blood entering the bottom portion of the spinning membrane separator 26 into platelet-poor plasma and cellular blood components (as described above).

The cellular blood components are pumped out of the spinning membrane separator 26 via line L43 by pump P5 (which is referred to as a red blood cell pump in this procedure). The valve V2 associated with valve station C2 is closed to prevent fluid flow through line L44 to the waste container F3, thereby directing the cellular blood components along line L45 to a junction. The replacement fluid pump P2 associated with line L46 operates to draw a plasma replacement fluid (e.g., plasma from a donor) from a plasma replacement fluid container F6. The replacement fluid travels through the valve station C3 associated with open valve V3 and to the junction with line L45, where it mixes with the cellular blood components.

The mixture travels through the sensor station S1 associated with pressure sensor A1 and into line L47. The sensor A1 may be configured to operate in accordance with the preceding description of the procedure of FIG. 43.

The pump P3 associated with line L48 is inoperative, thereby directing the mixture through the return line filter 58, air detector M3, and the valve station C11 associated with open valve V11 on its way to the recipient (which may be the same as the blood source) via the second needle or blood access device. As noted above, it is also possible for saline from the saline bag F4 to be mixed with the cellular blood components at the junction of lines L47 and L48 by operation of pump P3 prior to the cellular blood components reaching the fluid recipient.

Cell-free plasma exits the spinning membrane separator 26 via line L49 and travels through spinner outlet sensor M2, which may be configured to operate in accordance with the preceding description of the procedure of FIG. 43. The valve V8 associated with valve station C8 is open, thereby directing the plasma and into the plasma container F7. There is no pump associated with line L49, so instead the flow rate at which the plasma exits the spinning membrane separator 26 is equal to the difference between the flow rates of the spinner pump P4 and the red blood cell pump P5.

This single-phase procedure continues until an objective has been completed (e.g., a particular amount of plasma has been collected in the plasma container F7).

2. Spinning Membrane Separation—Second Embodiment a. Fluid Flow Circuit

The fluid flow circuit 12f of FIG. 2F is similar to the fluid flow circuit 12e of FIG. 2E, but is differently associated to the pump system of the blood separation device 10, as noted above.

Figure 48:
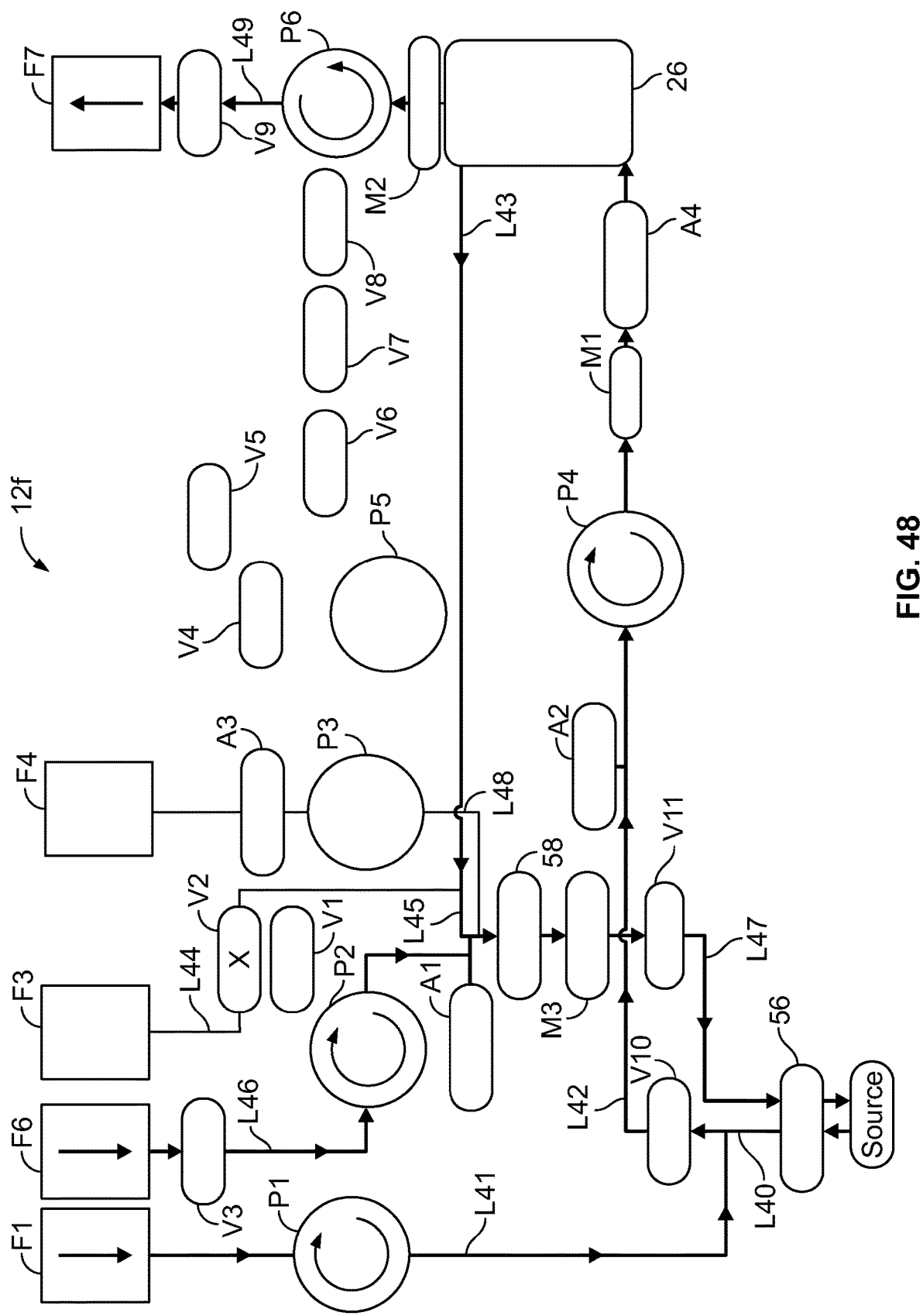
FIG. 48 is a schematic view of the fluid flow circuit of FIG. 2F mounted on the blood separation device of FIG. 1, showing the system carrying out different fluid flow tasks in connection with a therapeutic plasma exchange procedure using a spinning membrane separation approach.

Components of the fluid flow circuit 12f interact with many of the components of the blood separation device 10, as will be described, but there are selected components of the blood separation device 10 that are not used in a therapeutic plasma exchange procedure using the fluid flow circuit 12f of FIG. 2F. Most notably, the centrifugal separator 16 is not used, but only the spinning membrane separator drive unit 14. There are also selected valves V1, V4, V5, V6, V7, and V8 and one pump P5 of the blood separation device 10 that are not used in the procedure described herein. The fluid flow circuit 12f includes a waste container F3 that, in the illustrated procedure of FIG. 48, is only used during the pre-processing priming phase, in which saline from the saline container F4 is pumped through the fluid flow circuit 12f to prime it, before being conveyed to the waste container F3 for disposal at the end of the procedure. However, it is also within the scope of the present disclosure for fluid to be conveyed into the waste container F3 and/or for saline to be conveyed to a fluid recipient from the saline container F4 during a procedure of this type.

b. Procedure

Blood is drawn into the fluid flow circuit 12f from a blood source (e.g., using a needle) via line L40, as shown in FIG. 48. The line L40 may include a manual clamp 56 that may initially be in a closed position to prevent fluid flow through the line L40. When processing is to begin, an operator may move the manual clamp 56 from its closed position to an open position to allow fluid flow through the line L40.

The blood is drawn into the line L40 by the spinner pump P4. Anticoagulant from the anticoagulant bag F1 may be added to the blood via line L41 by action of the anticoagulant pump P1. The valve V10 associated with valve station C10 is open to allow the flow of anticoagulated blood through line L42, thereby directing the blood toward the spinning membrane separator 26. Prior to reaching the spinning membrane separator 26, the blood may pass through the sensor station S2 associated with pressure sensor A2, spinner inlet sensor M1, and the sensor station S4 associated with pressure sensor A4, similar to the procedure of FIG. 47.

The spinning membrane separator drive unit 14 of the blood separation device 10 manipulates the spinning membrane separator 26 to separate plasma from the cellular blood components (i.e., red blood cells, platelets, and white blood cells). As described above, the spinning membrane separator 26 may be a larger spinning membrane separator or a smaller spinning membrane separator. In one embodiment, the spinning membrane separator drive unit 14 may rotate the rotor 72 at approximately 2,000-4,000 rpm to separate blood entering the bottom portion of the spinning membrane separator 26 into platelet-poor plasma and cellular blood components (as described above).

Rather than the cellular blood components being pumped out of the spinning membrane separator 26 (as in the procedure of FIG. 47), the cell-free plasma is instead pumped out of the spinning membrane separator 26 via line L49 by the plasma pump P6. The cell-free plasma travels through spinner outlet sensor M2 and the valve station C9 associated with open valve V9, thereby directing the plasma and into the plasma container F7.

The cellular blood components exit the spinning membrane separator 26 via line L43. As there is no pump associated with line L43, the flow rate at which the cellular blood components exit the spinning membrane separator 26 is equal to the difference between the flow rates of the spinner pump P4 and the plasma pump P6.

The valve V2 associated with valve station C2 is closed to prevent fluid flow through line L44 to the waste container F3, thereby directing the cellular blood components along line L45 to a junction. The replacement fluid pump P2 associated with line L46 operates to draw a plasma replacement fluid (e.g., plasma from a donor) from the plasma replacement fluid container F6. The replacement fluid travels through the valve station C3 associated with open valve V3 and to the junction with line L45, where it mixes with the cellular blood components.

The mixture travels through the sensor station S1 associated with pressure sensor A1 and into line L47. The pump P3 associated with line L48 is inoperative, thereby directing the mixture through the return line filter 58, air detector M3, and the valve station C11 associated with open valve V11 on its way to the recipient (which may be the same as the blood source) via the second needle or blood access device. As noted above, it is also possible for saline from the saline bag F4 to be mixed with the cellular blood components at the junction of lines L47 and L48 by operation of pump P3 prior to the cellular blood components reaching the fluid recipient.

This single-phase procedure continues until an objective has been completed (e.g., a particular amount of plasma has been collected in the plasma container F7).

The preference of using the red blood cell pump P5 or the plasma pump P6 may depend on any of a number of factors. In general, though, it may be preferred to employ the plasma pump P6 (as in the procedure of FIG. 48), as the plasma is treated as a waste product, so there is less concern about any damage possibly caused to any cells carried by the plasma by the plasma pump P6 than damage possibly caused to the cellular blood components being conveyed to the fluid recipient by the red blood cell pump P5.

3. Centrifugal Separation—First Embodiment

Figure 2G:
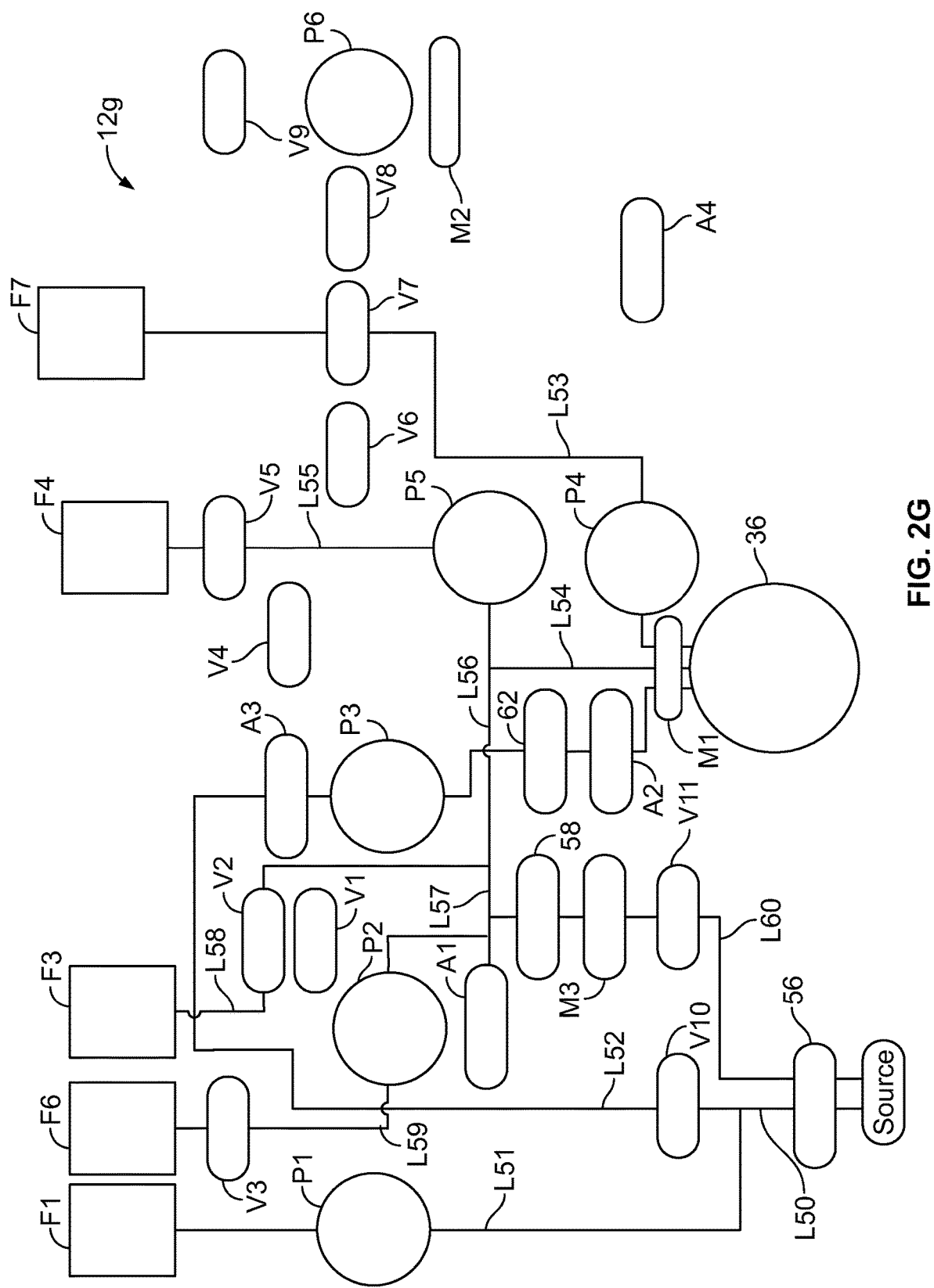
Figure 2H:
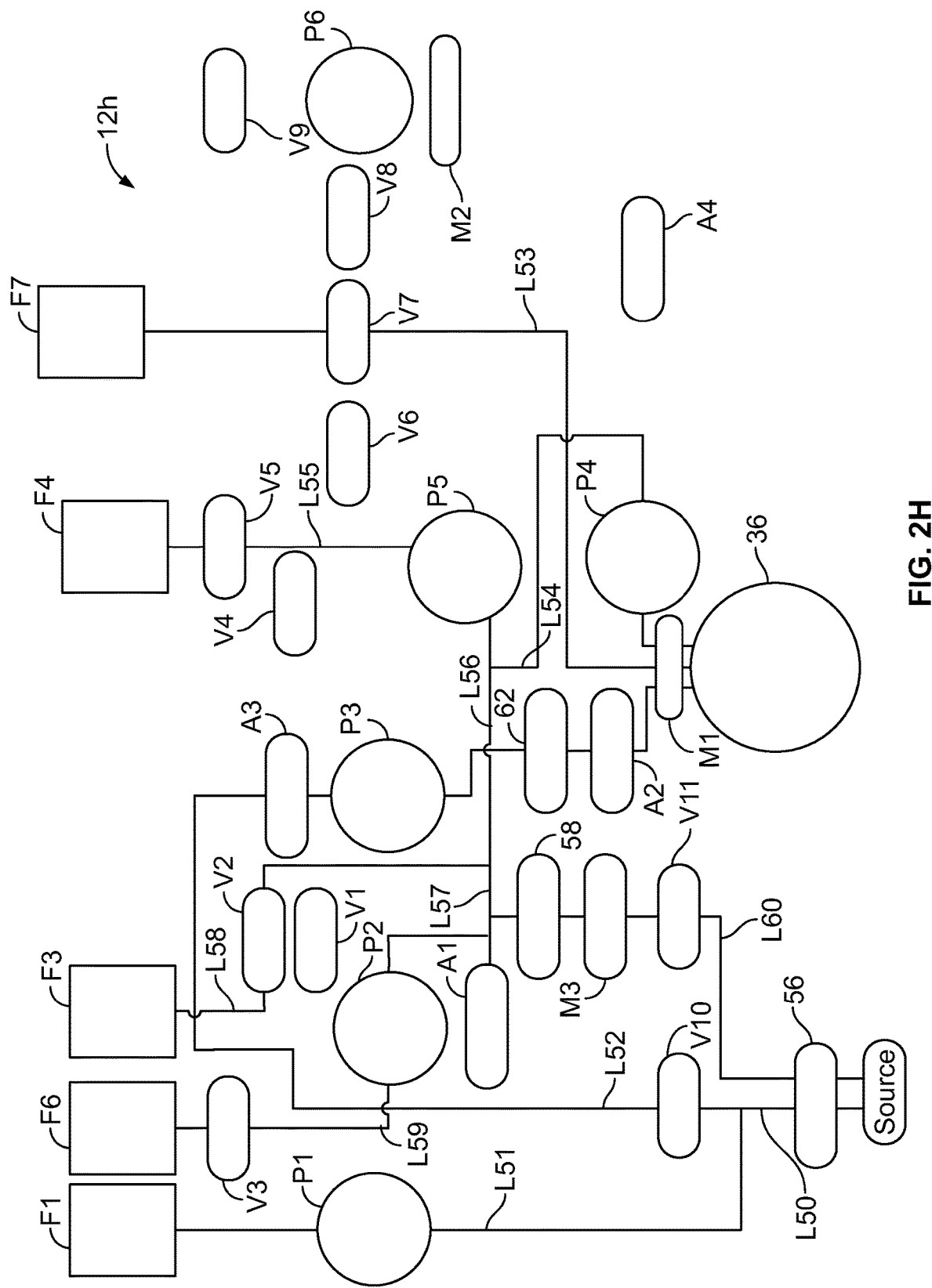

FIGS. 2G and 2H illustrate alternative embodiments of fluid flow circuits 12g, 12h suitable for execution of a therapeutic plasma exchange procedure using a centrifugal separation approach. While FIGS. 2G and 2H illustrate "double needle" configurations (in which separate blood access devices are employed to draw blood into the circuit from a blood source and to convey fluid to a recipient), it should be understood that a "single needle" configuration (in which a single blood access device is employed to both draw blood into the circuit from a blood source and return fluid to the same blood source) may instead be employed. The two fluid flow circuits 12g and 12h differ in the pump used to convey the separated blood components out of the centrifugal separation chamber 36, as will be described.

a. Fluid Flow Circuit

The fluid flow circuit 12g includes a cassette 48 of the type described above and illustrated in FIG. 4, which connects the various components of the fluid flow circuit 12g. The various connections amongst the components of the fluid flow circuit 12f are shown in FIG. 2G, which also shows the fluid flow circuit 12g mounted to the blood separation device 10.

Components of the fluid flow circuit 12g interact with many of the components of the blood separation device 10, as will be described, but there are selected components of the blood separation device 10 that are not used in a therapeutic plasma exchange procedure using the fluid flow circuit 12g of FIG. 2G. Most notably, the spinning membrane separator drive unit 14 is not used, but only the centrifugal separator 16. There are also selected valves V1, V4, V6, V8, and V9, one pump P6, one pressure sensor A4, and the spinner outlet sensor M2 of the blood separation device 10 that are not used in the procedure described herein. The fluid flow circuit 12g includes a waste container F3 that, in the illustrated procedure of FIG. 49, is only used during the pre-processing priming phase, in which saline from the saline container F4 is pumped through the fluid flow circuit 12g to prime it, before being conveyed to the waste container F3 for disposal at the end of the procedure.

However, it is also within the scope of the present disclosure for fluid to be conveyed into the waste container F3 and/or for saline to be conveyed to a fluid recipient from the saline container F4 during a procedure of this type.

b. Procedure

Figure 49:
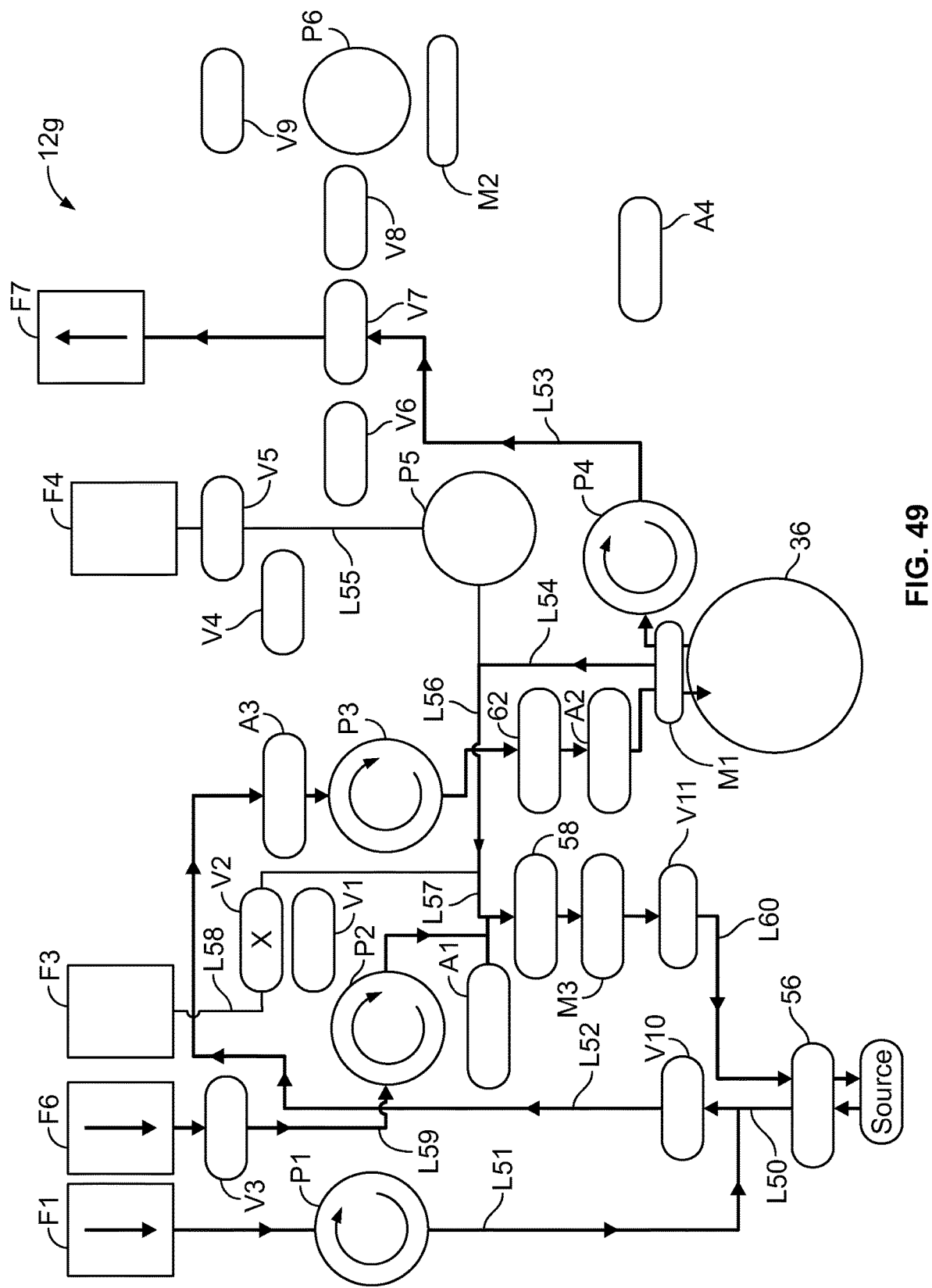
FIG. 49 is a schematic view of the fluid flow circuit of FIG. 2G mounted on the blood separation device of FIG. 1, showing the system carrying out different fluid flow tasks in connection with a therapeutic plasma exchange procedure using a centrifugal separation approach.

Blood is drawn into the fluid flow circuit 12g from a blood source (e.g., using a needle) via line L50, as shown in FIG. 49. The line L50 may include a manual clamp 56 that may initially be in a closed position to prevent fluid flow through the line L50. When processing is to begin, an operator may move the manual clamp 56 from its closed position to an open position to allow fluid flow through the line L50.

The blood is drawn into the line L50 by pump P3 (which is referred to as a centrifuge pump when describing this procedure). Anticoagulant from the anticoagulant bag F1 may be added to the blood via line L51 by action of the anticoagulant pump P1. The valve V10 associated with valve station C10 is open to allow the flow of anticoagulated blood through line L52 and through a sensor station S3 associated with pressure station A3. If the blood source is a living body (e.g., a patient), the pressure sensor A3 may communicate with the controller 18 to monitor the pressure within the vein of the blood source.

The blood flowing through line L52 passes through an air trap 62, a sensor station S2 associated with pressure sensor A2, and a centrifugal separator sensor M1, before entering the centrifugal separation chamber 36. The sensors A2 and M1 may be configured to operate in accordance with the preceding description of the procedure of FIG. 45.

The centrifugal separator 16 of the blood separation device 10 manipulates the centrifugal separation chamber 36 to separate red blood cells from a plasma constituent, which will typically be platelet-rich plasma, but may also be platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and platelet-rich plasma (as described above).

The plasma constituent is pumped out of the centrifugal separation chamber 36 via line L53 under action of pump P4 (which is referred to as a plasma pump when describing this procedure). Valve V7 is open to allow fluid flow through associated valve station C7 and into the plasma container F7.

The red blood cells flow out of the centrifugal separation chamber 36 via line L54. There is no pump associated with line L54, so instead the flow rate at which the red blood cells exit the centrifugal separation chamber 36 is equal to the difference between the flow rates of the centrifuge pump P3 and plasma pump P4.

The pump P5 (which is referred to as a saline pump when describing this procedure) associated with line L55 is inactive, thus directing the red blood cells into line L56 and to a junction. Valve V2 associated with valve station C2 is closed, thereby directing the red blood cells through line L57 instead of through line L58. The replacement fluid pump P2 associated with line L59 operates to draw a plasma replacement fluid (e.g., plasma from a donor) from plasma replacement fluid container F6. The replacement fluid travels through the valve station C3 associated with open valve V3 and to the junction with line L57, where it mixes with the red blood cells.

The mixture travels through the sensor station S1 associated with pressure sensor A1 (which may monitor vein pressure if the fluid recipient is a living donor), a return line filter 58, air detector M3, the valve station C11 associated with open valve V11, and line L60 on its way to the recipient (which may be the same as the blood source) via the second needle or blood access device. As noted above, it is also possible for saline from the saline container F4 to be mixed with the red blood cells at the junction of lines L54 and L55 under action of the saline pump P5 prior to the red blood cells reaching the fluid recipient.

This single-phase procedure continues until an objective has been completed (e.g., a particular amount of plasma has been collected in the plasma container F7).

4. Centrifugal Separation—Second Embodiment a. Fluid Flow Circuit

The fluid flow circuit 12h of FIG. 2H is similar to the fluid flow circuit 12g of FIG. 2G, but is differently associated to the pump system of the blood separation device 10, as noted above.

Figure 50:
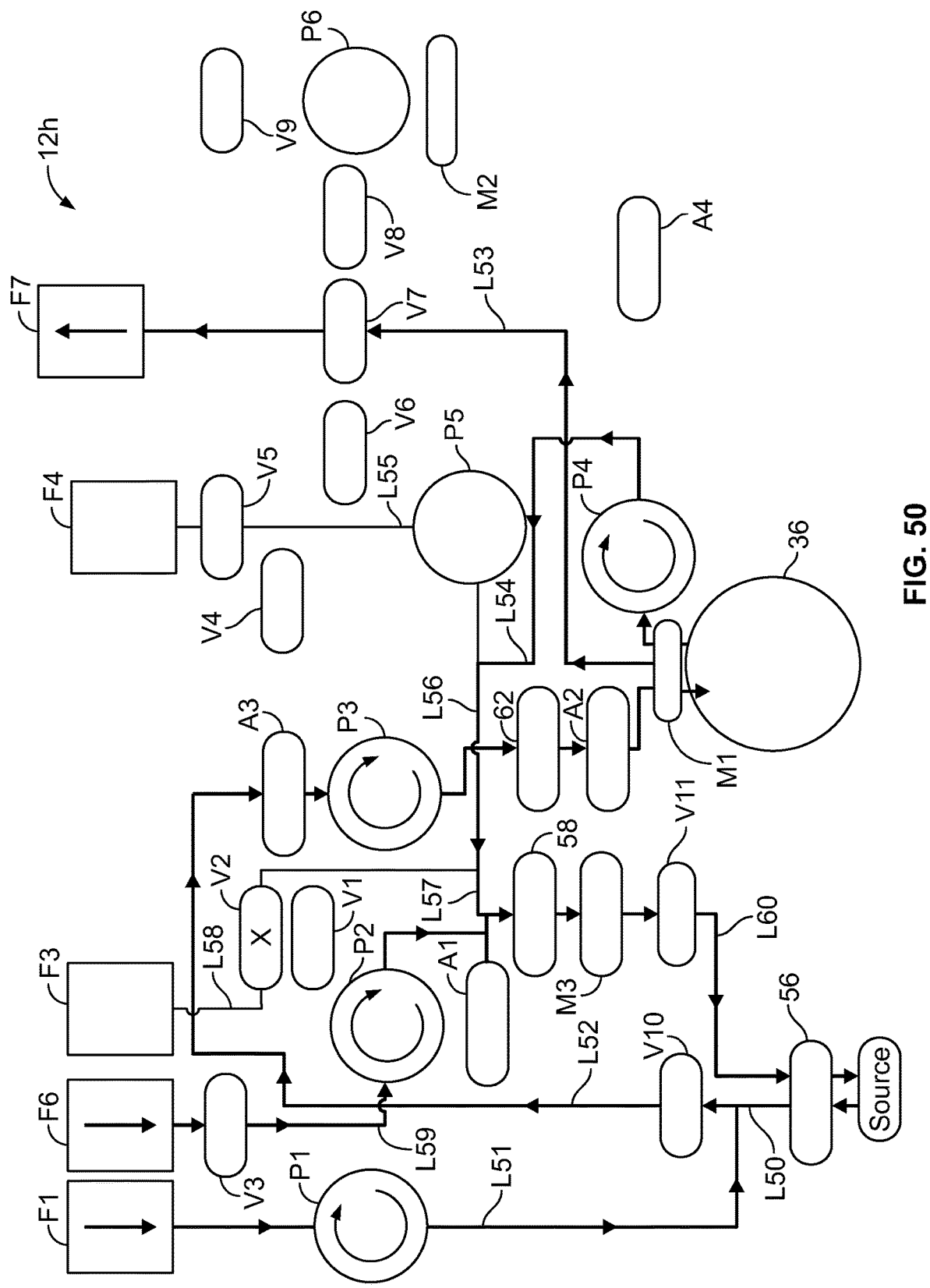
FIG. 50 is a schematic view of the fluid flow circuit of FIG. 2H mounted on the blood separation device of FIG. 1, showing the system carrying out different fluid flow tasks in connection with a therapeutic plasma exchange procedure using a centrifugal separation approach.

Components of the fluid flow circuit 12h interact with many of the components of the blood separation device 10, as will be described, but there are selected components of the blood separation device 10 that are not used in a therapeutic plasma exchange procedure using the fluid flow circuit 12g of FIG. 2G. Most notably, the spinning membrane separator drive unit 14 is not used, but only the centrifugal separator 16. There are also selected valves V1, V4, V6, V8, and V9, one pump P6, one pressure sensor A4, and the spinner outlet sensor M2 of the blood separation device 10 that are not used in the procedure described herein. The fluid flow circuit 12h includes a waste container F3 that, in the illustrated procedure of FIG. 50, is only used during the pre-processing priming phase, in which saline from the saline container F4 is pumped through the fluid flow circuit 12h to prime it, before being conveyed to the waste container F3 for disposal at the end of the procedure. However, it is also within the scope of the present disclosure for fluid to be conveyed into the waste container F3 and/or for saline to be conveyed to a fluid recipient from the saline container F4 during a procedure of this type.

b. Procedure

Blood is drawn into the fluid flow circuit 12h from a blood source (e.g., using a needle) via line L50, as shown in FIG. 50. The line L50 may include a manual clamp 56 that may initially be in a closed position to prevent fluid flow through the line L50. When processing is to begin, an operator may move the manual clamp 56 from its closed position to an open position to allow fluid flow through the line L50.

The blood is drawn into the line L50 by the centrifuge pump P3. Anticoagulant from the anticoagulant bag F1 may be added to the blood via line L51 by action of the anticoagulant pump P1. The valve V10 associated with valve station C10 is open to allow the flow of anticoagulated blood through line L52 and through a sensor station S3 associated with pressure station A3. If the blood source is a living body (e.g., a patient), the pressure sensor A3 may communicate with the controller 18 to monitor the pressure within the vein of the blood source.

The blood flowing through line L52 passes through an air trap 62, a sensor station S2 associated with pressure sensor A2, and a centrifugal separator sensor M1, before entering the centrifugal separation chamber 36, as in the procedure of FIG. 49.

The centrifugal separator 16 of the blood separation device 10 manipulates the centrifugal separation chamber 36 to separate red blood cells from a plasma constituent, which will typically be platelet-rich plasma, but may also be platelet-poor plasma, depending on the configuration of the centrifugal separation chamber 36 and/or the rate at which the centrifugal separation chamber 36 is rotated. In one embodiment, the centrifugal separator 16 may rotate the centrifugal separation chamber 36 at approximately 4,500 rpm to separate blood entering the centrifugal separation chamber 36 into red blood cells and platelet-rich plasma (as described above).

Rather than the plasma constituent being pumped out of the centrifugal separation chamber 36 (as in the procedure of FIG. 49), the red blood cells are instead pumped out of the centrifugal separation chamber 36 via line L54 by the pump P4 (which is referred to as the red blood cell pump when described this procedure).

The saline pump P5 associated with line L55 is inactive, thus directing the red blood cells into line L56 and to a junction. Valve V2 associated with valve station C2 is closed, thereby directing the red blood cells through line L57 instead of through line L58. The replacement fluid pump P2 associated with line L59 operates to draw a plasma replacement fluid (e.g., plasma from a donor) from plasma replacement fluid container F6. The replacement fluid travels through the valve station C3 associated with open valve V3 and to the junction with line L57, where it mixes with the red blood cells.

The mixture travels through the sensor station S1 associated with pressure sensor A1, the return line filter 58, air detector M3, the valve station C11 associated with open valve V11, and line L60 on its way to the recipient (which may be the same as the blood source) via the second needle or blood access device. As noted above, it is also possible for saline from the saline container F4 to be mixed with the red blood cells at the junction of lines L54 and L55 under action of the saline pump P5 prior to the red blood cells reaching the fluid recipient.

As for the plasma constituent, it exits the centrifugal separation chamber 36 via line L53. There is no pump associated with line L53, so instead the flow rate at which the plasma constituent exits the centrifugal separation chamber 36 is equal to the difference between the flow rates of the centrifuge pump P3 and red blood cell pump P4. Valve V7 is open to allow fluid flow through associated valve station C7 and into the plasma container F7.

This single-phase procedure continues until an objective has been completed (e.g., a particular amount of plasma has been collected in the plasma container F7).

The preference of using the pump P4 to remove red blood cells or the plasma constituent from the centrifugal separation chamber 36 may depend on any of a number of factors. In general, though, it may be preferred to use the pump P4 as a plasma pump (as in the procedure of FIG. 49), as the plasma is treated as a waste product, so there is less concern about any damage possibly caused to any cells carried by the plasma by the pump P4 than damage possibly caused to the red blood cells by the pump P4 (as in the procedure of FIG. 50).

IV. Spinning Membrane Separation Versus Centrifugal Separation

The controller 18 may be configured to receive instructions to control the various components of the blood separation device 10 to execute a therapeutic exchange procedure using either the spinning membrane separator drive unit 14 or the centrifugal separator 16. Alternatively (or additionally), the controller 18 may be configured to determine whether to control the various components of the blood separation device 10 to execute a therapeutic exchange procedure using either the spinning membrane separator drive unit 14 or the centrifugal separator 16.

Any of a number of factors may go into the decision (whether determined by an operator or by the controller 18) to use the spinning membrane separator drive unit 14 or the centrifugal separator 16 to execute a therapeutic exchange procedure. For example, the amount of time required to complete a therapeutic exchange procedure may be a factor in selecting to use the spinning membrane separator drive unit 14 or the centrifugal separator 16. For any particular separation efficiency, a centrifugal separator 16 can typically accommodate faster flow rates than a spinning membrane separator drive unit 14, such that there may be a preference for using the centrifugal separator 16 for a therapeutic exchange procedure if there is limited time to complete the procedure or if time is otherwise a greater concern. If a spinning membrane separator 26 is to be used for a therapeutic exchange procedure, the processing time may be reduced by employing a larger spinning membrane separator 26, rather than a smaller spinning membrane separator 26. On the other hand, some therapeutic exchange procedures may take upwards of eight hours to complete. The umbilicus 46 connected to a centrifugal separation chamber 36 is typically not validated to last that long, whereas a larger spinning membrane separator 26 has been proven to operate successfully over 8-10 hour durations. As such, spinning membrane separation using a larger spinning membrane separator 26 may be preferred when it is known or estimated or determined that a therapeutic exchange procedure will take a longer amount of time to complete.

Another possible consideration is the possibility of clogging a spinning membrane separator 26 associated with the spinning membrane separator drive unit 14. This may be a greater concern depending on the condition of the blood. For example, it may be preferable to employ the centrifugal separator 16 for a therapeutic plasma exchange procedure when processing blood from a source having hypercholesteremia, on account of an increased risk of clogging a spinning membrane separator 26.

Yet another possible consideration is the risk of damaging at least one blood component. The centrifugal separator 16 will tend to subject cellular blood components to less shear stress than the spinning membrane separator drive unit 14, such that use of the centrifugal separator 16 may be preferred, particularly for a therapeutic plasma exchange procedure and/or when processing blood from a source having a disease causing weakening of the cells.

Another possible consideration is the amount of platelets separated from blood with the "waste product" (i.e., red blood cells in a therapeutic red blood cell exchange procedure and plasma in a therapeutic plasma exchange procedure). Centrifugal separation will tend to separate blood into red blood cells and platelet-rich plasma, whereas spinning membrane separation will tend to separate blood into platelet-poor plasma and cellular blood components. Thus, for a therapeutic red blood cell exchange procedure, it may be advantageous to employ the centrifugal separator 16, as more platelets will be available in the plasma being conveyed to the fluid recipient. Similarly, for a therapeutic plasma exchange procedure, it may be advantageous to employ the spinning membrane separator drive unit 14, as more platelets will be available with the red blood cells being conveyed to the fluid recipient. However, if (for other reasons) it is desired to use the spinning membrane separator drive unit 14 for a therapeutic red blood cell exchange procedure, the membrane 76 of the spinning membrane separator 26 may be provided with larger pores in order to allow more platelets to be separated from the red blood cells with the plasma to be conveyed to the fluid recipient. Similarly, if (for other reasons) it is desired to use the centrifugal separator 16 for a therapeutic plasma exchange procedure, the controller 18 may control the centrifugal separator 16 so as to separate more platelets from the plasma (though typically not as many as is possible when using a spinning membrane separator 26), thereby increasing the number of platelets available to be conveyed to the fluid recipient with the separated red blood cells.

Yet another possible consideration is the age and/or weight of the blood source, if the blood source is a human. A smaller spinning membrane separator 26 will require a lower extracorporeal blood volume (on the order of approximately 10 mL) than a larger spinning membrane separator 26 (on the order of approximately 30 mL) and a centrifugal separation chamber 36 (on the order of approximately 50 mL). As such, use of a smaller spinning membrane separator 26 may be preferred when the blood source is a child. Between a larger spinning membrane separator 26 and a centrifugal separation chamber 36, the larger spinning membrane separator 26 will tend to require a lower extracorporeal blood volume. Accordingly, if the spinning membrane separator drive unit 14 is to be employed for a therapeutic exchange procedure, use of a larger spinning membrane separator 26 may be preferred to a smaller spinning membrane separator 26, provided that the blood source can accommodate the greater required extracorporeal blood volume. On the other hand, as noted above, centrifugal separation may allow for greater flow rates and shorter procedure times, such that centrifugal separation may be preferred when the blood source is an adult.

Another possible consideration is the cost of the fluid flow circuit 12 employed when using the spinning membrane separator drive unit 14 versus the centrifugal separator 16. A fluid flow circuit 12 having only a spinning membrane separator 26 will tend to be less expensive than a fluid flow circuit having only a centrifugal separation chamber 36. Thus, when the cost of the fluid flow circuit 14 is a greater consideration (e.g., in developing areas), it may be preferred to use the spinning membrane separator drive unit 14 for therapeutic exchange procedures. While the fluid flow circuits 12 of FIGS. 2A-2H are shown as having only a spinning membrane separator 26 or only a centrifugal separation chamber 36, it should be understood that any of the fluid flow circuits 12 may be provided with both a spinning membrane separator 26 and a centrifugal separation chamber 36, with only one of them being employed for a therapeutic exchange procedure. While this would increase the cost of a fluid flow circuit 12, it would increase the flexibility of the fluid flow circuit 12, by allowing the same fluid flow circuit 12 to be used for either centrifugal separation or spinning membrane separation.

Another possible consideration is the dependence of the centrifugal separator 16 on cell size, shape, and/or density for efficient separation. The spinning membrane separator 26 may filter cellular blood components from plasma regardless of cell size, shape, or density, whereas separation using the centrifugal separation chamber 36 is based on sedimentation that may be strongly affected by red blood cell size, shape, and density (for example). Accordingly, if a blood source has a condition or disease causing abnormalities in the size, shape, and/or density of its red blood cells, it may be advantageous to employ the spinning membrane separator drive unit 14.

One or more of these possible competing interests and considerations (and/or other considerations) may be factored into the decision of which separation approach to employ. As noted above, it is within the scope of the present disclosure for an operator to make this determination and then instruct the controller 18 to carry out a therapeutic exchange procedure using a particular separation approach. Alternatively, the determination may be made by the controller 18, with data being provided to the controller 18 for determining which separation approach to employ. It is also within the scope of the present disclosure for the decision to be made by collaboration between the operator and the controller 18, such as with the controller 18 recommending a separation approach and the operator approving or disapproving of the recommendation.

Aspects

Aspect 1. A blood separation device comprising: a centrifugal separator; a spinning membrane separator drive unit; a pump system; and a controller configured to control the centrifugal separator or the spinning membrane separator drive unit to execute a therapeutic red blood cell exchange procedure, wherein the controller is further configured to, when controlling the centrifugal separator to execute a therapeutic red blood cell exchange procedure, control the pump system to convey blood from a blood source into the centrifugal separator, control the centrifugal separator to separate at least a portion of the blood into red blood cells and at least one other blood component, control the pump system to collect at least a portion of the separated red blood cells, control the pump system to add a red blood cell replacement fluid to said at least one other blood component, and control the pump system to convey at least a portion of the red blood cell replacement fluid and said at least one other blood component to a recipient, and the controller is further configured to, when controlling the spinning membrane separator drive unit to execute a therapeutic red blood cell exchange procedure, control the pump system to convey blood from a blood source into the spinning membrane separator drive unit, control the spinning membrane separator drive unit to separate at least a portion of the blood into red blood cells and at least one other blood component, control the pump system to collect at least a portion of the separated red blood cells, control the pump system to add a red blood cell replacement fluid to said at least one other blood component, and control the pump system to convey at least a portion of the red blood cell replacement fluid and said at least one other blood component to a recipient.

Aspect 2. The blood separation device of Aspect 1, wherein the controller is configured to receive instructions to control the centrifugal separator or the spinning membrane separator drive unit to execute said therapeutic red blood cell exchange procedure.

Aspect 3. The blood separation device of Aspect 1, wherein the controller is configured to determine whether to control the centrifugal separator or the spinning membrane separator drive unit to execute said therapeutic red blood cell exchange procedure.

Aspect 4. The blood separation device of Aspect 3, wherein the determination whether to control the centrifugal separator or the spinning membrane separator drive unit to execute said therapeutic red blood cell exchange procedure is based at least in part on one or more of: an amount of time determined to be required to complete said therapeutic red blood cell exchange procedure when using the centrifugal separator versus an amount of time determined to be required to complete said therapeutic red blood cell exchange procedure when using the spinning membrane separator drive unit, a likelihood of clogging a spinning membrane separator associated with the spinning membrane separator drive unit when using the spinning membrane separator drive unit to execute said therapeutic red blood cell exchange procedure, a likelihood of damaging at least one blood component when using the centrifugal separator to execute said therapeutic red blood cell exchange procedure versus a likelihood of damaging at least one blood component when using the spinning membrane separator drive unit to execute said therapeutic red blood cell exchange procedure, an amount of platelets estimated to be separated from said at least one other blood component when using the centrifugal separator to execute said therapeutic red blood cell exchange procedure versus an amount of platelets estimated to be separated from said at least one other blood component when using the spinning membrane separator drive unit to execute said therapeutic red blood cell exchange procedure, an age and/or weight of the blood source, when the blood source is a living human, an extracorporeal blood volume required when using the centrifugal separator to execute said therapeutic red blood cell exchange procedure versus an extracorporeal blood volume required when using the spinning membrane separator drive unit to execute said therapeutic red blood cell exchange procedure, and a cost of a fluid flow circuit employed when using the centrifugal separator to execute said therapeutic red blood cell exchange procedure versus a cost of a fluid flow circuit employed when using the spinning membrane separator drive unit to execute said therapeutic red blood cell exchange procedure.

Aspect 5. The blood separation device of any one of the preceding Aspects, wherein the spinning membrane separator drive unit is configured to accommodate differently sized spinning membrane separators, and the controller is configured to control the spinning membrane separator drive unit to execute said therapeutic red blood cell exchange procedure using any one of said differently sized spinning membrane separators.

Aspect 6. The blood separation device of any one of the preceding Aspects, wherein the pump system includes a first pump configured to convey blood from the blood source into the centrifugal separator or the spinning membrane separator drive unit and a second pump configured to convey the separated red blood cells from the centrifugal separator or the spinning membrane separator drive unit.

Aspect 7. The blood separation device of any one of Aspects 1-5, wherein the pump system includes a first pump configured to convey blood from the blood source into the centrifugal separator or the spinning membrane separator drive unit and a second pump configured to convey said at least one other blood component from the centrifugal separator or the spinning membrane separator drive unit.

Aspect 8. The blood separation device of any one of the preceding Aspects, configured to convey blood from the blood source via a first blood access device of a fluid flow circuit associated to the blood separation device and to convey the red blood cell replacement fluid and said at least one other blood component to the recipient via a second blood access device of said fluid flow circuit.

Aspect 9. The blood separation device of any one of the preceding Aspects, wherein the red blood cell replacement fluid comprises donated red blood cells.

Aspect 10. The blood separation device of any one of the preceding Aspects, configured as a mobile device.

Aspect 11. A blood separation device comprising: a centrifugal separator; a spinning membrane separator drive unit; a pump system; and a controller configured to control the centrifugal separator or the spinning membrane separator drive unit to execute a therapeutic plasma exchange procedure, wherein the controller is further configured to, when controlling the centrifugal separator to execute a therapeutic plasma exchange procedure, control the pump system to convey blood from a blood source into the centrifugal separator, control the centrifugal separator to separate at least a portion of the blood into plasma and at least one other blood component, control the pump system to collect at least a portion of the separated plasma, control the pump system to add a plasma replacement fluid to said at least one other blood component, and control the pump system to convey at least a portion of the plasma replacement fluid and said at least one other blood component to a recipient, and the controller is further configured to, when controlling the spinning membrane separator drive unit to execute a therapeutic plasma exchange procedure, control the pump system to convey blood from a blood source into the spinning membrane separator drive unit, control the spinning membrane separator drive unit to separate at least a portion of the blood into plasma and at least one other blood component, control the pump system to collect at least a portion of the separated plasma, control the pump system to add a plasma replacement fluid to said at least one other blood component, and control the pump system to convey at least a portion of the plasma replacement fluid and said at least one other blood component to a recipient.

Aspect 12. The blood separation device of Aspect 11, wherein the controller is configured to receive instructions to control the centrifugal separator or the spinning membrane separator drive unit to execute said therapeutic plasma exchange procedure.

Aspect 13. The blood separation device of Aspect 11, wherein the controller is configured to determine whether to control the centrifugal separator or the spinning membrane separator drive unit to execute said therapeutic plasma exchange procedure.

Aspect 14. The blood separation device of Aspect 13, wherein the determination whether to control the centrifugal separator or the spinning membrane separator drive unit to execute said therapeutic plasma exchange procedure is based at least in part on one or more of: an amount of time determined to be required to complete said therapeutic plasma exchange procedure when using the centrifugal separator versus an amount of time determined to be required to complete said therapeutic plasma exchange procedure when using the spinning membrane separator drive unit, a likelihood of clogging a spinning membrane separator associated with the spinning membrane separator drive unit when using the spinning membrane separator drive unit to execute said therapeutic plasma exchange procedure, a likelihood of damaging at least one blood component when using the centrifugal separator to execute said therapeutic plasma exchange procedure versus a likelihood of damaging at least one blood component when using the spinning membrane separator drive unit to execute said therapeutic plasma exchange procedure, an amount of platelets estimated to be separated from said at least one other blood component when using the centrifugal separator to execute said therapeutic plasma exchange procedure versus an amount of platelets estimated to be separated from said at least one other blood component when using the spinning membrane separator drive unit to execute said therapeutic plasma exchange procedure, an age and/or weight of the blood source, when the blood source is a living human, an extracorporeal blood volume required when using the centrifugal separator to execute said therapeutic plasma exchange procedure versus an extracorporeal blood volume required when using the spinning membrane separator drive unit to execute said therapeutic plasma exchange procedure, and a cost of a fluid flow circuit employed when using the centrifugal separator to execute said therapeutic plasma exchange procedure versus a cost of a fluid flow circuit employed when using the spinning membrane separator drive unit to execute said therapeutic plasma exchange procedure.

Aspect 15. The blood separation device of any one of Aspects 11-14, wherein the spinning membrane separator drive unit is configured to accommodate differently sized spinning membrane separators, and the controller is configured to control the spinning membrane separator drive unit to execute said therapeutic plasma exchange procedure using any one of said differently sized spinning membrane separators.

Aspect 16. The blood separation device of any one of Aspects 11-15, wherein the pump system includes a first pump configured to convey blood from the blood source into the centrifugal separator or the spinning membrane separator drive unit and a second pump configured to convey the separated plasma from the centrifugal separator or the spinning membrane separator drive unit.

Aspect 17. The blood separation device of any one of Aspects 11-15, wherein the pump system includes a first pump configured to convey blood from the blood source into the centrifugal separator or the spinning membrane separator drive unit and a second pump configured to convey said at least one other blood component from the centrifugal separator or the spinning membrane separator drive unit.

Aspect 18. The blood separation device of any one of Aspects 11-17, configured to convey blood from the blood source via a first blood access device of a fluid flow circuit associated to the blood separation device and to convey the plasma replacement fluid and said at least one other blood component to the recipient via a second blood access device of said fluid flow circuit.

Aspect 19. The blood separation device of any one of Aspects 11-18, wherein the plasma replacement fluid comprises donated plasma.

Aspect 20. The blood separation device of any one of Aspects 11-19, configured as a mobile device.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood separation device comprising:
 a centrifugal separator;
 a spinning membrane separator drive unit;
 a pump system; and
 a controller programmed to execute a first version of a therapeutic red blood cell exchange procedure in which the centrifugal separator and the pump system are operative and the spinning membrane separator is not operative and a second version of the therapeutic red blood cell exchange
 procedure in which the spinning membrane separator drive unit and the pump system are operative and the centrifugal separator is not operative, wherein the controller is programmed to determine whether to execute the first version or the second version of the therapeutic red blood cell exchange procedure based on analysis of one or more of a plurality of factors indicating a preference for execution of the first version of the therapeutic red blood cell exchange procedure or a preference for execution of the second version of the therapeutic red blood cell exchange procedure, with the controller being programmed to
  determine that the first version of the therapeutic red blood cell exchange procedure is to be executed upon determining or receiving input indicating only a preference for execution of the first version of the therapeutic red blood cell exchange procedure,
  determine that the second version of the therapeutic red blood cell exchange procedure is to be executed upon determining or receiving input indicating only a preference for execution of the second version of the therapeutic red blood cell exchange procedure, and
  upon determining that there is at least one factor indicating a preference for execution of the first version of the therapeutic red blood cell exchange procedure and at least one factor indicating a preference for execution of the second version of the therapeutic red blood cell exchange procedure, compare the various factors before making a determination of the version of the therapeutic red blood cell exchange procedure to be executed.

2. The blood separation device of claim 1, wherein the determination whether to execute the first version or the second version of said therapeutic red blood cell exchange procedure is based at least in part on one or more of:
 an amount of time determined to be required to complete the first version of said therapeutic red blood cell exchange procedure versus an amount of time determined to be required to complete the second version of said therapeutic red blood cell exchange procedure,
 a likelihood of clogging a spinning membrane separator associated with the spinning membrane separator drive unit when executing the second version of said therapeutic red blood cell exchange procedure,
 a likelihood of damaging at least one blood component when executing the first version of said therapeutic red blood cell exchange procedure versus a likelihood of damaging at least one blood component when executing the second version of said therapeutic red blood cell exchange procedure,
 an amount of platelets estimated to be separated from said at least one other blood component executing the first version of said therapeutic red blood cell exchange procedure versus an amount of platelets estimated to be separated from said at least one other blood component when executing the second version of said therapeutic red blood cell exchange procedure,
 an age and/or weight of the blood source, when the blood source is a living human, an extracorporeal blood volume required when executing the first version of said therapeutic red blood cell exchange procedure versus an extracorporeal blood volume required when executing the second version of said therapeutic red blood cell exchange procedure, and a cost of a fluid flow circuit employed when executing the first version of said therapeutic red blood cell exchange procedure versus a cost of a fluid flow circuit employed when executing the second version of said therapeutic red blood cell exchange procedure.

3. The blood separation device of claim 1, wherein the spinning membrane separator drive unit is configured to accommodate differently sized spinning membrane separators, and the controller is programmed to execute the second version of said therapeutic red blood cell exchange procedure using any one of said differently sized spinning membrane separators.

4. The blood separation device of claim 1, wherein the pump system includes a first pump configured to convey blood from the blood source into the centrifugal separator or the spinning membrane separator drive unit and a second pump configured to convey the separated red blood cells from the centrifugal separator or the spinning membrane separator drive unit.

5. The blood separation device of claim 1, wherein the pump system includes a first pump configured to convey blood from the blood source into the centrifugal separator or the spinning membrane separator drive unit and a second pump configured to convey said at least one other blood component from the centrifugal separator or the spinning membrane separator drive unit.

6. The blood separation device of claim 1, configured to convey blood from the blood source via a first blood access device of a fluid flow circuit associated to the blood separation device and to convey the red blood cell replacement fluid and said at least one other blood component to the recipient via a second blood access device of said fluid flow circuit.

7. The blood separation device of claim 1, wherein the red blood cell replacement fluid comprises donated red blood cells.

8. The blood separation device of claim 1, configured as a mobile device.

9. The blood separation device of claim 1, wherein the controller is programmed to determine a preference for execution of the first version of the therapeutic red blood cell exchange procedure upon determining or receiving input indicating that: (1) there is a limited time to complete the therapeutic red blood cell exchange procedure or that a shorter procedure time is preferred, (2) blood to be separated is provided by a blood source having hypercholesteremia, (3) there is a preference for a reduced risk of damaging a cellular blood component or that blood to be separated is provided by a blood source having a condition causing weakening of a cellular blood component, (4) platelets are to be returned to the blood source, and/or (5) blood to be separated is provided by a blood source that is an adult, and determine a preference for execution of the second version of the therapeutic red blood cell exchange procedure upon determining or receiving input indicating that: (1) the therapeutic red blood cell exchange procedure will require eight or more hours to complete, (2) platelets are not to be returned to the blood source, (3) blood to be separated is provided by a blood source that is a child, (4) a relatively low cost of a fluid flow circuit used in combination with the blood separation device during execution of the therapeutic red blood cell exchange procedure is preferred, and/or (5) a shape, shape, and/or density of red blood cells in blood to be separated is abnormal.

10. A blood separation device comprising:

a centrifugal separator;

a spinning membrane separator drive unit;

a pump system; and a controller programmed to execute a first version of a therapeutic plasma exchange procedure in which the centrifugal separator and the pump system are operative and the spinning membrane separator is not operative and a second version of the therapeutic plasma exchange procedure in which the spinning membrane separator drive unit and the pump system are operative and the centrifugal separator is not operative, wherein the controller is programmed to determine whether to execute the first version or the second version of the therapeutic plasma exchange procedure based on analysis of one or more of a plurality of factors indicating a preference for execution of the first version of the therapeutic plasma exchange procedure or a preference for execution of the second version of the therapeutic plasma exchange procedure, with the controller being programmed to determine that the first version of the therapeutic plasma exchange procedure is to be executed upon determining or receiving input indicating only a preference for execution of the first version of the therapeutic plasma exchange procedure, determine that the second version of the therapeutic plasma exchange procedure is to be executed upon determining or receiving input indicating only a preference for execution of the second version of the therapeutic plasma exchange procedure, and upon determining that there is at least one factor indicating a preference for execution of the first version of the therapeutic plasma procedure and at least one factor indicating a preference for execution of the second version of the therapeutic plasma exchange procedure, compare the various factors before making a determination of the version of the therapeutic plasma exchange procedure to be executed.

11. The blood separation device of claim 10, wherein the determination whether to execute the first version or the second version of said therapeutic plasma exchange procedure is based at least in part on one or more of:

an amount of time determined to be required to complete the first version of said therapeutic plasma exchange versus an amount of time determined to be required to complete the second version of said therapeutic plasma exchange procedure, a likelihood of clogging a spinning membrane separator associated with the spinning membrane separator drive unit when executing the second version of said therapeutic plasma exchange procedure, a likelihood of damaging at least one blood component when executing the first version of said therapeutic plasma exchange procedure versus a likelihood of damaging at least one blood component when executing the second version of said therapeutic plasma exchange procedure, an amount of platelets estimated to be separated from said at least one other blood component when executing the first version of said therapeutic plasma exchange procedure versus an amount of platelets estimated to be separated from said at least one other blood component when executing the second version of said therapeutic plasma exchange procedure, an age and/or weight of the blood source, when the blood source is a living human, an extracorporeal blood volume required when executing the first version of said therapeutic plasma exchange procedure versus an extracorporeal blood volume required when executing the second version of said therapeutic plasma exchange procedure, and a cost of a fluid flow circuit employed when executing the first version of said therapeutic plasma exchange procedure versus a cost of a fluid flow circuit employed when executing the second version of said therapeutic plasma exchange procedure.

12. The blood separation device of claim 10, wherein the spinning membrane separator drive unit is configured to accommodate differently sized spinning membrane separators, and the controller is programmed to execute the second version of said therapeutic plasma exchange procedure using any one of said differently sized spinning membrane separators.

13. The blood separation device of claim 10, wherein the pump system includes a first pump configured to convey blood from the blood source into the centrifugal separator or the spinning membrane separator drive unit and a second pump configured to convey the separated plasma from the centrifugal separator or the spinning membrane separator drive unit.

14. The blood separation device of claim 10, wherein the pump system includes a first pump configured to convey blood from the blood source into the centrifugal separator or the spinning membrane separator drive unit and a second pump configured to convey said at least one other blood component from the centrifugal separator or the spinning membrane separator drive unit.

15. The blood separation device of claim 10, configured to convey blood from the blood source via a first blood access device of a fluid flow circuit associated to the blood separation device and to convey the plasma replacement fluid and said at least one other blood component to the recipient via a second blood access device of said fluid flow circuit.

16. The blood separation device of claim 10, wherein the plasma replacement fluid comprises donated plasma.

17. The blood separation device of claim 10, configured as a mobile device.

18. The blood separation device of claim 10, wherein the controller is programmed to determine a preference for execution of the first version of the therapeutic plasma exchange procedure upon determining or receiving input indicating that: (1) there is a limited time to complete the therapeutic plasma procedure or that a shorter procedure time is preferred, (2) blood to be separated is provided by a blood source having hypercholesteremia, (3) there is a preference for a reduced risk of damaging a cellular blood component or that blood to be separated is provided by a blood source having a condition causing weakening of a cellular blood component, (4) platelets are not to be returned to the blood source, and/or (5) blood to be separated is provided by a blood source that is an adult, and determine a preference for execution of the second version of the therapeutic plasma exchange procedure upon determining or receiving input indicating that: (1) the therapeutic plasma exchange procedure will require eight or more hours to complete, (2) platelets are to be returned to the blood source, (3) blood to be separated is provided by a blood source that is a child, (4) a relatively low cost of a fluid flow circuit used in combination with the blood separation device during execution of the therapeutic plasma exchange procedure is preferred, and/or (5) a shape, shape, and/or density of red blood cells in blood to be separated is abnormal.

* * * * *